United States Patent
Khan et al.

(10) Patent No.: US 12,183,434 B2
(45) Date of Patent: Dec. 31, 2024

(54) DIAGNOSTIC AND THERAPEUTIC METHODS FOR CANCER

(71) Applicant: Genentech, Inc., South San Francisco, CA (US)

(72) Inventors: Zia Khan, San Francisco, CA (US); Matthew Lawrence Albert, San Francisco, CA (US); G Scott Chandler, Basel (CH)

(73) Assignee: Genentech, Inc., South San Francisco, CA (US)

( * ) Notice: Subject to any disclaimer, the term of this patent is extended or adjusted under 35 U.S.C. 154(b) by 679 days.

(21) Appl. No.: 17/395,996

(22) Filed: Aug. 6, 2021

(65) Prior Publication Data
US 2022/0115087 A1    Apr. 14, 2022

Related U.S. Application Data

(63) Continuation of application No. PCT/US2020/017003, filed on Feb. 6, 2020.
(60) Provisional application No. 62/803,272, filed on Feb. 8, 2019.

(51) Int. Cl.
| | | |
|---|---|---|
| *G16B 20/20* | (2019.01) | |
| *G16B 30/00* | (2019.01) | |
| *G16H 10/40* | (2018.01) | |
| *G16H 20/40* | (2018.01) | |
| *G16H 50/30* | (2018.01) | |

(52) U.S. Cl.
CPC ............ *G16B 20/20* (2019.02); *G16B 30/00* (2019.02); *G16H 10/40* (2018.01); *G16H 20/40* (2018.01); *G16H 50/30* (2018.01)

(58) Field of Classification Search
CPC ........ G16B 20/20; G16B 30/00; G16H 10/40; G16H 20/40; G16H 50/30; C12Q 2537/165; C12Q 2600/106; C12Q 2600/156; C12Q 1/6886
See application file for complete search history.

(56) References Cited

FOREIGN PATENT DOCUMENTS

| | | | |
|---|---|---|---|
| CN | 107532217 A | 1/2018 | |
| CN | 108969763 A | 12/2018 | |
| CN | 109196121 A | 1/2019 | |
| CN | 109280695 A | 1/2019 | |
| JP | 2018-521976 A | 8/2018 | |
| WO | WO-2013173223 A1 | 11/2013 | |
| WO | WO-2016196298 A1 | 12/2016 | |
| WO | WO-2017151502 A1 | 9/2017 | |

OTHER PUBLICATIONS

Chatterjee et al. Developing and evaluating polygenic risk oredicyion models for stratified disease prevention. 2016. Nature. 17: 392-406. (Year: 2016).*
Zappasodi et al. Strategies for predicting response to checkpoint inhibitors. Curr Hematol Malig Rep. 2018. 13: 383-395. (Year: 2018).*
Cooper et al. Biomarkers that predict response to immunotherapy—no magic bullet. 2018. Cancer Forum. 42(1): 92-101. (Year: 2018).*
Yoest. Clinical features, predictive correlates, and pathophysiology of immune-related adverse events in immune checkpoint inhibitor treatments in cancer: a short review. 2017. ImmunoTargets and Therapy. 6: 73-82. (Year: 2017).*
Fahmy et al. The current status of checkpoint inhibitors in metastatic bladder cancer. 2016. Clin Exp Metasasis. 33: 629-635. (Year: 2016).*
Lim et al. Germline genetic polymorphisms influence tumor gene expression and immune cell infiltration. 2018. PNAS. 115(50):E11701-11710. (Year: 2018).*
Luo et al., "Immunotherapy-Mediated Thyroid Dysfunction: Genetic Risk and Impact on Outcomes with PD-1 Blockade in Non-Small Cell Lung Cancer," Clinical Cancer Research 27(18):5131-5140 (Sep. 2021).
Barnet et al., "Abstract LB-121: Exploring the germ-line contribution to exceptional response to PD-1/PD-L1 inhibition in patients with metastatic non-small-cell lung cancer by whole genome sequencing," Cancer Res. 78(13_Supplemental), LB-121, (2018).
Torkamani et al., "The personal and clinical utility of polygenic risk scores," Nature Reviews Genetics, 19: 581-590, (2018).
Ali et al., "Characterization of Nivolumab-Associated Skin Reactions in Patients With Metastatic Non-Small Cell Lung Cancer," Oncoimmunology. 5(11):e1231292 (2016) (5 pages).
Freeman-Keller et al., "Nivolumab in Resected and Unresectable Metastatic Melanoma: Characteristics of Immune-Related Adverse Events and Association With Outcomes," Clin Cancer Res. 22(4):886-94 (2015) (10 pages).
Haratani et al., "Association of Immune-Related Adverse Events With Nivolumab Efficacy in Non-Small-Cell Lung Cancer," JAMA Oncol 4(3):374-8 (2018).
Spain et al., "Management of Toxicities of Immune Checkpoint Inhibitors," Cancer Treat Rev. 44:51-60 (2016).
Toi et al., "Association of Immune-Related Adverse Events With Clinical Benefit in Patients With Advanced Non-Small-Cell Lung Cancer Treated With Nivolumab," Oncologist. 23(11):1358-65 (2018).
Wills et al., "Treatment of Complications From Immune Checkpoint Inhibition in Patients With Lung Cancer," Curr Treat Options Oncol. 19(9):46 (2018) (21 pages).
Yin et al., "A weighted polygenic risk score using 14 known susceptibility variants to estimate risk and age onset of psoriasis in Han Chinese," PLoS One. 10(5):e0125369 (2015) (11 pages).
Zarbo et al., "Immune-related Alopecia (Areata and Universalis) in Cancer Patients Receiving Immune Checkpoint Inhibitors," Br J Dermatol. 176(6):1649-52 (2017).

(Continued)

*Primary Examiner* — Brad Duffy
*Assistant Examiner* — Amber K Faust
(74) *Attorney, Agent, or Firm* — Clark & Elbing LLP; Thomas J. Takara

(57) ABSTRACT

Provided herein are diagnostic and therapeutic methods for the treatment of cancer using polygenic risk scores (PRSs) for dermatological autoimmune diseases. In particular, the invention provides methods for patient selection and methods of treatment.

21 Claims, 32 Drawing Sheets

Specification includes a Sequence Listing.

(56) References Cited

OTHER PUBLICATIONS

International Preliminary Report on Patentability for International Patent Application No. PCT/US2020/017003, mailed Aug. 19, 2021 (11 pages).
International Search Report and Written Opinion for International Patent Application No. PCT/US2020/017003, mailed Jun. 8, 2020 (19 pages).
Barnet, et al., "Abstract LB-121: Exploring the germ-line contribution to exceptional response to PD-1/PD-L1 inhibition in patients with metastatic non-small-cell lung cancer by whole genome sequencing," Cancer Res, 78(13_Supplement):LB-121 (2018).
Galsky et al., "Biological features and clinical outcomes in atezolizumab (atezo)-treated patients (pts) with metastatic urothelial cancer (mUC) of the upper vs lower urinary tract (UTUC vs LTUC)," Annals of Oncology. 29(8):viii321 (Oct. 2018).

\* cited by examiner

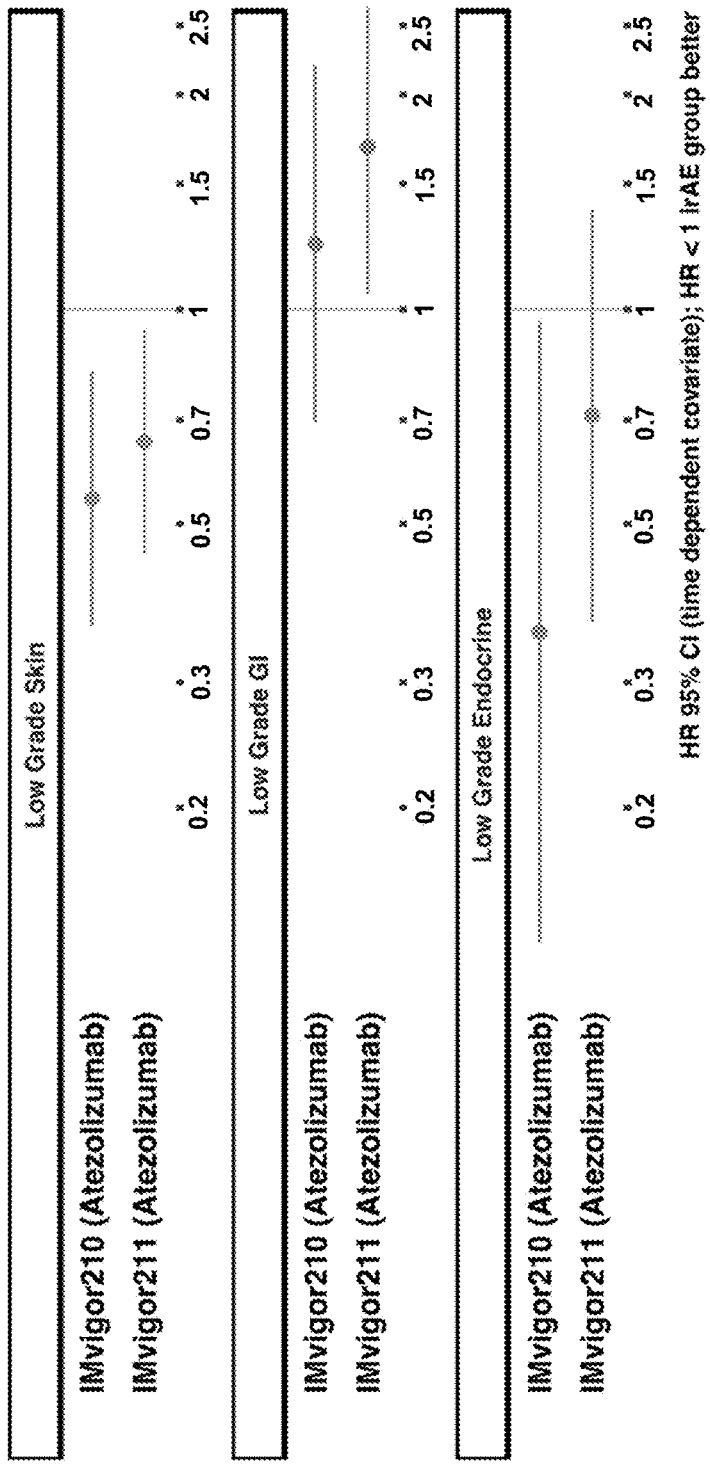

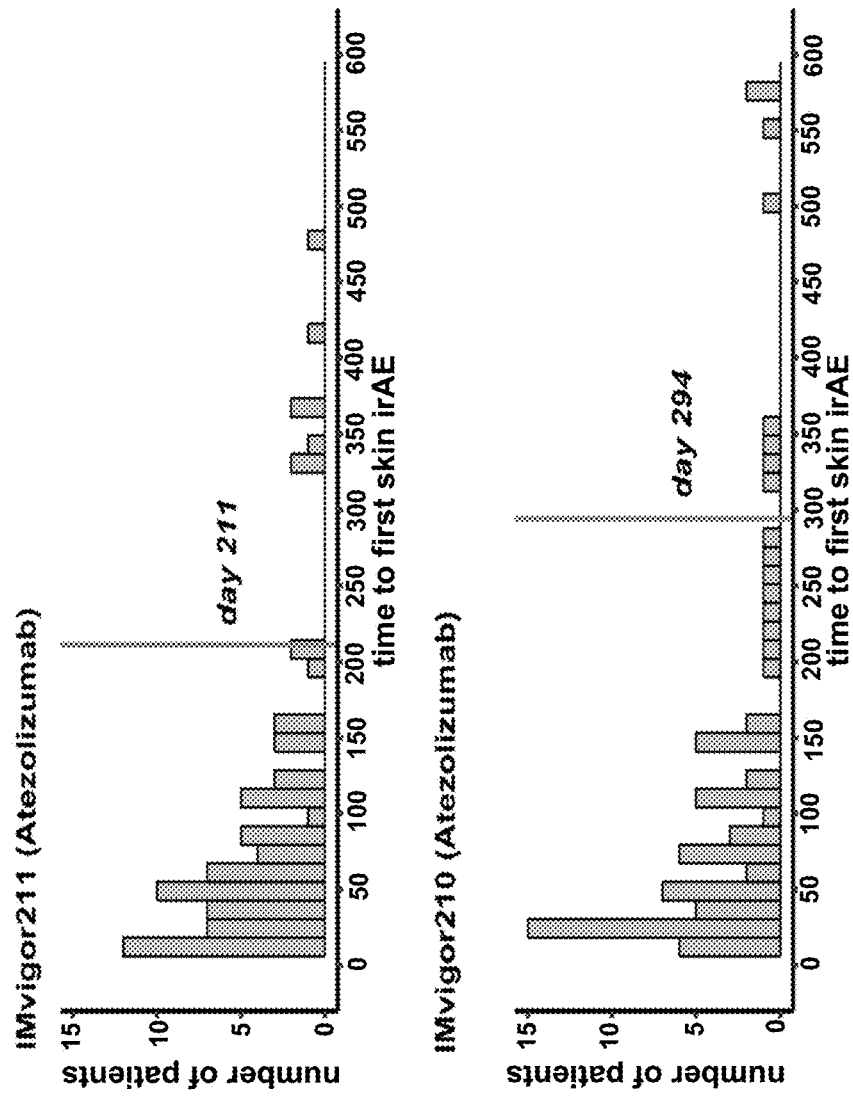

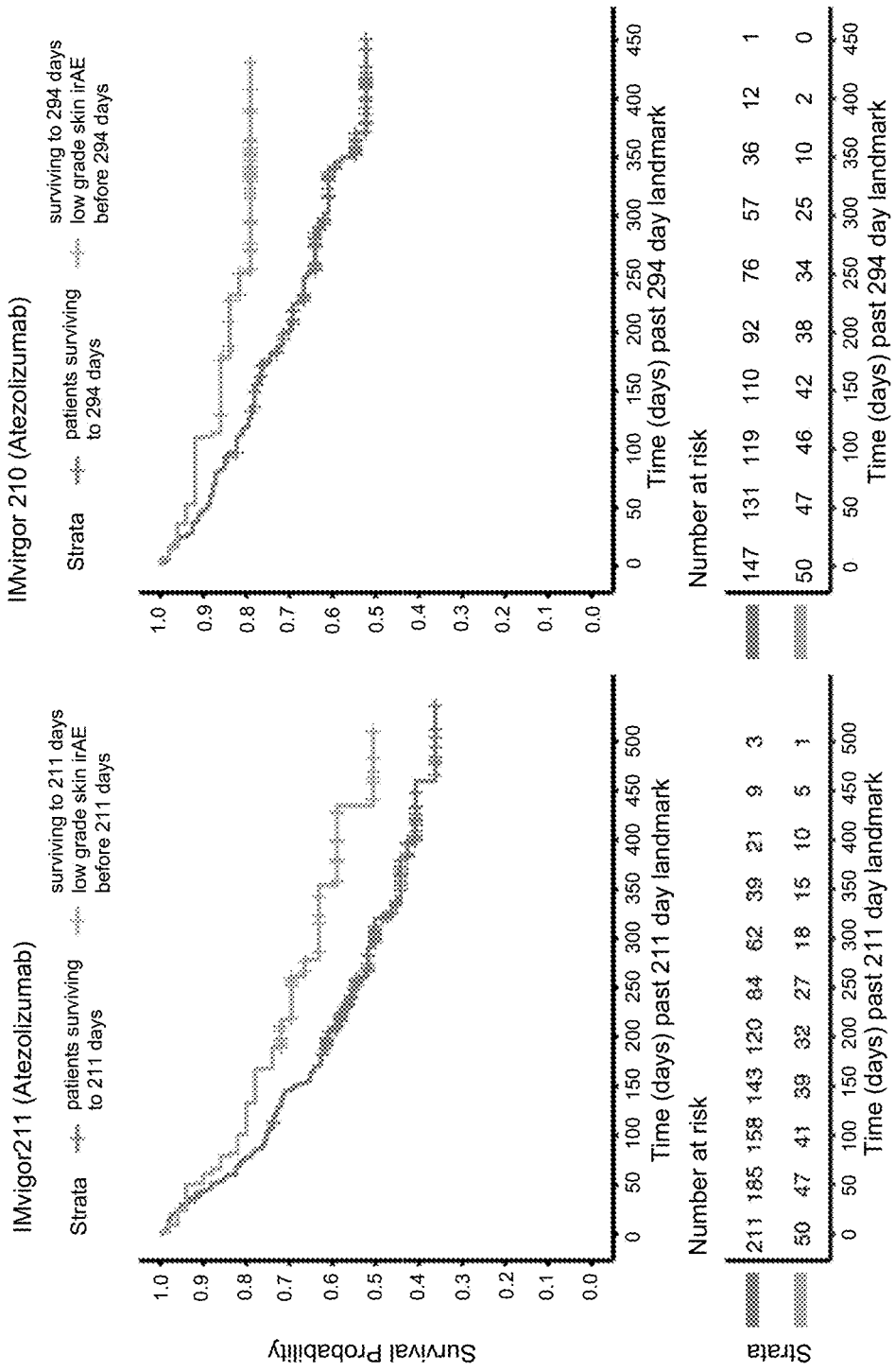

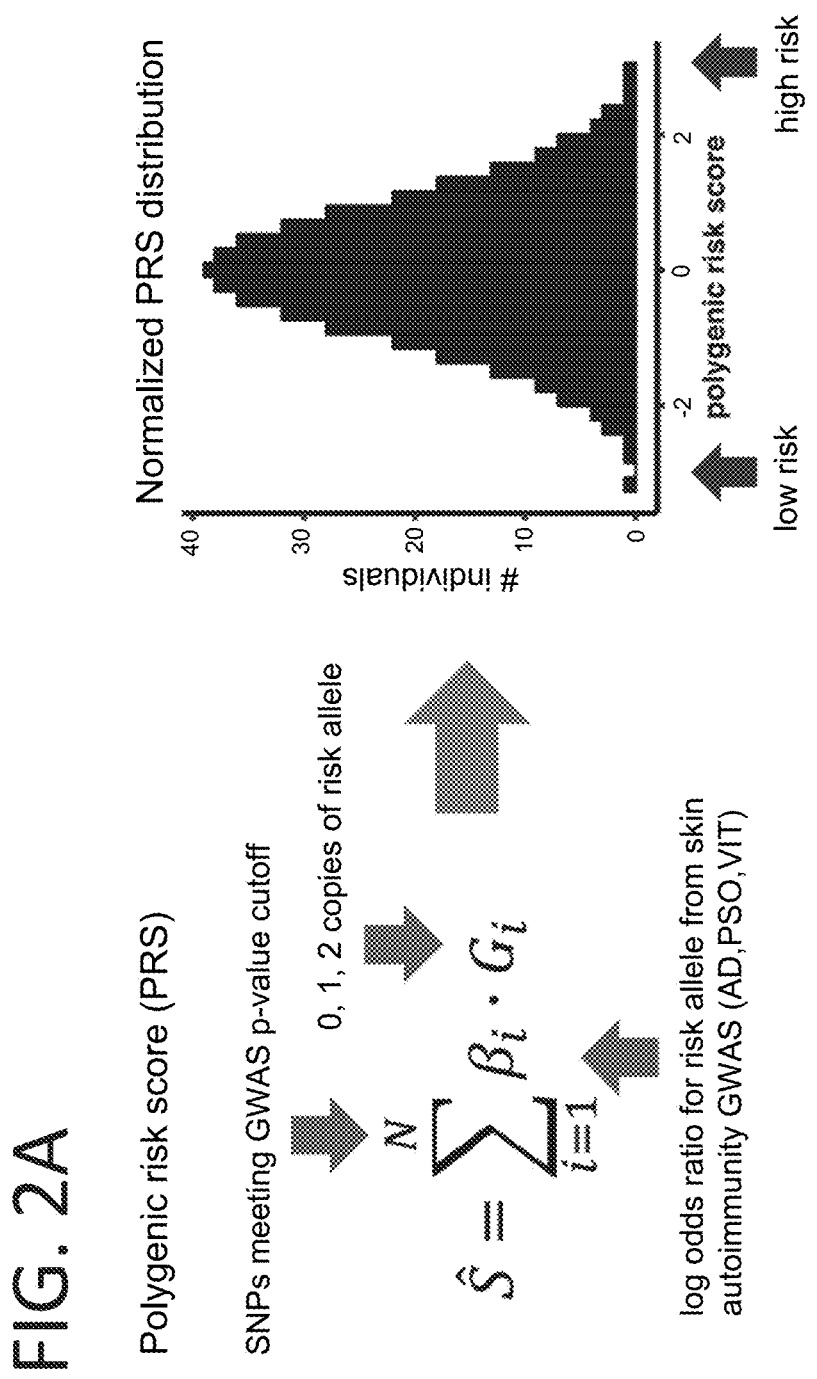

Hazard Ratios Between PRS Subgroups within Trial Arms

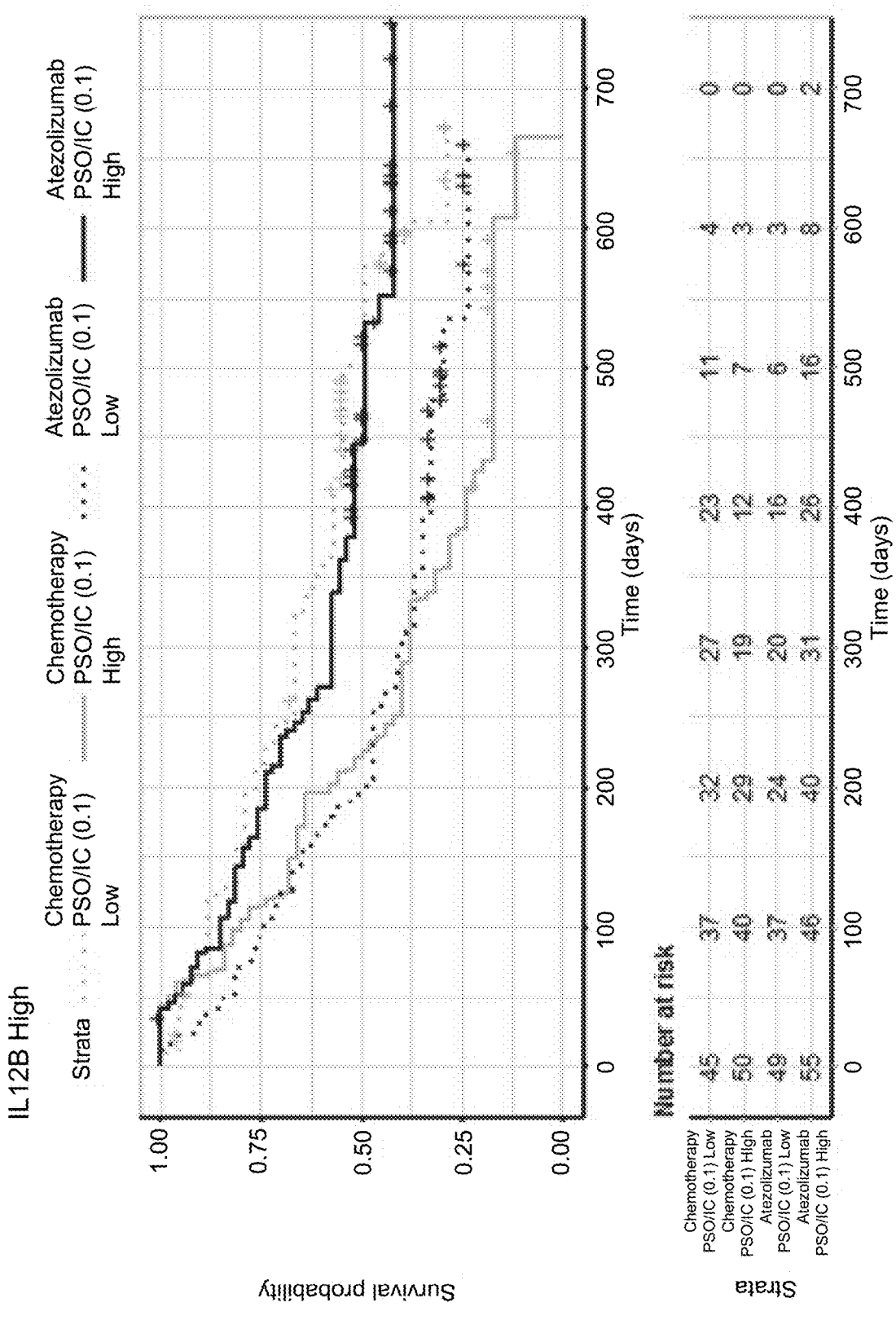
FIG. 18 [cont.]

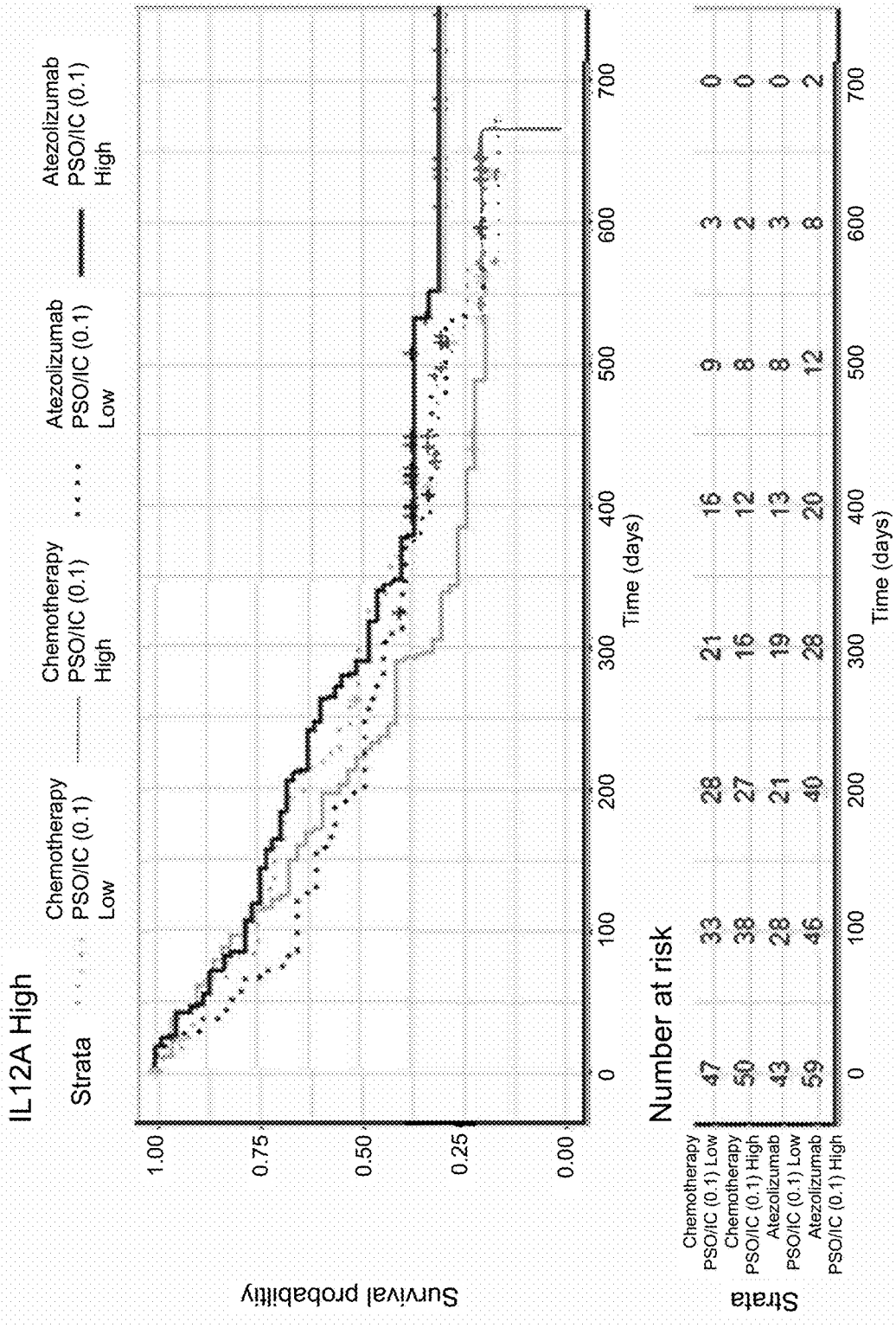
FIG. 18 [cont.]

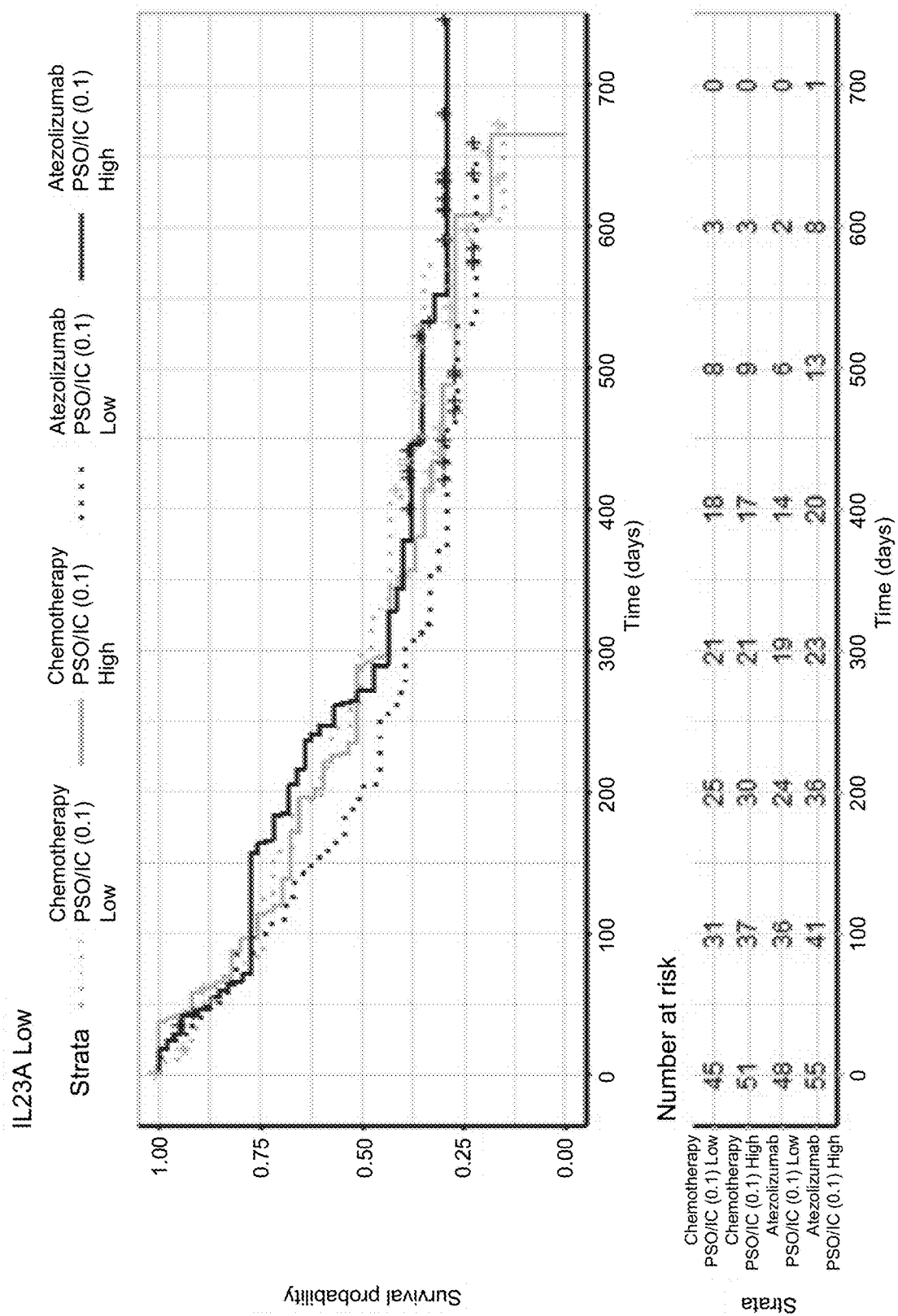
FIG. 18 [cont.]

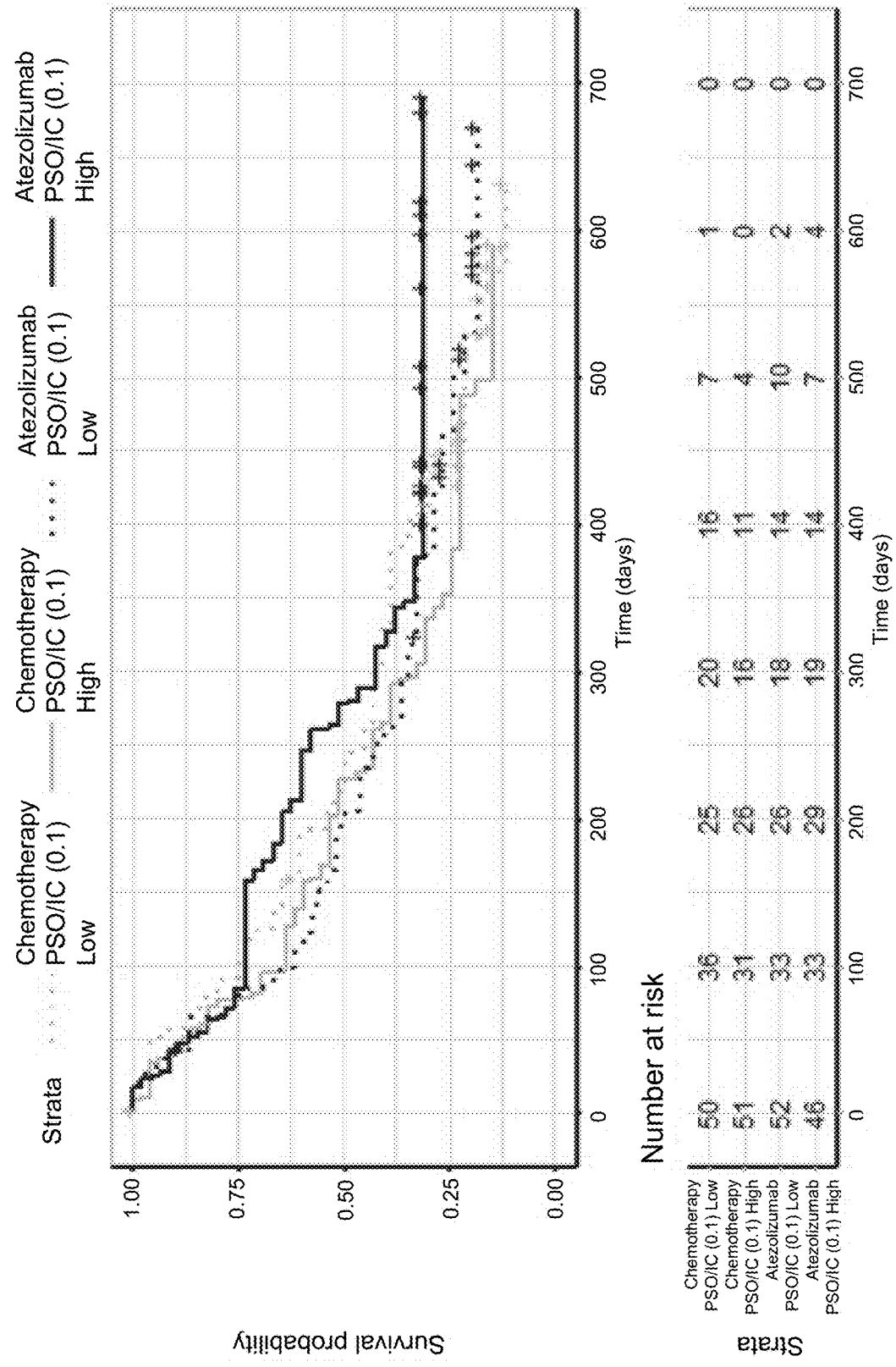
FIG. 18 [cont.]

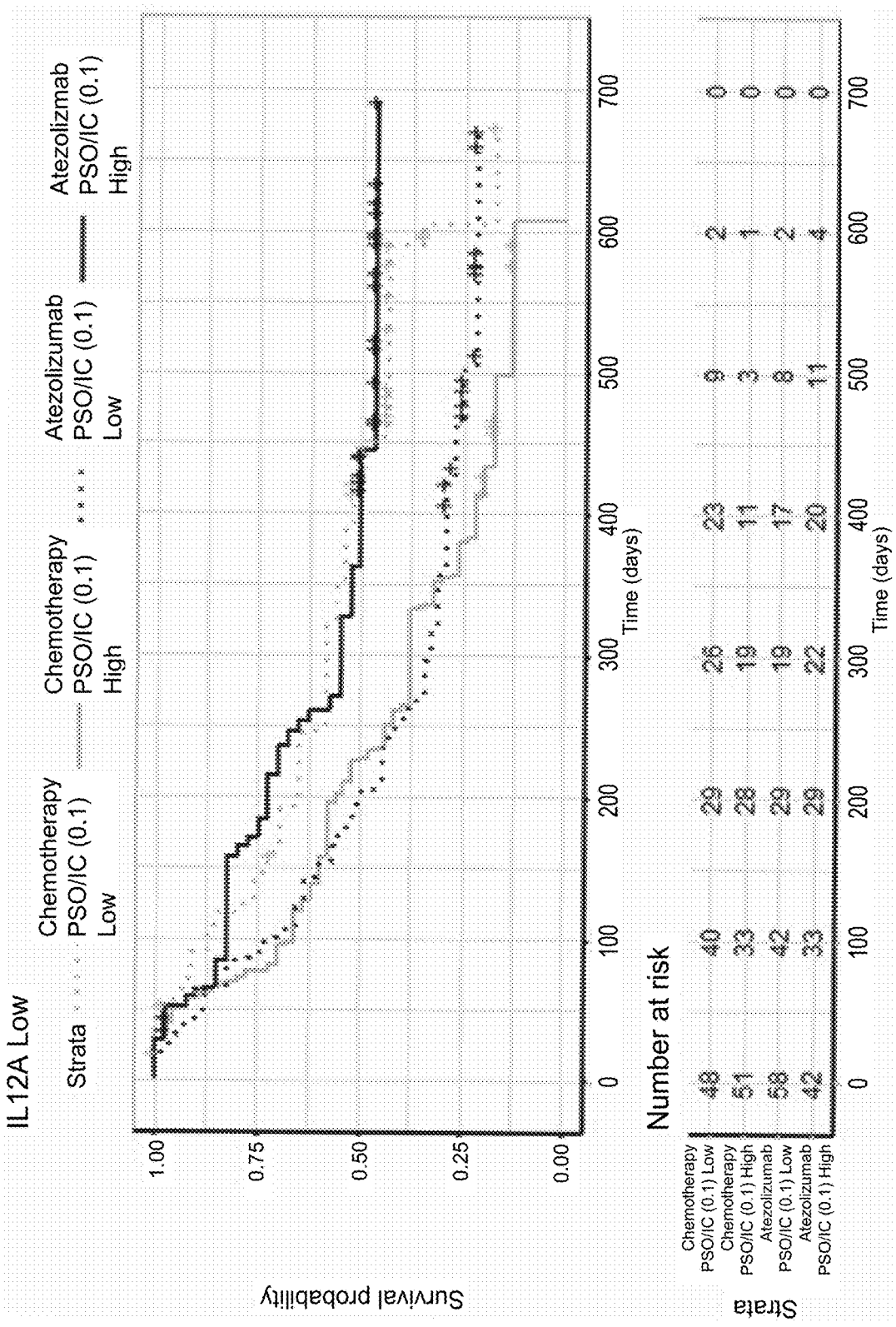
FIG. 18 [cont.]

DIAGNOSTIC AND THERAPEUTIC METHODS FOR CANCER

SEQUENCE LISTING

The instant application contains a Sequence Listing which has been submitted electronically in ASCII format and is hereby incorporated by reference in its entirety. Said ASCII copy, created on Aug. 5, 2021, is named 50474-192002_Sequence_Listing_8_5_21_ST25 and is 24,440 bytes in size.

FIELD OF THE INVENTION

Provided herein are diagnostic and therapeutic methods for the treatment of cancer using polygenic risk scores (PRSs) for dermatological autoimmune diseases. In particular, the invention provides methods for patient selection and methods of treatment.

BACKGROUND

Cancer remains one of the most deadly threats to human health. In the U.S., cancer affects more than 1.7 million new patients each year and is the second leading cause of death after heart disease, accounting for approximately 1 in 4 deaths. It is also predicted that cancer may surpass cardiovascular diseases as the number one cause of death within 5 years.

Immune checkpoint inhibition has emerged as a promising treatment for some cancers, including cancers with high unmet need for treatment options, e.g., metastatic urothelial carcinoma (mUC). In healthy tissues, immune checkpoints function in the prevention of autoimmunity by limiting the activity of T-cells. Tumor cells may co-opt this mechanism to escape immune surveillance. Considerable attention has thus been given to therapies that suppress the function of immune checkpoints (e.g., immune checkpoint blockade) in patients having a cancer. A particular immune checkpoint protein of interest is programmed cell death protein-1 (PD-1 or CD279), which acts to limit the activity of T-cells in peripheral tissues. Blockade of PD-1 by a monoclonal antibody specific for PD-1 or its ligands, programmed death-ligand 1 (PD-L1; CD274) and programmed death-ligand 2 (PD-L2; CD273), has been shown to elicit durable anti-tumor responses in a subset of patients undergoing treatment for cancer.

Immune checkpoint inhibition has been associated with on-target toxicities that are referred to as immune-related adverse events (irAEs). Recent studies have observed a correlation between the occurrence of dermatological irAEs and increased overall survival (OS) under immune checkpoint inhibitor therapy. This correlation suggests that predisposition to dermatological autoimmune conditions may positively affect outcomes for patients treated with immune checkpoint blockade. However, irAEs occur only after immune checkpoint blockade therapy has been initiated.

Thus, there exists an unmet need for diagnostic approaches that enable the use of a patient's genetic predisposition to predict a favorable outcome from treatment with an immune checkpoint inhibitor.

SUMMARY OF THE INVENTION

The present invention provides diagnostic and therapeutic methods for treating an individual having a cancer.

In one aspect, the disclosure features a method of identifying an individual having a cancer who may benefit from a treatment comprising an immune checkpoint inhibitor, the method comprising determining a polygenic risk score (PRS) for one or more of vitiligo, psoriasis, and atopic dermatitis from a sample from the individual, wherein (a) a PRS for vitiligo that is above a vitiligo reference PRS identifies the individual as one who may benefit from a treatment comprising an immune checkpoint inhibitor; (b) a PRS for psoriasis that is above a psoriasis reference PRS identifies the individual as one who may benefit from a treatment comprising an immune checkpoint inhibitor; or (c) a PRS for atopic dermatitis that is below an atopic dermatitis reference PRS identifies the individual as one who may benefit from a treatment comprising an immune checkpoint inhibitor.

In another aspect, the disclosure features a method for selecting a therapy for an individual having a cancer, the method comprising determining a PRS for vitiligo or psoriasis from a sample from the individual, wherein a PRS for vitiligo that is above a vitiligo reference PRS or a PRS for psoriasis that is above a psoriasis reference PRS identifies the individual as one who may benefit from a treatment comprising an immune checkpoint inhibitor.

In some aspects, the PRS for vitiligo determined from the sample is above the vitiligo reference PRS or the PRS for psoriasis determined from the sample is above the psoriasis reference PRS, and the method further comprises administering to the individual an effective amount of an immune checkpoint inhibitor. In some aspects, the PRS for vitiligo determined from the sample is below the vitiligo reference PRS or the PRS for psoriasis determined from the sample is below the psoriasis reference PRS.

In another aspect, the disclosure features a method for selecting a therapy for an individual having a cancer, the method comprising determining a PRS for atopic dermatitis from a sample from the individual, wherein a PRS for atopic dermatitis from the sample that is below an atopic dermatitis reference PRS identifies the individual as one who may benefit from a treatment comprising an immune checkpoint inhibitor.

In some aspects, the PRS for atopic dermatitis determined from the sample is below the atopic dermatitis reference PRS, and the method further comprises administering to the individual an effective amount of an immune checkpoint inhibitor. In some aspects, the PRS for atopic dermatitis determined from the sample is above the atopic dermatitis reference PRS. In some aspects, the PRS for vitiligo determined from the sample is above the vitiligo reference PRS and the PRS for psoriasis determined from the sample is above the psoriasis reference PRS. In some aspects, the PRS for vitiligo determined from the sample is above the vitiligo reference PRS and the PRS for atopic dermatitis determined from the sample is below the atopic dermatitis reference PRS. In some aspects, the PRS for psoriasis determined from the sample is above the psoriasis reference PRS and the PRS for atopic dermatitis determined from the sample is below the atopic dermatitis reference PRS. In some aspects, the PRS for vitiligo determined from the sample is above the vitiligo reference PRS; the PRS for psoriasis determined from the sample is above the psoriasis reference PRS; and the PRS for atopic dermatitis determined from the sample is below the atopic dermatitis reference PRS.

In another aspect, the disclosure features a method of treating an individual having a cancer, the method comprising (a) determining a PRS for one or more of vitiligo, psoriasis, and atopic dermatitis from a sample from the individual, wherein (i) the PRS for vitiligo from the sample is above a vitiligo reference PRS; (ii) the PRS for psoriasis from the sample is above a psoriasis reference PRS; or (iii) the PRS for atopic dermatitis from the sample is below an atopic dermatitis reference PRS; and (b) administering an effective amount of an immune checkpoint inhibitor to the individual.

In another aspect, the disclosure features a method of treating an individual having a cancer, the method comprising administering an immune checkpoint inhibitor to the individual who has been determined to: (a) have a PRS for vitiligo that is above a vitiligo reference PRS; (b) have a PRS for psoriasis that is above a psoriasis reference PRS; or (c) have a PRS for atopic dermatitis that is below an atopic dermatitis reference PRS.

In some aspects, the vitiligo, psoriasis, or atopic dermatitis reference PRS is a PRS in a reference population of individuals having the cancer, the population of individuals consisting of a first subset of individuals who have been treated with an immune checkpoint inhibitor therapy and a second subset of individuals who have been treated with a non-immune checkpoint inhibitor therapy, wherein the non-immune checkpoint inhibitor therapy does not comprise an immune checkpoint inhibitor. In some aspects, the vitiligo, psoriasis, or atopic dermatitis reference PRS significantly separates each of the first and second subsets of individuals based on a significant difference in responsiveness to treatment with the immune checkpoint inhibitor therapy relative to responsiveness to treatment with the non-immune checkpoint inhibitor therapy. In some aspects, responsiveness to treatment is an increase in overall survival (OS).

In some aspects, the vitiligo, psoriasis, or atopic dermatitis reference PRS is a pre-assigned PRS. In some aspects, the vitiligo reference PRS is the median PRS for vitiligo in the reference population. In some aspects, the psoriasis reference PRS is the median PRS for psoriasis in the reference population. In some aspects, the atopic dermatitis reference PRS is the median PRS for atopic dermatitis in the reference population.

In some aspects, (a) the PRS for vitiligo, psoriasis, or atopic dermatitis of the sample from the individual or (b) the PRS for vitiligo, psoriasis, or atopic dermatitis of a sample from an individual in the reference population, is calculated using the equation:

$$\hat{S} = \sum_{i=1}^{M} \beta_i \cdot G_i$$

wherein (i) $\hat{S}$ is the PRS for vitiligo, psoriasis, or atopic dermatitis; (ii) M is the number of risk alleles detected in the sample, wherein a risk allele is identified as a SNP having a p-value at or below a given p-value cutoff in a genome-wide association study (GWAS) for vitiligo, psoriasis, or atopic dermatitis; (iii) i represents the index of a given SNP; (iv) $\beta_i$ is the log odds ratio of the ith SNP; and (v) $G_i=\{0,1,2\}$ is the number of copies of the SNP in the sample from the individual.

In some aspects, the risk alleles are identified in the sample by whole-genome sequencing. In some aspects, the risk alleles identified in the GWAS for vitiligo, psoriasis, or atopic dermatitis do not include SNPs in the HLA loci.

In some aspects, the GWAS is a GWAS for vitiligo. In some aspects, the p-value cutoff is $1\times10^{-8}$ and the GWAS identifies 79 risk alleles. In some aspects, the p-value cutoff is $1\times10^{-7}$ and the GWAS identifies 100 risk alleles. In some aspects, the p-value cutoff is $1\times10^{-5}$ and the GWAS identifies 282 risk alleles.

In some aspects, the GWAS is a GWAS for psoriasis. In some aspects, the GWAS for psoriasis is the ImmunoChip GWAS. In some aspects, the p-value cutoff is 0.001 and the GWAS identifies 493 risk alleles. In some aspects, the p-value cutoff is 0.01 and the GWAS identifies 1396 risk alleles. In some aspects, the p-value cutoff is 0.1 and the GWAS identifies 6033 risk alleles. In some aspects, the GWAS for psoriasis is the UK BioBank GWAS. In some aspects, the p-value cutoff is $1\times10^{-8}$ and the GWAS identifies 45 risk alleles. In some aspects, the p-value cutoff is $1\times10^{-7}$ and the GWAS identifies 69 risk alleles. In some aspects, the p-value cutoff is $1\times10^{-5}$ and the GWAS identifies 217 risk alleles.

In some aspects, the GWAS is a GWAS for atopic dermatitis. In some aspects, the p-value cutoff is $1\times10^{-8}$ and the GWAS identifies 20 risk alleles.

In some aspects, the methods described herein further comprise assessing one or more properties that are positively associated with the predictive capacity of a PRS for psoriasis from a sample from the tumor of the individual before administration of a treatment comprising an immune checkpoint inhibitor. In some aspects, the property is the presence of detectable PD-L1 staining in tumor-infiltrating immune cells covering ≥1% of the tumor area, as assessed by an immunohistochemistry (IHC) assay. In some aspects, the IHC assay uses the anti-PD-L1 antibody SP142. In some aspects, the property is CD8+ T-effector function that is increased relative to a reference level. In some aspects, increased $CD8^+$ T-effector function is characterized by (a) expression of CD8A that is increased relative to a reference expression level of CD8A; (b) expression of PRF1 that is increased relative to a reference expression level of PRF1; or (c) a T-effector signature score that is increased relative to a reference score. In some aspects, the T-effector signature score is calculated based on the expression of CD8A, GZMA, GZMB, INFG, CXCL9, CXCL10, PRF1 and TBX21. In some aspects, the property is high expression of CXCL2, CCL20, IL23A, or IL12B. In some aspects, the property is low expression of IL12A.

In some aspects, the sample is a whole blood sample, a buccal swab, a plasma sample, a serum sample, a tissue biopsy, or a combination thereof. In some aspects, the sample is a whole blood sample. In some aspects, the sample is an archival sample, a fresh sample, or a frozen sample.

In some aspects, the cancer is selected from the group consisting of a lung cancer, a kidney cancer, a bladder cancer, a breast cancer, a colorectal cancer, an ovarian cancer, a pancreatic cancer, a gastric carcinoma, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, a mycosis fungoides, a Merkel cell cancer, a hematologic malignancy, or a myelodysplastic syndrome (MDS). In some aspects, the bladder cancer is a urothelial carcinoma (UC). In some aspects, the urothelial carcinoma is a metastatic urothelial carcinoma (mUC).

In some aspects, the immune checkpoint inhibitor is a PD-L1 axis binding antagonist. In some aspects, the PD-L1 axis binding antagonist is a PD-L1 binding antagonist, a PD-1 binding antagonist, or a PD-L2 binding antagonist. In some aspects, the PD-L1 axis binding antagonist is a PD-L1 binding antagonist. In some aspects, the PD-L1 binding antagonist inhibits the binding of PD-L1 to one or more of its ligand binding partners. In some aspects, the PD-L1 binding antagonist inhibits the binding of PD-L1 to PD-1. In some aspects, the PD-L1 binding antagonist inhibits the binding of PD-L1 to B7-1. In some aspects, the PD-L1 binding antagonist inhibits the binding of PD-L1 to both PD-1 and B7-1.

In some aspects, the PD-L1 binding antagonist is an anti-PD-L1 antibody. In some aspects, the anti-PD-L1 antibody is selected from the group consisting of atezolizumab (MPDL3280A), YW243.55.S70, MDX-1105, MEDI4736 (durvalumab), and MSB0010718C (avelumab). In some aspects, the anti-PD-L1 antibody is atezolizumab (MPDL3280A).

In some aspects, the PD-1 axis binding antagonist is a PD-1 binding antagonist. In some aspects, the PD-1 binding antagonist inhibits the binding of PD-1 to one or more of its ligand binding partners. In some aspects, the PD-1 binding antagonist inhibits the binding of PD-1 to PD-L1. In some aspects, the PD-1 binding antagonist inhibits the binding of PD-1 to PD-L2. In some aspects, the PD-1 binding antagonist inhibits the binding of PD-1 to both PD-L1 and PD-L2. In some aspects, the PD-1 binding antagonist is an anti-PD-1 antibody. In some aspects, the anti-PD-1 antibody is MDX 1106 (nivolumab), MK-3475 (pembrolizumab), MEDI-0680 (AMP-514), PDR001 (spartalizumab), REGN2810 (cemiplimab), or BGB-108. In some aspects, the PD-1 binding antagonist is an Fc-fusion protein. In some aspects, the Fc-fusion protein is AMP-224.

In some aspects, the PD-1 axis binding antagonist is a PD-L2 binding antagonist. In some aspects, the PD-L2 binding antagonist is an antibody or an immunoadhesin.

In some aspects, the methods described herein further comprise administering to the individual one or more additional therapeutic agents. In some aspects, the one or more additional therapeutic agents comprise an immunomodulatory agent, an anti-neoplastic agent, a chemotherapeutic agent, a growth inhibitory agent, an anti-angiogenic agent, a radiation therapy, a cytotoxic agent, a cellular therapy, or a combination thereof. In some aspects, the one or more additional therapeutic agents comprise an effective amount of an anti-cancer therapy other than an immune checkpoint inhibitor. In some aspects, the anti-cancer therapy is an anti-neoplastic agent, a chemotherapeutic agent, a growth inhibitory agent, an anti-angiogenic agent, a radiation therapy, a cytotoxic agent, or a cellular therapy. In some aspects, the non-immune checkpoint inhibitor is an anti-neoplastic agent, a chemotherapeutic agent, a growth inhibitory agent, an anti-angiogenic agent, a radiation therapy, or a cytotoxic agent. In some aspects, the non-immune checkpoint inhibitor is a chemotherapeutic agent. In some aspects, the chemotherapeutic agent is vinflunine, paclitaxel, or docetaxel.

In some aspects, the treatment comprising an immune checkpoint inhibitor is a monotherapy.

In some aspects of any of the methods described herein, the individual has not been previously treated for the cancer. In some aspects, the individual has not been previously administered an immune checkpoint inhibitor.

In some aspects of any of the methods described herein, the individual is a human.

In another aspect, the disclosure features an immune checkpoint inhibitor for use in treating an individual having a cancer who has been identified as one who may benefit from a treatment comprising an immune checkpoint inhibitor based on (a) a PRS for vitiligo from a sample from the individual that is above a vitiligo reference PRS; (b) a PRS for psoriasis from a sample from the individual that is above a psoriasis reference PRS; or (c) a PRS for atopic dermatitis from a sample from the individual that is below an atopic dermatitis reference PRS.

In another aspect, the disclosure features a use of an immune checkpoint inhibitor in the manufacture of a medicament for treating an individual having a cancer who has been identified as one who may benefit from a treatment comprising an immune checkpoint inhibitor based on (a) a PRS for vitiligo that is above a vitiligo reference PRS; (b) a PRS for psoriasis that is above a psoriasis reference PRS; or (c) a PRS for atopic dermatitis that is below an atopic dermatitis reference PRS.

BRIEF DESCRIPTION OF THE DRAWINGS

FIG. 1B is a graph showing hazard ratios (HRs) with 95% confidence intervals (CIs; thick lines) comparing overall survival (OS) of individuals that experienced low-grade irAEs to OS of individuals that did not experience an irAE.

FIG. 1C is a set of graphs showing the distribution of time to first skin irAE in days. 90% of individuals that experienced skin irAEs lie to the left of the landmark line.

FIG. 1D is a set of Kaplan-Meier survival curves comparing the OS of individuals who experienced or did not experience a dermatological irAE before a defined landmark in the atezolizumab arm of the clinical trials IMvigor210 and IMvigor211.

FIG. 2A is a schematic representation of a method for calculating a polygenic risk score (PRS) based on single-nucleotide polymorphisms (SNPs) identified in a genome-wide association study (GWAS). PRSs were computed for each individual in the biomarker available population of IMvigor211 for the skin autoimmune diseases atopic dermatitis (AD), psoriasis (PSO), and vitiligo (VIT).

DETAILED DESCRIPTION OF THE INVENTION

I. Definitions

Figure 1A:
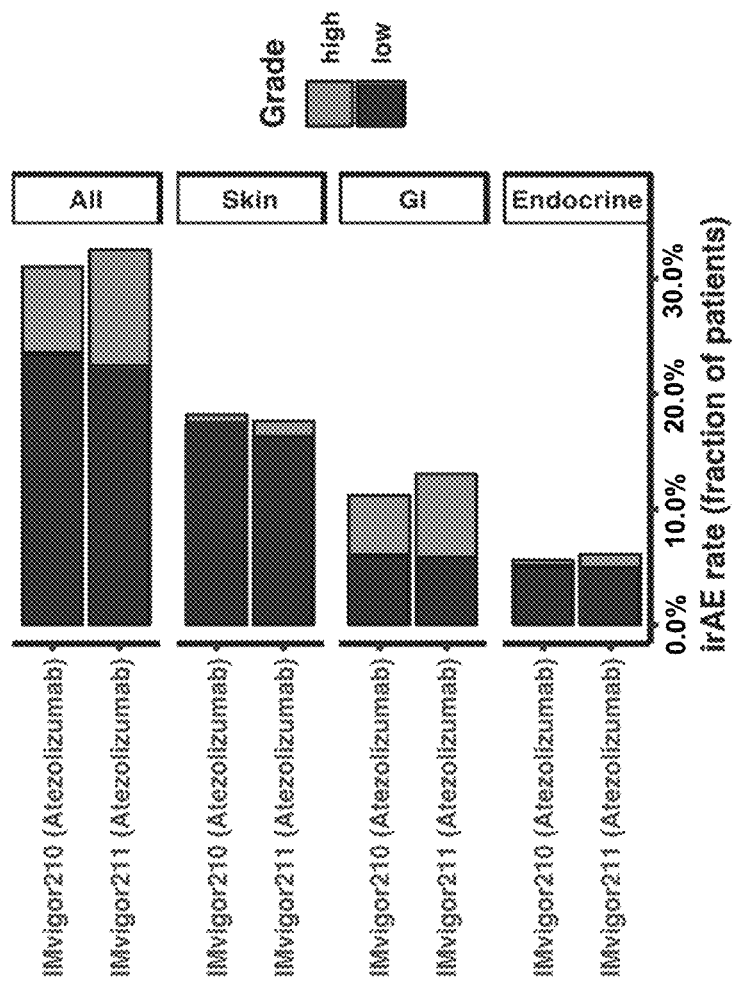
FIG. 1A is a graph showing the rate of high-grade and low-grade immune-related adverse events (irAEs), aggregated by system and organ-based classification in two clinical trials. GI=gastrointestinal. Only irAE categories with occurrence rates >5% are shown.

As used herein, the singular form "a," "an," and "the" includes plural references unless indicated otherwise.

The term "about" as used herein refers to the usual error range for the respective value readily known to the skilled person in this technical field. Reference to "about" a value or parameter herein includes (and describes) aspects that are directed to that value or parameter per se. For example, description referring to "about X" includes description of "X."

It is understood that aspects of the invention described herein include "comprising," "consisting," and "consisting essentially of" aspects.

As used herein, the term "adverse event" or "AE" refers to any unfavorable and unintended sign (including an abnormal laboratory finding), symptom, or disease temporally associated with the use of a medical treatment or procedure that may or may not be considered related to the medical treatment or procedure. Adverse events may be classified by "grade," as defined by the National Cancer Institute Common Terminology Criteria for Adverse Events v5.0 (NIH CTCAE). In some aspects, the AE is a low grade AE, e.g., a Grade 1 or Grade 2 AE. Grade 1 includes AEs that are asymptomatic or have mild symptoms. Grade 2 includes AEs that are moderate and limit age-appropriate instrumental activities of daily living (e.g., preparing meals, shopping for groceries or clothes) and that indicate local or noninvasive intervention. In other instances, the AE is a high grade AE, e.g., a Grade 3, Grade 4, or Grade 5 AE. Grade 3 includes AEs that are severe or medically significant, but not immediately life-threatening, and that indicate hospitalization or prolongation of hospitalization. Grade 4 includes AEs that have life-threatening consequences and indicate urgent intervention. Grade 5 includes AEs that result in or relate to death.

As used herein, the term "immune-related adverse event" or "irAE" refers to an adverse event or "adverse event of special interest" ("AESI"), as classified by the NIH CTCAE, that has a putative immune-related etiology. In some aspects, the irAE is an AESI occurring as a result of immune checkpoint inhibitor therapy. In some aspects, the irAE affects the skin ("dermatological irAE" or "skin irAE"), the gastrointestinal tract ("GI irAE"), or the endocrine system ("endocrine irAE"). Dermatological irAEs include, but are not limited to, "immune-related rash" and "immune-related severe cutaneous reaction." GI irAEs include, but are not limited to, "immune-related hepatitis," "immune-related colitis," and "immune-related pancreatitis." Endocrine irAEs include, but are not limited to, "immune-related hypothyroidism," "immune-related hyperthyroidism," "immune-related adrenal insufficiency," "immune-related diabetes mellitus," and "immune-related hypophysitis." In some aspects, the irAE is a low grade irAE, e.g., a Grade 1 AE (Grade 1 irAE) or Grade 2 AE (Grade 2 irAE).

As used herein, the term "dermatological autoimmune disease" refers to a sign, symptom, or disease having a putative immune-related etiology. In some aspects, the dermatological autoimmune disease is vitiligo, psoriasis, or atopic dermatitis.

As used herein, the term "vitiligo" refers to the physiological condition in mammals that is typically characterized by hypopigmentation, e.g., loss of skin or hair pigment, e.g., loss of melanocytes or of melanocyte function. In some aspects, skin hypopigmentation affects <10% of body surface area (Grade 1 hypopigmentation). In other aspects, skin hypopigmentation affects >10% of body surface area (Grade 2 hypopigmentation).

As used herein, the term "psoriasis" refers to the physiological condition in mammals that is typically characterized by chronic inflammatory dermatosis. In some aspects, psoriasis includes red, scaly skin patches or lesions, e.g., on the scalp, elbows, and knees. In some aspects, psoriasis is caused by abnormal keratinocyte proliferation and infiltration of inflammatory cells into the dermis or epidermis. In some aspects, psoriasis is clinically diagnosed, e.g., in the Immunochip GWAS (Table 1, Tsoi et al., *Nat Genet,* 44:1341-1348, 2012). In other aspects, psoriasis is self-reported, e.g., in the UK BioBank GWAS (Table 1; Bycroft et al., *BioRxiv,* 2017).

As used herein, the term "atopic dermatitis," "AD," or "eczema" refers to the physiological condition in mammals that is typically characterized by skin that becomes itchy, red, inflamed, crusty, thick, scaly, and/or forms blisters. In some aspects, atopic dermatitis is asymptomatic or mild (Grade 1 eczema). In other aspects, atopic dermatitis is moderate (Grade 2 eczema). In still other aspects, atopic dermatitis is severe or medically significant (Grade 3 eczema). In some aspects, the atopic dermatitis is European-American atopic dermatitis. In some aspects, the European-American atopic dermatitis is associated with upregulation of IL-22 (Sanyal et al., *Ann Allergy Asthma Immunol,* 122 (1): 99-110, 2019).

As used herein, the term "polygenic risk score" or "PRS" refers to a numerical value that reflects the number of single-nucleotide polymorphisms (SNPs) associated with an increased likelihood of developing a given pathological state, disease, or condition (e.g., an autoimmune condition, e.g., a dermatological autoimmune condition, e.g., vitiligo, psoriasis, or atopic dermatitis) detected in a sample (e.g., a blood sample (e.g., a whole blood sample, a plasma sample, a serum sample, or a combination thereof), a buccal swab, or a tissue biopsy) obtained from an individual (e.g., an individual at risk of or having a cancer). The PRS can be measured, for example, on a whole genome basis, or on the basis of a subset of the genome (e.g., a predetermined set of loci, e.g., a set of loci in linkage disequilibrium). In some aspects, the predetermined set of loci does not comprise the entire genome. In some aspects, the predetermined set of loci comprise a plurality of loci at which one or more alleles are associated with an increased risk for the given pathological state, disease, or condition. In some aspects, the predetermined set of loci comprise at least about 5 or more, about 10 or more, about 20 or more, about 50 or more, about 100 or more, about 200 or more, about 500 or more, about 1000 or more, about 2000 or more, about 5000 or more, about 10,000 or more, about 15,000 or more, or about 20,000 or more loci.

In some aspects, a PRS that is above a reference PRS (e.g., a reference PRS for vitiligo or psoriasis) identifies an individual as one who may benefit from a treatment comprising an immune checkpoint inhibitor (e.g., a PD-L1 axis binding antagonist, e.g., a PD-L1 binding antagonist, e.g., atezolizumab). In other aspects, a PRS that is the same as below a reference PRS (e.g., a reference PRS for atopic dermatitis) identifies an individual as one who may benefit from a treatment comprising an immune checkpoint inhibitor (e.g., a PD-L1 axis binding antagonist, e.g., a PD-L1 binding antagonist, e.g., atezolizumab).

As used herein, the term "reference polygenic risk score" or "reference PRS" refers to a PRS against which another PRS is compared, e.g., to make a diagnostic, predictive, prognostic, and/or therapeutic determination. For example, the reference PRS may be a PRS in a reference sample, a reference population, and/or a pre-determined value. In some aspects, the reference PRS is a cut-off value that significantly separates a first subset and a second subset of individuals who have been treated with an immune checkpoint inhibitor (e.g., a PD-L1 axis binding antagonist, e.g., a PD-L1 binding antagonist, e.g., atezolizumab) in the same reference population based on a significant difference between an individual's responsiveness to treatment with the immune checkpoint inhibitor, at or above the cut-off value or at or below the cut-off value. In some aspects, the individual's responsiveness to treatment with the immune checkpoint inhibitor (e.g., a PD-L1 axis binding antagonist, e.g., a PD-L1 binding antagonist, e.g., atezolizumab) therapy is significantly improved relative to the individual's responsiveness to treatment with the non-PD-L1 axis binding antagonist therapy at or above the cut-off value. In other aspects, the individual's responsiveness to treatment with the immune checkpoint inhibitor (e.g., a PD-L1 axis binding antagonist, e.g., a PD-L1 binding antagonist, e.g., atezolizumab) is significantly improved relative to the individual's responsiveness to treatment with the non-PD-L1 axis binding antagonist therapy at or below the cut-off value.

In some aspects, a reference PRS is defined as, e.g., the $25^{th}$ percentile, $26^{th}$ percentile, $27^{th}$ percentile, $28^{th}$ percentile, $29^{th}$ percentile, $30^{th}$ percentile, $31^{st}$ percentile, $32^{nd}$ percentile, $33^{rd}$ percentile, $34^{th}$ percentile, $35^{th}$ percentile, $36^{th}$ percentile, $37^{th}$ percentile, $38^{th}$ percentile, $39^{th}$ percentile, $40^{th}$ percentile, $41^{st}$ percentile, $42^{nd}$ percentile, $43^{rd}$ percentile, $44^{th}$ percentile, $45^{th}$ percentile, $46^{th}$ percentile, $47^{th}$ percentile, $48^{th}$ percentile, $49^{th}$ percentile, $50^{th}$ percentile, $51^{st}$ percentile, $52^{nd}$ percentile, $53^{rd}$ percentile, $54^{th}$ percentile, $55^{th}$ percentile, $56^{th}$ percentile, $57^{th}$ percentile, $58^{th}$ percentile, $59^{th}$ percentile, $60^{th}$ percentile, $61^{st}$ percentile, $62^{nd}$ percentile, $63^{rd}$ percentile, $64^{th}$ percentile, $65^{th}$ percentile, $66^{th}$ percentile, $67^{th}$ percentile, $68^{th}$ percentile, $69^{th}$ percentile, $70^{th}$ percentile, $71^{st}$ percentile, $72^{nd}$ percentile, $73^{rd}$ percentile, $74^{th}$ percentile, or $75^{th}$ percentile, of PRSs in the reference population. In some aspects, a reference PRS is defined as the $50^{th}$ percentile of PRSs in the reference population. In some aspects, a reference PRS is defined as the median of PRSs in the reference population.

In some aspects, a PRS determined using methods disclosed herein to be above a reference PRS is used to identify a patient who is predicted to have an increased likelihood of being responsive to treatment with an immune checkpoint inhibitor (e.g., treatment comprising a PD-L1 axis binding antagonist, e.g., an anti-PD-L1 antibody, e.g., atezolizumab). In some aspects, a PRS determined using methods disclosed herein to be below a reference PRS is used to identify a patient who is predicted to have an increased likelihood of being responsive to treatment with an immune checkpoint inhibitor (e.g., treatment comprising a PD-L1 axis binding antagonist, e.g., an anti-PD-L1 antibody, e.g., atezolizumab).

The term "copy number of a gene" or "copy number of an allele" refers to the number of DNA loci in a cell having a particular sequence. Generally, for a given gene or locus, a mammal has two copies of each gene or locus. The copy number can be increased, e.g., by gene amplification or duplication, or reduced by deletion.

As used herein, the terms "tumor mutational burden," "TMB," "tumor mutational burden score," and "TMB score" refer to the level (e.g., number) of an alteration (e.g., one or more alterations, e.g., one or more somatic alterations) per a pre-selected unit (e.g., per megabase) in a pre-determined set of genes (e.g., in the coding regions of the pre-determined set of genes) detected in a tumor tissue sample (e.g., a formalin-fixed and paraffin-embedded (FFPE) tumor sample, an archival tumor sample, a fresh tumor sample, or a frozen tumor sample). The TMB score can be measured, for example, on a whole genome or exome basis, or on the basis of a subset of the genome or exome. In some aspects, the TMB score measured on the basis of a subset of the genome or exome can be extrapolated to determine a whole genome or exome mutation load. In some aspects, a TMB score refers to the level of accumulated somatic mutations within an individual (e.g., an animal (e.g., a human)). The TMB score may refer to accumulated somatic mutations in a patient with cancer (e.g., lung cancer, e.g., NSCLC). In some aspects, a TMB score refers to the accumulated mutations in the whole genome of an individual. In some aspects, a TMB score refers to the accumulated mutations within a particular tissue sample (e.g., tumor tissue sample biopsy, e.g., a lung cancer tumor sample, e.g., an NSCLC tumor sample) collected from an individual.

As used herein, the term "reference TMB score" refers to a TMB score against which another TMB score is compared, e.g., to make a diagnostic, predictive, prognostic, and/or therapeutic determination. For example, the reference TMB score may be a TMB score in a reference sample, a reference population, and/or a pre-determined value. In some instances, the reference TMB score is a cut-off value that significantly separates a first subset of individuals (e.g., patients) who have been treated with an immune checkpoint inhibitor (e.g., a PD-L1 axis binding antagonist, e.g., a PD-L1 binding antagonist, e.g., atezolizumab) in a reference population and a second subset of individuals (e.g., patients) who have been treated with a non-PD-L1 axis binding antagonist therapy that does not comprise an immune checkpoint inhibitor, such as a PD-L1 axis binding antagonist, in the same reference population based on a significant difference between an individual's responsiveness to treatment with the immune checkpoint inhibitor (e.g., a PD-L1 axis binding antagonist, e.g., a PD-L1 binding antagonist, e.g., atezolizumab) and an individual's responsiveness to treatment with the non-PD-L1 axis binding antagonist therapy at or above the cut-off value and/or below the cut-off value. In some instances, the individual's responsiveness to treatment with the immune checkpoint inhibitor (e.g., a PD-L1 axis binding antagonist, e.g., a PD-L1 binding antagonist, e.g., atezolizumab) is significantly improved relative to the individual's responsiveness to treatment with the non-PD-L1 axis binding antagonist therapy at or above the cut-off value. In some instances, the individual's responsiveness to treatment with the non-PD-L1 axis binding antagonist therapy is significantly improved relative to the individual's responsiveness to treatment with the immune checkpoint inhibitor (e.g., a PD-L1 axis binding antagonist, e.g., a PD-L1 binding antagonist, e.g., atezolizumab) below the cut-off value.

The term "somatic mutation" or "somatic alteration" refers to a genetic alteration occurring in the somatic tissues (e.g., cells outside the germline). Examples of genetic alterations include, but are not limited to, point mutations (e.g., the exchange of a single nucleotide for another (e.g., silent mutations, missense mutations, and nonsense mutations)), insertions and deletions (e.g., the addition and/or removal of one or more nucleotides (e.g., indels)), amplifications, gene duplications, copy number alterations (CNAs), rearrangements, and splice variants. The presence of particular mutations can be associated with disease states (e.g., cancer (e.g., a bladder cancer (e.g., UC, e.g., mUC), a kidney cancer (e.g., RCC), a lung cancer (e.g., NSCLC), a liver cancer, an ovarian cancer, a pancreatic cancer (e.g., PDAC), a colorectal cancer, or a breast cancer)).

As used herein, the term "immune checkpoint inhibitor" refers to a therapeutic agent that targets at least one immune checkpoint protein to alter the regulation of an immune response, e.g., down-modulating, inhibiting, up-modulating, or activating an immune response. The term "immune checkpoint blockade" may be used to refer to a therapy comprising an immune checkpoint inhibitor. Immune checkpoint proteins are known in the art and include, without limitation, cytotoxic T-lymphocyte antigen 4 (CTLA-4), programmed cell death 1 (PD-1), programmed cell death ligand 1 (PD-L1), programmed cell death ligand 2 (PD-L2), V-domain Ig suppressor of T cell activation (VISTA), B7-H2, B7-H3, B7-H4, B7-H6, 2B4, ICOS, HVEM, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, LAG-3, BTLA, IDO, OX40, and A2aR. In some aspects, an immune checkpoint protein may be expressed on the surface of an activated T cell. Therapeutic agents that can act as immune checkpoint inhibitors useful in the methods of the present invention, include, but are not limited to, therapeutic agents that target one or more of CTLA-4, PD-1, PD-L1, PD-L2, VISTA, B7-H2, B7-H3, B7-H4, B7-H6, 2B4, ICOS, HVEM, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, LAG-3, BTLA, IDO, OX40, and A2aR. In some aspects, an immune checkpoint inhibitor enhances or suppresses the function of one or more targeted immune checkpoint proteins. In some aspects, the immune checkpoint inhibitor is a PD-L1 axis binding antagonist, such as atezolizumab, as described herein.

The term "PD-1 axis binding antagonist" refers to a molecule that inhibits the interaction of a PD-1 axis binding partner with either one or more of its binding partner, so as to remove T cell dysfunction resulting from signaling on the PD-1 signaling axis—with a result being to restore or enhance T cell function (e.g., proliferation, cytokine production, target cell killing). As used herein, a PD-1 axis binding antagonist includes a PD-1 binding antagonist, a PD-L1 binding antagonist, and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some aspects, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one aspect, a PD-1 binding antagonist reduces the negative co-stimulatory signal mediated by or through cell surface proteins expressed on T lymphocytes mediated signaling through PD-1 so as render a dysfunctional T cell less dysfunctional (e.g., enhancing effector responses to antigen recognition). In some aspects, the PD-1 binding antagonist is an anti-PD-1 antibody. In a specific aspect, a PD-1 binding antagonist is MDX-1106 (nivolumab). In another specific aspect, a PD-1 binding antagonist is MK-3475 (pembrolizumab). In another specific aspect, a PD-1 binding antagonist is AMP-224. In another specific aspect, a PD-1 binding antagonist is MEDI-0680. In another specific aspect, a PD-1 binding antagonist is PDR001 (spartalizumab). In another specific aspect, a PD-1 binding antagonist is REGN2810 (cemiplimab). In another specific aspect, a PD-1 binding antagonist is BGB-108.

The term "PD-L1 binding antagonist" refers to a molecule that decreases, blocks, inhibits, abrogates or interferes with signal transduction resulting from the interaction of PD-L1 with either one or more of its binding partners, such as PD-1 and B7-1. In some aspects, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some aspects, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1 and B7-1. In one aspect, a PD-L1 binding antagonist reduces the negative co-stimulatory signal mediated by or through cell surface proteins expressed on T lymphocytes mediated signaling through PD-L1 so as to render a dysfunctional T cell less dysfunctional (e.g., enhancing effector responses to antigen recognition). In some aspects, a PD-L1 binding antagonist is an anti-PD-L1 antibody. In still another specific aspect, an anti-PD-L1 antibody is MPDL3280A (atezolizumab, marketed as TECENTRIQ™ with a WHO Drug Information (International Nonproprietary Names for Pharmaceutical Substances), Recommended INN: List 74, Vol. 29, No. 3, 2015 (see page 387)). In a specific aspect, an anti-PD-L1 antibody is YW243.55.S70. In another specific aspect, an anti-PD-L1 antibody is MDX-1105. In another specific aspect, an anti PD-L1 antibody is MSB0015718C. In still another specific aspect, an anti-PD-L1 antibody is MEDI4736.

The term "PD-L2 binding antagonist" refers to a molecule that decreases, blocks, inhibits, abrogates or interferes with signal transduction resulting from the interaction of PD-L2 with either one or more of its binding partners, such as PD-1. In some aspects, a PD-L2 binding antagonist is a molecule that inhibits the binding of PD-L2 to one or more of its binding partners. In a specific aspect, the PD-L2 binding antagonist inhibits binding of PD-L2 to PD-1. In some aspects, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one aspect, a PD-L2 binding antagonist reduces the negative co-stimulatory signal mediated by or through cell surface proteins expressed on T lymphocytes mediated signaling through PD-L2 so as render a dysfunctional T cell less dysfunctional (e.g., enhancing effector responses to antigen recognition). In some aspects, a PD-L2 binding antagonist is an immunoadhesin.

The term "small molecule" refers to any molecule with a molecular weight of about 2000 daltons or less, preferably of about 500 daltons or less.

The term "antibody" herein is used in the broadest sense and encompasses various antibody structures, including but not limited to monoclonal antibodies, polyclonal antibodies, multispecific antibodies (e.g., bispecific antibodies), and antibody fragments (e.g., bis-Fabs) so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to bis-Fabs; Fv; Fab; Fab, Fab'-SH; F(ab')$_2$; diabodies; linear antibodies; single-chain antibody molecules (e.g., scFv, ScFab); and multispecific antibodies formed from antibody fragments.

A "single-domain antibody" refers to an antibody fragment comprising all or a portion of the heavy chain variable domain or all or a portion of the light chain variable domain of an antibody. In certain aspects, a single-domain antibody is a human single-domain antibody (see, e.g., U.S. Pat. No. 6,248,516 B1). Examples of single-domain antibodies include but are not limited to a VHH.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90:6444-6448 (1993). Triabodies and tetrabodies are also described in Hudson et al., *Nat. Med.* 9:129-134 (2003).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of antibodies are called α, δ, ε, γ, and μ, respectively.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain aspects, such a monoclonal antibody typically includes an antibody comprising a polypeptide sequence that binds a target, wherein the target-binding polypeptide sequence was obtained by a process that includes the selection of a single target-binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target-binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target-binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature* 256:495-97 (1975); Hongo et al., *Hybridoma* 14 (3): 253-260 (1995), Harlow et al., *Antibodies: A Laboratory Manual* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352:624-628 (1991); Marks et al., *J. Mol. Biol.* 222:581-597 (1992); Sidhu et al., *J. Mol. Biol.* 338 (2): 299-310 (2004); Lee et al., *J. Mol. Biol.* 340 (5): 1073-1093 (2004); Fellouse, *Proc. Natl. Acad. Sci. USA* 101 (34): 12467-12472 (2004); and Lee et al., *J. Immunol. Methods* 284 (1-2): 119-132 (2004)), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg et al., *Intern. Rev. Immunol.* 13:65-93 (1995)).

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues. Human antibodies can be produced using various techniques known in the art, including phage-display libraries. Hoogenboom and Winter. *J. Mol. Biol.* 227:381, 1991; Marks et al. *J. Mol. Biol.* 222:581, 1991. Also available for the preparation of human monoclonal antibodies are methods described in Cole et al. *Monoclonal Antibodies and Cancer Therapy*, Alan R. Liss, p. 77 (1985); Boerner et al. *J. Immunol.*, 147 (1): 86-95, 1991. See also van Dijk and van de Winkel. *Curr. Opin. Pharmacol.* 5:368-74, 2001. Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al. *Proc. Natl. Acad. Sci. USA.* 103:3557-3562, 2006 regarding human antibodies generated via a human B-cell hybridoma technology.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. *Sequences of Proteins of Immunological Interest*, Fifth Edition, NIH Publication 91-3242, Bethesda MD (1991), vols. 1-3. In one aspect, for the VL, the subgroup is subgroup kappa I as in Kabat et al. supra. In one aspect, for the VH, the subgroup is subgroup III as in Kabat et al. supra.

A "humanized" antibody refers to a chimeric antibody comprising amino acid residues from non-human HVRs and amino acid residues from human FRs. In certain aspects, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3).

The terms "anti-PD-L1 antibody" and "an antibody that binds to PD-L1" refer to an antibody that is capable of binding PD-L1 with sufficient affinity such that the antibody is useful as a diagnostic and/or therapeutic agent in targeting PD-L1. In one aspect, the extent of binding of an anti-PD-L1 antibody to an unrelated, non-PD-L1 protein is less than about 10% of the binding of the antibody to PD-L1 as measured, for example, by a radioimmunoassay (RIA). In some aspects, an anti-PD-L1 antibody binds to an epitope of PD-L1 that is conserved among PD-L1 from different species. In another aspect, an anti-PD-L1 antibody is MPDL3280A (atezolizumab, marketed as TECENTRIQ™ with a WHO Drug Information (International Nonproprietary Names for Pharmaceutical Substances), Recommended INN: List 74, Vol. 29, No. 3, 2015 (see page 387)).

The terms "anti-PD-1 antibody" and "an antibody that binds to PD-1" refer to an antibody that is capable of binding PD-1 with sufficient affinity such that the antibody is useful as a diagnostic and/or therapeutic agent in targeting PD-1. In one aspect, the extent of binding of an anti-PD-1 antibody to an unrelated, non-PD-1 protein is less than about 10% of the binding of the antibody to PD-1 as measured, for example, by a radioimmunoassay (RIA). In certain aspects, an anti-PD-1 antibody binds to an epitope of PD-1 that is conserved among PD-1 from different species.

A "blocking" antibody or an "antagonist" antibody is one which inhibits or reduces biological activity of the antigen it binds. In some aspects, blocking antibodies or antagonist antibodies substantially or completely inhibit the biological activity of the antigen.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art.

As used herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In some aspects, the extent of binding of an antibody to an unrelated target is less than about 10% of the binding of the antibody to the target as measured, e.g., by a radioimmunoassay (RIA). In some aspects, an antibody that specifically binds to a target has a dissociation constant ($K_D$) of ≤1 µM, ≤100 nM, ≤10 nM, ≤1 nM, or ≤0.1 nM. In some aspects, an antibody specifically binds to an epitope on a protein that is conserved among the protein from different species. In other aspects, specific binding can include, but does not require exclusive binding.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "biomarker" as used herein refers to an indicator, e.g., predictive, diagnostic, and/or prognostic, which can be detected in a sample, e.g., a single-nucleotide polymorphism (SNP), or derived therefrom (e.g., a PRS). In some aspects, a biomarker is a genetic locus, a collection of genetic loci, or a collective number of mutations/alterations (e.g., somatic mutations) in a collection of genes. Biomarkers include, but are not limited to, polynucleotides (e.g., DNA and/or RNA), polynucleotide alterations (e.g., polynucleotide copy number alterations, e.g., DNA copy number alterations), polypeptides, polypeptide and polynucleotide modifications (e.g., post-translational modifications), carbohydrates, and/or glycolipid-based molecular markers. The biomarker may serve as an indicator of the likelihood of developing a given pathological state, disease, or condition (e.g., an autoimmune condition, e.g., a dermatological autoimmune condition, e.g., vitiligo, psoriasis, or atopic dermatitis), or of developing a particular subtype of a disease or disorder (e.g., cancer) characterized by certain, molecular, pathological, histological, and/or clinical features (e.g., responsiveness to therapy including an immune checkpoint inhibitor).

The term "sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, plasma, serum, blood-derived cells, urine, cerebro-spinal fluid, saliva, buccal swab, sputum, tears, perspiration, mucus, tumor lysates, and tissue culture medium, tissue extracts such as homogenized tissue, tumor tissue, cellular extracts, and combinations thereof. The sample may be an archival sample, a fresh sample, or a frozen sample. In some instances, the sample is a buccal swab, whole blood sample, a plasma sample, a serum sample, or a combination thereof.

A "tumor cell" as used herein, refers to any tumor cell present in a tumor or a sample thereof. Tumor cells may be distinguished from other cells that may be present in a tumor sample, for example, stromal cells and tumor-infiltrating immune cells, using methods known in the art and/or described herein.

A "reference sample," "reference cell," "reference tissue," "control sample," "control cell," or "control tissue," as used herein, refers to a sample, cell, tissue, standard, or level that is used for comparison purposes.

"Individual response" or "response" can be assessed using any endpoint indicating a benefit to the individual, including, without limitation, (1) inhibition, to some extent, of disease progression (e.g., cancer progression), including slowing down or complete arrest; (2) a reduction in tumor size; (3) inhibition (i.e., reduction, slowing down, or complete stopping) of cancer cell infiltration into adjacent peripheral organs and/or tissues; (4) inhibition (i.e. reduction, slowing down, or complete stopping) of metastasis; (5) relief, to some extent, of one or more symptoms associated with the disease or disorder (e.g., cancer); (6) increase or extension in the length of survival, including overall survival and progression free survival; and/or (7) decreased mortality at a given point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In some aspects, such benefit includes any one or more of: extending survival (including overall survival and/or progression-free survival); resulting in an objective response (including a complete response or a partial response); or improving signs or symptoms of cancer.

An "objective response" refers to a measurable response, including complete response (CR) or partial response (PR). In some aspects, the "objective response rate (ORR)" refers to the sum of complete response (CR) rate and partial response (PR) rate. By "best confirmed objective response" is meant the best objective response observed for a subject from the group of complete response (CR), partial response (PR), stable disease (SR), and progressive disease (PD), listed from best to worst.

By "complete response" or "CR" is intended the disappearance of all signs of cancer (e.g., disappearance of all target lesions) in response to treatment. This does not always mean the cancer has been cured.

"Sustained response" refers to the sustained effect on reducing tumor growth after cessation of a treatment. For example, the tumor size may be the same size or smaller as compared to the size at the beginning of the medicament administration phase. In some aspects, the sustained response has a duration at least the same as the treatment duration, at least 1.5×, 2.0×, 2.5×, or 3.0× length of the treatment duration, or longer.

As used herein, "reducing or inhibiting cancer relapse" means to reduce or inhibit tumor or cancer relapse or tumor or cancer progression. As disclosed herein, cancer relapse and/or cancer progression include, without limitation, cancer metastasis.

As used herein, "partial response" or "PR" refers to a decrease in the size of one or more tumors or lesions, or in the extent of cancer in the body, in response to treatment. For example, in some aspects, PR refers to at least a 30% decrease in the sum of the longest diameters (SLD) of target lesions, taking as reference the baseline SLD.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

The term "survival" refers to the patient remaining alive, and includes overall survival as well as progression-free survival.

As used herein, "progression-free survival" or "PFS" refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" or "OS" refers to the percentage of individuals in a group who are likely to be alive after a particular duration of time.

By "extending survival" is meant increasing overall survival or progression-free survival in a treated patient relative to an untreated patient (i.e. relative to a patient not treated with the medicament), or relative to a patient who has been treated with a non-immune checkpoint inhibitor therapy, wherein the patient having extended survival (e.g., overall survival) has a PRS for vitiligo that is above a vitiligo reference PRS; a PRS for psoriasis that is above a psoriasis reference PRS; and/or a PRS for atopic dermatitis that is below an atopic dermatitis reference PRS.

As used herein, "hazard ratio" or "HR" is a statistical definition for rates of events. For the purpose of the invention, hazard ratio is defined as representing the probability of an event (e.g., PFS or OS) in the experimental (e.g., treatment) group/arm divided by the probability of an event in the control group/arm at any specific point in time. An HR with a value of 1 indicates that the relative risk of an endpoint (e.g., death) is equal in both the "treatment" and "control" groups; a value greater than 1 indicates that the risk is greater in the treatment group relative to the control group; and a value less than 1 indicates that the risk is greater in the control group relative to the treatment group. "Hazard ratio" in progression-free survival analysis (i.e., PFS HR) is a summary of the difference between two progression-free survival curves, representing the reduction in the risk of death on treatment compared to control, over a period of follow-up. "Hazard ratio" in overall survival analysis (i.e., OS HR) is a summary of the difference between two overall survival curves, representing the reduction in the risk of death on treatment compared to control, over a period of follow-up.

The word "label" when used herein refers to a compound or composition that is conjugated or fused directly or indirectly to a reagent such as a polynucleotide probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable. The term is intended to encompass direct labeling of a probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

An "effective amount" of a compound, for example, an immune checkpoint inhibitor (e.g., a PD-L1 axis binding antagonist, e.g., a PD-L1 binding antagonist, e.g., atezolizumab) or a composition (e.g., pharmaceutical composition) thereof, is at least the minimum amount required to achieve the desired therapeutic or prophylactic result, such as a measurable improvement or prevention of a particular disorder (e.g., a cell proliferative disorder, e.g., cancer). An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications, and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

A "disorder" is any condition that would benefit from treatment including, but not limited to, chronic and acute disorders or diseases including those pathological conditions which predispose the mammal to the disorder in question. In one aspect, the disorder is a cancer.

The terms "cancer" and "cancerous" refer to or describe the physiological condition in mammals that is typically characterized by unregulated cell growth/proliferation. Aspects of cancer include solid tumor cancers and non-solid tumor cancers. Solid cancer tumors include, but are not limited to a bladder cancer, a melanoma, a breast cancer, a colorectal cancer, a lung cancer, a head and neck cancer, a kidney cancer, an ovarian cancer, a pancreatic cancer, or a prostate cancer, or metastatic forms thereof. In some aspects, the cancer is a bladder cancer. Further aspects of bladder cancer include urothelial carcinoma (UC), muscle invasive bladder cancer (MIBC), and non-muscle invasive bladder cancer (NMIBC). In some aspects, the bladder cancer is a metastatic urothelial carcinoma (mUC). In some aspects, the cancer is a breast cancer. Further aspects of breast cancer include a hormone receptor-positive (HR+) breast cancer, e.g., an estrogen receptor-positive (ER+) breast cancer, a progesterone receptor-positive (PR+) breast cancer, or an ER+/PR+ breast cancer. Other aspects of breast cancer include a HER2-positive (HER2+) breast cancer. Yet other aspects of breast cancer include a triple-negative breast cancer (TNBC). In some aspects, the breast cancer is an early breast cancer. In some aspects, the cancer is a lung cancer. Further aspects of lung cancer include an epidermal growth factor receptor-positive (EGFR+) lung cancer. Other aspects of lung cancer include an epidermal growth factor receptor-negative (EGFR−) lung cancer. Yet other aspects of lung cancer include a non-small cell lung cancer, e.g., a squamous lung cancer or a non-squamous lung cancer. Other aspects of lung cancer include a small cell lung cancer. In some aspects, the cancer is a head and neck cancer. Further aspects of head and neck cancer include a squamous cell carcinoma of the head & neck (SCCHN). In some aspects, the cancer is a kidney cancer. Further aspects of kidney cancer include a renal cell carcinoma (RCC). In some aspects, the cancer is a liver cancer. Further aspects of liver cancer include a hepatocellular carcinoma. In some aspects, the cancer is a prostate cancer. Further aspects of prostate cancer include a castration-resistant prostate cancer (CRPC). In some aspects, the cancer is a metastatic form of a solid tumor. In some aspects, the metastatic form of a solid tumor is a metastatic form of a melanoma, a breast cancer, a colorectal cancer, a lung cancer, a head and neck cancer, a bladder cancer, a kidney cancer, an ovarian cancer, a pancreatic cancer, or a prostate cancer. In some aspects, the cancer is a non-solid tumor cancer. Non-solid tumor cancers include, but are not limited to, a B-cell lymphoma. Further aspects of B-cell lymphoma include, e.g., a chronic lymphocytic leukemia (CLL), a diffuse large B-cell lymphoma (DLBCL), a follicular lymphoma, myelodysplastic syndrome (MDS), a non-Hodgkin lymphoma (NHL), an acute lymphoblastic leukemia (ALL), a multiple myeloma, an acute myeloid leukemia (AML), or a mycosis fungoides (MF).

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some aspects, an immune checkpoint inhibitor is used to delay development of a disease or to slow the progression of a disease.

The term "anti-cancer therapy" refers to a therapy useful in treating cancer. Examples of anti-cancer therapeutic agents include, but are limited to, cytotoxic agents, chemotherapeutic agents, growth inhibitory agents, agents used in radiation therapy, anti-angiogenesis agents, apoptotic agents, anti-tubulin agents, and other agents to treat cancer, for example, anti-CD20 antibodies, platelet derived growth factor inhibitors (e.g., GLEEVEC™ (imatinib mesylate)), a COX-2 inhibitor (e.g., celecoxib), interferons, cytokines, antagonists (e.g., neutralizing antibodies) that bind to one or more of the following targets PDGFR-β, BlyS, APRIL, BCMA receptor(s), TRAIL/Apo2, other bioactive and organic chemical agents, and the like. Combinations thereof are also included in the invention.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylmelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chlorambucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifene citrate); (ii) aromatase inhibitors that inhibit the enzyme aromatase, which regulates estrogen production in the adrenal glands, such as, for example, 4 (5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1 λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A: 636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279 (29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy) quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl) methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino) phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacizumab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), interleukin 1 (IL-1) blockers such as anakinra (Kineret), T cell costimulation blockers such as abatacept (Orencia), interleukin 6 (IL-6) blockers such as tocilizumab (ACTEMERA®); interleukin 13 (IL-13) blockers such as lebrikizumab; interferon alpha (IFN) blockers such as Rontalizumab; beta 7 integrin blockers such as rhuMAb Beta7; IgE pathway blockers such as Anti-M1 prime; Secreted homotrimeric LTa3 and membrane bound heterotrimer LTa1/β2 blockers such as anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechin gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopoletin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhea, metastatic bone pain, headache and migraine, postoperative pain, mild-to-moderate pain due to inflammation and tissue injury, pyrexia, ileus, and renal colic.

A "growth inhibitory agent" when used herein refers to a compound or composition which inhibits growth of a cell either in vitro or in vivo. In one aspect, growth inhibitory agent is growth inhibitory antibody that prevents or reduces proliferation of a cell expressing an antigen to which the antibody binds. In another aspect, the growth inhibitory agent may be one which significantly reduces the percentage of cells in S phase. Aspects of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

A "subject" or an "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, the subject or individual is a human.

As used herein, "administering" is meant a method of giving a dosage of a compound (e.g., an immune checkpoint inhibitor) to a subject. In some aspects, the compositions utilized in the methods herein are administered intravenously. The compositions utilized in the methods described herein can be administered, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated).

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer, for example, to the symptoms of the disorder being treated, the presence or size of metastases, or the size of the primary tumor.

II. Predictive Methods and Assays

The present invention provides prognostic and therapeutic methods for cancer. In some instances, the methods herein may be used to identify an individual having a cancer who may benefit from a treatment including an immune checkpoint inhibitor, e.g., an immune checkpoint inhibitor described in Section IIIB herein, e.g., a PD-L1 axis binding antagonist, or any combination thereof, the method including determining a polygenic risk score (PRS) for one or more of vitiligo, psoriasis, and atopic dermatitis from a sample from the individual, wherein a PRS for vitiligo or psoriasis from the sample that is above a vitiligo or psoriasis reference PRS or a PRS for atopic dermatitis that is below an atopic dermatitis reference PRS identifies the individual as one who may benefit from a treatment comprising an immune checkpoint inhibitor.

The invention is based, at least in part, on the discovery that determining a polygenic risk score (PRS) for a dermatological autoimmune disease (e.g., vitiligo, psoriasis, or atopic dermatitis) can be used as a biomarker (e.g., a predictive biomarker) in the treatment of an individual having a cancer, e.g., for determining whether an individual having a cancer is likely to respond to treatment with an anti-cancer therapy that includes an immune checkpoint inhibitor (e.g., an immune checkpoint inhibitor described in Section IIIB herein, e.g., a PD-L1 axis binding antagonist) or for selecting a therapy for an individual having a cancer. In some aspects, a high PRS for vitiligo or psoriasis is associated with increased likelihood of response to treatment with an immune checkpoint inhibitor. In other aspects, a low PRS for atopic dermatitis is associated with increased likelihood of response to treatment with an immune checkpoint inhibitor. Accordingly, also provided herein are methods and assays of evaluating PRS for vitiligo, psoriasis, and atopic dermatitis in a sample from an individual. Any of the methods provided herein may further include measuring one or more tumor-associated factors from the tumor of an individual. Any of the methods provided herein may include administering an anti-cancer therapy other than, or in additional to, an immune checkpoint inhibitor to the individual. Any of the methods may further include administering an effective amount of an additional therapeutic agent, as described herein, to the individual.

A. Diagnostic Methods and Assays
i. Methods of Determining Polygenic Risk Scores (PRSs)
ia. Identification of Risk Alleles In some aspects, the invention features methods that include determining one or more polygenic risk scores (PRSs) of an individual for one or more dermatological autoimmune diseases, e.g., vitiligo, psoriasis, or atopic dermatitis. PRS may be represented as the number of single-nucleotide polymorphisms (SNPs) associated with increased likelihood of having or developing a disease, state, or condition ("risk alleles"), e.g., vitiligo risk alleles, psoriasis risk alleles, or atopic dermatitis risk alleles counted over a defined number of sequenced base pairs or in the whole genome sequence of an individual.

Risk alleles may be identified using a number of methods. In some aspects, risk alleles may be identified in a genome-wide association study (GWAS) for a pathological state, disease, or condition of interest. In some aspects, individuals included in the GWAS may be clinically diagnosed as having the disease, state, or condition. In other aspects, individuals may self-identify as having the disease, state, or condition. Exemplary GWAS for atopic dermatitis, clinically diagnosed psoriasis (PSO/IC), self-reported psoriasis (PSO/UKBB), vitiligo, and Alzheimer's disease are reported in Table 1. GWAS may identify one or more genic or non-genic loci (e.g., a SNP), e.g., 1 or more loci, 5 or more loci, 10 or more loci, 15 or more loci, 20 or more loci, 25 or more loci, 30 or more loci, 40 or more loci, 50 or more loci, 60 or more loci, 70 or more loci, 80 or more loci, 90 or more loci, 100 or more loci, 150 or more loci, 200 or more loci, 300 or more loci, 400 or more loci, 500 or more loci, 1000 or more loci, 2000 or more loci, 3000 or more loci, 4000 or more loci, 5000 or more loci, 10,000 or more loci, 50,000 or more loci, 100,000 or more loci, 200,000 or more loci, or 500,000 or more loci to be included in the set of risk alleles. The GWAS p-value threshold at which the PRS is most predictive is often unknown, and PRSs may use SNPs that do not achieve genome-wide significant p-values in the original GWAS (Dudbridge, *PLoS Genet.*, 9: e1003348, 2013; Euesden et al., *Bioinformatics,* 31:1466-1468, 2015). The p-value threshold for inclusion in the set of risk alleles may be, e.g., $p<0.2$, $p<0.1$, $p<0.05$, $p<0.01$, $p<0.001$, $p<1\times10^{-4}$, $p<1\times10^{-5}$, $p<1\times10^{-6}$, $p<1\times10^{-7}$, $p<1\times10^{-8}$, $p<1\times10^{-9}$, or $p<1\times10^{-10}$.

In some aspects, the GWAS may identify risk alleles for vitiligo (e.g., as described in Jin et al., *Nat. Genet.,* 48:1418-1424, 2016). In other aspects, the GWAS may identify risk alleles for psoriasis (e.g., as described in Tsoi et al., *Nat. Genet.,* 44:1341-1348, 2012 and Bycroft et al., *BioRxiv,* 2017). In yet other aspects, the GWAS may identify risk alleles for atopic dermatitis (e.g., as described in Paternoster et al., *Nat. Genet.,* 47:1449-1456, 2015).

In some aspects, the GWAS for vitiligo identifies 10 or more, 20 or more, 30 or more, 40 or more, 50 or more, 100 or more, 200 or more, 300 or more, 400 or more, 500 or more, 1000 or more, 2000 or more, 3000 or more, 4000 or more, 5000 or more, 6,000 or more, 10,000 or more, 15,000 or more, 25,000 or more, 50,000 or more, 100,000 or more, 150,000 or more, or 200,000 or more risk alleles for vitiligo. In some aspects, the GWAS for vitiligo identifies 70 to 110,000 risk alleles for vitiligo, e.g., 100 to 100,000 risk alleles, 250 to 150,000 risk alleles, 500 to 100,000 risk alleles, 1000 to 50,000 risk alleles, 2000 to 25,000 risk alleles, 3000 to 20,000 risk alleles. 4,000 to 15,000 risk alleles, or 5,000 to 10,000 risk alleles.

In some aspects, the GWAS for psoriasis identifies 10 or more, 20 or more, 30 or more, 40 or more, 50 or more, 100 or more, 200 or more, 300 or more, 400 or more, 500 or more, 1000 or more, 2000 or more, 3000 or more, 4000 or more, 5000 or more, 6,000 or more, 10,000 or more, 15,000 or more, 25,000 or more, 50,000 or more, 100,000 or more, 150,000 or more, or 200,000 or more risk alleles for psoriasis. In some aspects, the GWAS for psoriasis identifies 40 to 220,000 risk alleles for psoriasis, e.g., 50 to 216,000 risk alleles. 60 to 150,000 risk alleles, 70 to 150,000 risk alleles, 80 to 100,000 risk alleles. 90 to 50,000 risk alleles, 100 to 25,000 risk alleles, 200 to 15,000 risk alleles, 400 to 10,000 risk alleles, 500 to 8,000 risk alleles, 1000 to 7000 risk alleles, 2000 to 6000 risk alleles, or 3000 to 5000 risk alleles.

In some aspects, the GWAS for atopic dermatitis identifies 10 or more, 20 or more, 30 or more, 40 or more, 50 or more, 100 or more, 200 or more, 300 or more, 400 or more, 500 or more, 1000 or more, 2000 or more, 3000 or more, 4000 or more, 5000 or more, 6,000 or more, 10,000 or more, 15,000 or more, 25,000 or more, 50,000 or more, 100,000 or more, 150,000 or more, or 200,000 or more risk alleles for atopic dermatitis. In some aspects, the GWAS for atopic dermatitis identifies 10 to 160,000 risk alleles for atopic dermatitis, e.g., 20 to 150,000 risk alleles, 30 to 100,000 risk alleles, 50 to 50,000 risk alleles, 100 to 25,000 risk alleles, 200 to 10,000 risk alleles, 300 to 5000 risk alleles, 500 to 4000 risk alleles, or 600 to 3000 risk alleles.

TABLE 1

GWAS abbreviations and citations

| Abbreviation | GWAS | Citation |
| --- | --- | --- |
| AD | Atopic dermatitis | Paternoster et al., *Nat. Genet.*, 47: 1449-1456, 2015. |
| PSO/IC | Psoriasis Immunochip | Tsoi et al., *Nat. Genet.*, 44: 1341-1348, 2012. |
| PSO/UKBB | Self-Reported Psoriasis UK Biobank | Bycroft et al., *BioRxiv*, 2017. |
| VIT | Vitiligo | Jin et al., *Nat. Genet.*, 48: 1418-1424, 2016. |
| ALZ | Alzheimer's disease | Lambert et al., *Nat. Genet.*, 45, 1452-1458, 2013. |

In some aspects, the PRS of an individual is represented as the number of SNPs associated with risk for vitiligo, psoriasis, or atopic dermatitis ("risk alleles") occurring in the individual as counted over a defined number of sequenced base pairs. In some aspects, the number of sequenced base pairs (bp) is, e.g., at least 50 bp, at least 100 bp, at least 500 bp, at least 1 kbp, at least 10 kbp, at least 50 kbp, at least 100 kbp, at least 500 kbp, at least 1000 kbp, at least 1 Mbp, at least 500 Mbp, or at least 1 Gbp. In other aspects, the sequenced base pairs comprise the whole genome sequence (WGS) of an individual. Methods for WGS include, but are not limited to, the Illumina X10 HiSeq platform. In some aspects, WGS data is generated to an average read depth of at least 2×, at least 5×, at least 10×, at least 15×, at least 20×, at least 25×, at least 30×, at least 35×, at least 40×, at least 45×, at least 50×, or at least 100× coverage. Reads may be mapped to a reference genome, e.g., a human reference genome, e.g., hg38/GRCh38 (GCA_000001405.15). See, for example, Van der Auwera et al., *Curr Protoc Bioinformatics,* 11:11.10.1-11.10.33, 2013; McKenna et al., *Genome Res.,* 20:1297-1303, 2010; and DePristo et al., *Nat. Genet.,* 43:491-498, 2011.

PRSs may be assessed in one or more samples from an individual. A sample may be a tissue sample (e.g., a tissue biopsy), a cell sample, a whole blood sample, a buccal swab, a plasma sample, a serum sample, or a combination thereof. In some aspects, the sample contains germline DNA. In some aspects, the sample is a formalin-fixed and paraffin-embedded (FFPE) sample, an archival sample, a fresh sample, or a frozen sample.

In some aspects, a PRS for vitiligo may be determined for a sample from an individual. In some aspects, the PRS identifies 0, 1 or more, 5 or more, 10 or more, 15 or more, 20 or more, 25 or more, 30 or more, 40 or more, 50 or more, 60 or more, 70 or more, 80 or more, 90 or more, 100 or more, 150 or more, 200 or more, 300 or more, 400 or more, 500 or more, 1000 or more, 2000 or more, 3000 or more, 4000 or more, 5000 or more, 10,000 or more, 50,000 or more, 100,000 or more, 200,000 or more, or 500,000 or more risk alleles for vitiligo in the sample from the individual. In some aspects, the PRS score for vitiligo of the individual is higher than 0%, higher than 10%, higher than 20%, higher than 30%, higher than 40%, higher than 50%, higher than 60%, higher than 70%, higher than 80%, higher than 90%, or higher than 100% of PRS scores for vitiligo for individuals in a reference population.

In one aspect, the PRS of an individual for vitiligo is represented as the number of SNPs associated with risk for vitiligo counted in a WGS sample, wherein the sample is a blood sample or a buccal swab.

In some aspects, a PRS for psoriasis may be determined for a sample from an individual. In some aspects, the PRS identifies 0, 1 or more, 5 or more, 10 or more, 15 or more, 20 or more, 25 or more, 30 or more, 40 or more, 50 or more, 60 or more, 70 or more, 80 or more, 90 or more, 100 or more, 150 or more, 200 or more, 300 or more, 400 or more, 500 or more, 1000 or more, 2000 or more, 3000 or more, 4000 or more, 5000 or more, 10,000 or more, 50,000 or more, 100,000 or more, 200,000 or more, or 500,000 or more risk alleles for psoriasis in the sample from the individual. In some aspects, the PRS score for psoriasis of the individual is higher than 0%, higher than 10%, higher than 20%, higher than 30%, higher than 40%, higher than 50%, higher than 60%, higher than 70%, higher than 80%, higher than 90%, or higher than 100% of PRS scores for psoriasis for individuals in a reference population.

In one aspect, the PRS of an individual for psoriasis is represented as the number of SNPs associated with risk for psoriasis counted in a whole genome sequence (WGS) sample, wherein the sample is a blood sample or a buccal swab.

In some aspects, a PRS for atopic dermatitis may be determined for a sample from an individual. In some aspects, the PRS identifies 0, 1 or more, 5 or more, 10 or more, 15 or more, 20 or more, 25 or more, 30 or more, 40 or more, 50 or more, 60 or more, 70 or more, 80 or more, 90 or more, 100 or more, 150 or more, 200 or more, 300 or more, 400 or more, 500 or more, 1000 or more, 2000 or more, 3000 or more, 4000 or more, 5000 or more, 10,000 or more, 50,000 or more, 100,000 or more, 200,000 or more, or 500,000 or more risk alleles for atopic dermatitis in the sample from the individual. In some aspects, the PRS score for atopic dermatitis of the individual is higher than 0%, higher than 10%, higher than 20%, higher than 30%, higher than 40%, higher than 50%, higher than 60%, higher than 70%, higher than 80%, higher than 90%, or higher than 100% of PRS scores for atopic dermatitis for individuals in a reference population.

In one aspect, the PRS of an individual for atopic dermatitis is represented as the number of SNPs associated with risk for atopic dermatitis counted in a whole genome sequence (WGS) sample, wherein the sample is a blood sample or a buccal swab.

In some aspects, PRSs may be determined for an individual for at least two dermatological autoimmune diseases. In some aspects, a PRS for vitiligo and a PRS for psoriasis are determined for an individual. In some aspects, a PRS for vitiligo and a PRS for atopic dermatitis are determined for an individual. In some instances, a PRS for psoriasis and a PRS for atopic dermatitis are determined for an individual.

In some aspects, a PRS may be determined for an individual for all three dermatological autoimmune diseases, e.g., a PRS for vitiligo, a PRS for psoriasis, and a PRS for atopic dermatitis are determined for an individual.

In some aspects, the PRS for vitiligo, psoriasis, or atopic dermatitis of the sample from the individual or the PRS for vitiligo, psoriasis, or atopic dermatitis of a sample from an individual in the reference population is calculated using the equation:

$$\hat{S} = \sum_{i=1}^{M} \beta_i \cdot G_i$$

wherein $\hat{S}$ is the PRS for vitiligo, psoriasis, or atopic dermatitis, M is the number of risk alleles detected in the sample, wherein a risk allele is identified as a SNP having a p-value at or below a given p-value cutoff in a GWAS (e.g., a GWAS of Table 1) for vitiligo, psoriasis, or atopic dermatitis; i represents the index of a given SNP; $\beta_i$ is the log odds ratio of the ith SNP; and $G_i=\{0,1,2\}$ is the number of copies of the SNP in the sample from the individual.

ic. Reference Populations

In some aspects, the PRS of an individual for vitiligo, psoriasis, or atopic dermatitis is compared to PRSs in a reference population. In some aspects, the reference population is a population of individuals having a cancer, the population of individuals consisting of a first subset of individuals who have been treated with an immune checkpoint inhibitor therapy, e.g., an immune checkpoint inhibitor described in Section IIIB herein, e.g., a PD-L1 axis binding antagonist, and a second subset of individuals who have been treated with a non-immune checkpoint inhibitor therapy e.g., a non-immune checkpoint inhibitor therapy described in Section IIID herein, e.g., a chemotherapy, wherein the non-immune checkpoint inhibitor therapy does not comprise an immune checkpoint inhibitor. In some aspects, the reference population is the population of the IMvigor210 clinical trial (Balar et al. *Lancet,* 389:67-76, 2017). In some aspects, the reference population is the population of the IMvigor211 clinical trial. (Powles et al. *Lancet,* 391:748-757, 2018). In some aspects, the reference population is the biomarker available population of the IMvigor211 clinical trial.

In some aspects, the reference population may be used to determine a reference PRS. In some aspects, the reference is a PRS value that significantly separates each of the first subset and the second subsets of individuals based on a significant difference in responsiveness to treatment with the immune checkpoint inhibitor therapy relative to responsiveness to treatment with the non-immune checkpoint inhibitor therapy. The reference population may be used to determine one, two, or all three of a vitiligo reference PRS, a psoriasis reference PRS, and an atopic dermatitis reference PRS. The difference in responsiveness to treatment may be, for example, a difference in overall survival (OS) or progression-free survival (PFS).

In some aspects, the reference PRS is defined as, e.g., the $0^{th}$ percentile, $1^{st}$ percentile, $2^{nd}$ percentile, $3^{rd}$ percentile, $4^{th}$ percentile, $5^{th}$ percentile, $6^{th}$ percentile, $7^{th}$ percentile, $8^{th}$ percentile, $9^{th}$ percentile, $10^{th}$ percentile, $11^{th}$ percentile, $12^{th}$ percentile, $13^{th}$ percentile, $14^{th}$ percentile, $15^{th}$ percentile, $16^{th}$ percentile, $17^{th}$ percentile, $18^{th}$ percentile, $19^{th}$ percentile, $20^{th}$ percentile, $21^{st}$ percentile, $22^{nd}$ percentile, $23^{rd}$ percentile, $24^{th}$ percentile, $25^{th}$ percentile, $26^{th}$ percentile, $27^{th}$ percentile, $28^{th}$ percentile, $29^{th}$ percentile, $30^{th}$ percentile, $31^{st}$ percentile, $32^{nd}$ percentile, $33^{rd}$ percentile, $34^{th}$ percentile, $35^{th}$ percentile, $36^{th}$ percentile, $37^{th}$ percentile, $38^{th}$ percentile, $39^{th}$ percentile, $40^{th}$ percentile, $41^{st}$ percentile, $42^{nd}$ percentile, $43^{rd}$ percentile, $44^{th}$ percentile, $45^{th}$ percentile, $46^{th}$ percentile, $47^{th}$ percentile, $48^{th}$ percentile, $49^{th}$ percentile, $50^{th}$ percentile, $51^{st}$ percentile, $52^{nd}$ percentile, $53^{rd}$ percentile, $54^{th}$ percentile, $55^{th}$ percentile, $56^{th}$ percentile, $57^{th}$ percentile, $58^{th}$ percentile, $59^{th}$ percentile, $60^{th}$ percentile, $61^{st}$ percentile, $62^{nd}$ percentile, $63^{rd}$ percentile, $64^{th}$ percentile, $65^{th}$ percentile, $66^{th}$ percentile, $67^{th}$ percentile, $68^{th}$ percentile, $69^{th}$ percentile, $70^{th}$ percentile, $71^{st}$ percentile, $72^{nd}$ percentile, $73^{rd}$ percentile, $74^{th}$ percentile, $75^{th}$ percentile, $76^{th}$ percentile, $77^{th}$ percentile, $78^{th}$ percentile, $79^{th}$ percentile, $80^{th}$ percentile, $81^{st}$ percentile, $82^{nd}$ percentile, $83^{rd}$ percentile, $84^{th}$ percentile, $85^{th}$ percentile, $86^{th}$ percentile, $87^{th}$ percentile, $88^{th}$ percentile, $89^{th}$ percentile, $90^{th}$ percentile, $91^{st}$ percentile, $92^{nd}$ percentile, $93^{rd}$ percentile, $94^{th}$ percentile, $95^{th}$ percentile, $96^{th}$ percentile, $97^{th}$ percentile, $98^{th}$ percentile, or $99^{th}$ percentile of PRSs in the reference population.

In some aspects, the reference PRS is defined as the $20^{th}$ percentile of PRSs in the reference population. In some aspects, the reference PRS is defined as the $50^{th}$ percentile of PRSs in the reference population. In some aspects, the reference PRS is defined as the $80^{th}$ percentile of PRSs in the reference population.

ii. Methods of Selecting a Therapy

In some aspects, one or more PRS scores of an individual is used in determining whether to treat a patient with an immune checkpoint inhibitor, e.g., an immune checkpoint inhibitor described in Section IIIB herein, e.g., a PD-L1 axis binding antagonist (e.g., a PD-L1 binding antagonist, e.g., atezolizumab).

iia. Relationship Between Dermatological irAEs, PRSs, and OS Under Immune Checkpoint Inhibitor Therapy It has been hypothesized that a genetic component contributes to the development of dermatological immune-related adverse events (irAEs); however, few biomarkers associated with irAEs have previously been identified (June et al., *Nat. Med.,* 23:540-547, 2017). Herein, biomarkers for risk of developing the dermatological autoimmune diseases vitiligo, psoriasis, and atopic dermatitis (e.g., risk alleles) are shown to be correlated with the likelihood that an individual will benefit from immune checkpoint inhibitor therapy. In particular, polygenic risk scores (PRSs) of an individual for vitiligo, psoriasis, and atopic dermatitis were determined and were found to be positively associated with OS under treatment with atezolizumab (an immune checkpoint inhibitor) as compared to treatment with a non-immune checkpoint inhibitor (Example 4).

iib. Methods of Selecting a Therapy

An immune checkpoint inhibitor may be selected for treatment of an individual having a cancer when one or more of a PRS for vitiligo, psoriasis, and/or atopic dermatitis for the individual identifies the individual as one who may benefit from a treatment comprising an immune checkpoint inhibitor, such as when the PRS for vitiligo is relatively high, the PRS for psoriasis is relatively high, and/or the PRS for atopic dermatitis is relatively low compared to a vitiligo reference PRS, psoriasis reference PRS, and/or atopic dermatitis reference PRS, respectively.

In some aspects, the invention features a method identifying an individual having a cancer who may benefit from a treatment comprising an immune checkpoint inhibitor, the method comprising determining one or more of a PRS for vitiligo, a PRS for psoriasis, and a PRS for atopic dermatitis for an individual, wherein a PRS of the individual for vitiligo that is above a vitiligo reference PRS (e.g., a vitiligo reference PRS defined in Section IIA(ic)) identifies the individual as one who may benefit from a treatment comprising an immune checkpoint inhibitor; a PRS of the individual for psoriasis that is above a psoriasis reference PRS (e.g., a psoriasis reference PRS defined in Section IIA(ic)) identifies the individual as one who may benefit from a treatment comprising an immune checkpoint inhibitor; or a PRS of the individual for atopic dermatitis that is below an atopic dermatitis reference PRS (e.g., an atopic dermatitis reference PRS defined in Section IIA(ic)) identifies the individual as one who may benefit from a treatment comprising an immune checkpoint inhibitor. In some aspects, the invention features selecting a therapy for an individual having a cancer based on one or more of the PRS for vitiligo, the PRS for psoriasis, and the PRS for atopic dermatitis. In some aspects, the invention features administering to the individual an effective amount of an immune checkpoint inhibitor. In some aspects, one or more of a PRS for vitiligo, a PRS for psoriasis, and a PRS for atopic dermatitis is determined for an individual prior to the administering of an immune checkpoint inhibitor.

PRS for Vitiligo

In some aspects, the PRS of the individual for vitiligo is greater than 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of PRSs for vitiligo in the reference population.

In some aspects, the vitiligo reference PRS is defined as the $25^{th}$ percentile of PRSs for vitiligo in the reference population, and the PRS for vitiligo of the individual is greater than 25% of PRSs for vitiligo in the reference population.

In other aspects, the vitiligo reference PRS is defined as the $25^{th}$ percentile of PRSs for vitiligo in the reference population, and the PRS for vitiligo of the individual is less than 25% of PRSs for vitiligo in the reference population.

In some aspects, the vitiligo reference PRS is defined as the $50^{th}$ percentile of PRSs for vitiligo in the reference population, and the PRS for vitiligo of the individual is greater than 50% of PRSs for vitiligo in the reference population.

In other aspects, the vitiligo reference PRS is defined as the $50^{th}$ percentile of PRSs for vitiligo in the reference population, and the PRS for vitiligo of the individual is less than 50% of PRSs for vitiligo in the reference population.

In some aspects, the vitiligo reference PRS is defined as the $75^{th}$ percentile of PRSs for vitiligo in the reference population, and the PRS for vitiligo of the individual is greater than 75% of PRSs for vitiligo in the reference population.

In other aspects, the vitiligo reference PRS is defined as the $75^{th}$ percentile of PRSs for vitiligo in the reference population, and the PRS for vitiligo of the individual is less than 75% of PRSs for vitiligo in the reference population.

In some aspects, the PRS for vitiligo determined from the sample is above the vitiligo reference PRS and the method further comprises administering to the individual an effective amount of an immune checkpoint inhibitor.

In some aspects, the PRS for vitiligo determined from the sample is above the vitiligo reference PRS; the PRS for psoriasis determined from the sample is below the psoriasis reference PRS; the PRS for atopic dermatitis determined from the sample is above the atopic dermatitis reference PRS; and the method further comprises administering to the individual an effective amount of an immune checkpoint inhibitor.

In other aspects, the PRS for vitiligo determined from the sample is below the vitiligo reference PRS.

PRS for Psoriasis

In some aspects, the PRS of the individual for psoriasis is greater than 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of PRSs for psoriasis in the reference population.

In some aspects, the psoriasis reference PRS is defined as the $25^{th}$ percentile of PRSs for psoriasis in the reference population, and the PRS for psoriasis of the individual is greater than 25% of PRSs for psoriasis in the reference population.

In other aspects, the psoriasis reference PRS is defined as the $25^{th}$ percentile of PRSs for psoriasis in the reference population, and the PRS for psoriasis of the individual is less than 25% of PRSs for psoriasis in the reference population.

In some aspects, the psoriasis reference PRS is defined as the $50^{th}$ percentile of PRSs for psoriasis in the reference population, and the PRS for psoriasis of the individual is greater than 50% of PRSs for psoriasis in the reference population.

In other aspects, the psoriasis reference PRS is defined as the $50^{th}$ percentile of PRSs for psoriasis in the reference population, and the PRS for psoriasis of the individual is less than 50% of PRSs for psoriasis in the reference population.

In some aspects, the psoriasis reference PRS is defined as the $75^{th}$ percentile of PRSs for psoriasis in the reference population, and the PRS for psoriasis of the individual is greater than 75% of PRSs for psoriasis in the reference population.

In other aspects, the psoriasis reference PRS is defined as the $75^{th}$ percentile of PRSs for psoriasis in the reference population, and the PRS for psoriasis of the individual is less than 75% of PRSs for psoriasis in the reference population.

In some aspects, the PRS for psoriasis determined from the sample is above the psoriasis reference PRS and the method further comprises administering to the individual an effective amount of an immune checkpoint inhibitor.

In some aspects, the PRS for psoriasis determined from the sample is above the psoriasis reference PRS; the PRS for vitiligo determined from the sample is below the vitiligo reference PRS; the PRS for atopic dermatitis determined from the sample is above the atopic dermatitis reference PRS; and the method further comprises administering to the individual an effective amount of an immune checkpoint inhibitor.

In other aspects, the PRS for psoriasis determined from the sample is below the psoriasis reference PRS.

PRS for Atopic Dermatitis

In some aspects, the PRS of the individual for atopic dermatitis is less than 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of PRSs for atopic dermatitis in the reference population.

In some aspects, the atopic dermatitis reference PRS is defined as the $75^{th}$ percentile of PRSs for atopic dermatitis in the reference population, and the PRS for atopic dermatitis of the individual is less than 75% of PRSs for atopic dermatitis in the reference population.

In other aspects, the atopic dermatitis reference PRS is defined as the $75^{th}$ percentile of PRSs for atopic dermatitis in the reference population, and the PRS for atopic dermatitis of the individual is greater than 75% of PRSs for atopic dermatitis in the reference population.

In some aspects, the atopic dermatitis reference PRS is defined as the $50^{th}$ percentile of PRSs for atopic dermatitis in the reference population, and the PRS for atopic dermatitis of the individual is less than 50% of PRSs for atopic dermatitis in the reference population.

In other aspects, the atopic dermatitis reference PRS is defined as the $50^{th}$ percentile of PRSs for atopic dermatitis in the reference population, and the PRS for atopic dermatitis of the individual is greater than 50% of PRSs for atopic dermatitis in the reference population.

In some aspects, the atopic dermatitis reference PRS is defined as the $25^{th}$ percentile of PRSs for atopic dermatitis in the reference population, and the PRS for atopic dermatitis of the individual is less than 25% of PRSs for atopic dermatitis in the reference population.

In other aspects, the atopic dermatitis reference PRS is defined as the $20^{th}$ percentile of PRSs for atopic dermatitis in the reference population, and the PRS for atopic dermatitis of the individual is greater than 25% of PRSs for atopic dermatitis in the reference population.

In some aspects, the PRS for atopic dermatitis determined from the sample is below the atopic dermatitis reference PRS and the method further comprises administering to the individual an effective amount of an immune checkpoint inhibitor.

In some aspects, the PRS for atopic dermatitis determined from the sample is below the psoriasis reference PRS; the PRS for vitiligo determined from the sample is below the vitiligo reference PRS; the PRS for psoriasis determined from the sample is below the psoriasis reference PRS; and the method further comprises administering to the individual an effective amount of an immune checkpoint inhibitor.

In other aspects, the PRS for atopic dermatitis determined from the sample is above the atopic dermatitis reference PRS.

Combinations of Two PRSs

In some aspects, the PRS for vitiligo determined from the sample is above the vitiligo reference PRS, and the PRS for psoriasis determined from the sample is above the psoriasis reference PRS. In some aspects, the method further comprises administering to the individual an effective amount of an immune checkpoint inhibitor.

In some aspects, the PRS for vitiligo determined from the sample is above the vitiligo reference PRS, and the PRS for psoriasis determined from the sample is below the psoriasis reference PRS. In some aspects, the method further comprises administering to the individual an effective amount of an immune checkpoint inhibitor.

In some aspects, the PRS for vitiligo determined from the sample is below the vitiligo reference PRS, and the PRS for psoriasis determined from the sample is above the psoriasis reference PRS. In some aspects, the method further comprises administering to the individual an effective amount of an immune checkpoint inhibitor. In some aspects, the PRS for vitiligo determined from the sample is below the vitiligo reference PRS, and the PRS for psoriasis determined from the sample is below the psoriasis reference PRS.

In some aspects, the PRS for vitiligo determined from the sample is above the vitiligo reference PRS, and the PRS for atopic dermatitis determined from the sample is below the atopic dermatitis reference PRS. In some aspects, the method further comprises administering to the individual an effective amount of an immune checkpoint inhibitor.

In some aspects, the PRS for vitiligo determined from the sample is above the vitiligo reference PRS, and the PRS for atopic dermatitis determined from the sample is above the atopic dermatitis reference PRS. In some aspects, the method further comprises administering to the individual an effective amount of an immune checkpoint inhibitor.

In some aspects, the PRS for vitiligo determined from the sample is below the vitiligo reference PRS, and the PRS for atopic dermatitis determined from the sample is below the atopic dermatitis reference PRS. In some aspects, the method further comprises administering to the individual an effective amount of an immune checkpoint inhibitor.

In some aspects, the PRS for vitiligo determined from the sample is below the vitiligo reference PRS, and the PRS for atopic dermatitis determined from the sample is above the atopic dermatitis reference PRS.

In some aspects, the PRS for psoriasis determined from the sample is above the psoriasis reference PRS, and the PRS for atopic dermatitis determined from the sample is below the atopic dermatitis reference PRS. In some aspects, the method further comprises administering to the individual an effective amount of an immune checkpoint inhibitor.

In some aspects, the PRS for psoriasis determined from the sample is above the psoriasis reference PRS, and the PRS for atopic dermatitis determined from the sample is above the atopic dermatitis reference PRS. In some aspects, the method further comprises administering to the individual an effective amount of an immune checkpoint inhibitor.

In some aspects, the PRS for psoriasis determined from the sample is below the psoriasis reference PRS, and the PRS for atopic dermatitis determined from the sample is below the atopic dermatitis reference PRS. In some aspects, the method further comprises administering to the individual an effective amount of an immune checkpoint inhibitor.

In some aspects, the PRS for psoriasis determined from the sample is below the psoriasis reference PRS and the PRS for atopic dermatitis determined from the sample is above the atopic dermatitis reference PRS.

Combinations of Three PRSs

In some aspects, the PRS for vitiligo determined from the sample is above the vitiligo reference PRS; the PRS for psoriasis determined from the sample is above the psoriasis reference PRS; and the PRS for atopic dermatitis determined from the sample is below the atopic dermatitis reference PRS. In some aspects, the method further comprises administering to the individual an effective amount of an immune checkpoint inhibitor.

In some aspects, the PRS for vitiligo determined from the sample is above the vitiligo reference PRS; the PRS for psoriasis determined from the sample is above the psoriasis reference PRS; and the PRS for atopic dermatitis determined from the sample is above the atopic dermatitis reference PRS. In some aspects, the method further comprises administering to the individual an effective amount of an immune checkpoint inhibitor.

In some aspects, the PRS for vitiligo determined from the sample is above the vitiligo reference PRS; the PRS for psoriasis determined from the sample is below the psoriasis reference PRS; and the PRS for atopic dermatitis determined from the sample is below the atopic dermatitis reference PRS. In some aspects, the method further comprises administering to the individual an effective amount of an immune checkpoint inhibitor.

In some aspects, the PRS for vitiligo determined from the sample is above the vitiligo reference PRS; the PRS for psoriasis determined from the sample is below the psoriasis reference PRS; and the PRS for atopic dermatitis determined from the sample is above the atopic dermatitis reference PRS. In some aspects, the method further comprises administering to the individual an effective amount of an immune checkpoint inhibitor.

In some aspects, the PRS for vitiligo determined from the sample is below the vitiligo reference PRS; the PRS for psoriasis determined from the sample is above the psoriasis reference PRS; and the PRS for atopic dermatitis determined from the sample is below the atopic dermatitis reference PRS. In some aspects, the method further comprises administering to the individual an effective amount of an immune checkpoint inhibitor.

In some aspects, the PRS for vitiligo determined from the sample is below the vitiligo reference PRS; the PRS for psoriasis determined from the sample is above the psoriasis reference PRS; and the PRS for atopic dermatitis determined from the sample is above the atopic dermatitis reference PRS. In some aspects, the method further comprises administering to the individual an effective amount of an immune checkpoint inhibitor.

In some aspects, the PRS for vitiligo determined from the sample is below the vitiligo reference PRS; the PRS for psoriasis determined from the sample is below the psoriasis reference PRS; and the PRS for atopic dermatitis determined from the sample is below the atopic dermatitis reference PRS. In some aspects, the method further comprises administering to the individual an effective amount of an immune checkpoint inhibitor.

In some aspects, the PRS for vitiligo determined from the sample is above the vitiligo reference PRS; the PRS for psoriasis determined from the sample is below the psoriasis reference PRS; and the PRS for atopic dermatitis determined from the sample is below the atopic dermatitis reference PRS. In some aspects, the method further comprises administering to the individual an effective amount of an immune checkpoint inhibitor.

In some aspects, the PRS for vitiligo determined from the sample is below the vitiligo reference PRS; the PRS for psoriasis determined from the sample is below the psoriasis reference PRS; and the PRS for atopic dermatitis determined from the sample is above the atopic dermatitis reference PRS.

iii. Methods of Assessing Tumor-Associated Factors

The presence or absence of one or more factors in the tumor or the tumor microenvironment ("tumor-associated factors") may be associated with the efficacy of immune checkpoint inhibitor therapy. Herein, we identify several tumor-associated factors that are positively associated with the predictive capacity of a PRS for psoriasis (Example 6): these factors include high immune cell (IC) staining of PD-L1, high $CD8^+$ T-effector function, high expression of IL-17-induced genes, high expression of IL23A, low expression of IL12A, and high tumor mutational burden. In some aspects, one or more tumor-associated factors are measured in one or more tumor samples for an individual for which one, two, or all three of a PRS for vitiligo, a PRS for psoriasis, and a PRS for atopic dermatitis are also measured. Analysis of the one or more tumor-associated factors can occur prior to, simultaneously, and/or following determination of the PRS for one or more of vitiligo, psoriasis, and atopic dermatitis of the individual.

In some aspects, IC staining of PD-L1, $CD8^+$ T-effector function, expression of IL-17-induced genes, expression of IL23A, expression of IL12A, or high tumor mutational burden is measured in a sample of the tumor of the individual.

In some aspects, at least two of IC staining of PD-L1, $CD8^+$ T-effector function, expression of IL-17-induced genes, expression of IL23A, expression of IL12A, and high tumor mutational burden are measured in a sample of the tumor of the individual.

In some aspects, at least three of IC staining of PD-L1, $CD8^+$ T-effector function, expression of IL-17-induced genes, expression of IL23A, expression of IL12A, and high tumor mutational burden are measured in a sample of the tumor of the individual.

In some aspects, at least four of IC staining of PD-L1, $CD8^+$ T-effector function, expression of IL-17-induced genes, expression of IL23A, expression of IL12A, and high tumor mutational burden are measured in a sample of the tumor of the individual.

In some aspects, at least five of IC staining of PD-L1, $CD8^+$ T-effector function, expression of IL-17-induced genes, expression of IL23A, expression of IL12A, and high tumor mutational burden are measured in a sample of the tumor of the individual.

In some aspects, all six of IC staining of PD-L1, $CD8^+$ T-effector function, expression of IL-17-induced genes, expression of IL23A, expression of IL12A, and high tumor mutational burden are measured in a sample of the tumor of the individual.

Tumor-associated factors may be assessed in one or more samples from an individual. A sample may be a tissue sample, a tissue biopsy, a cell sample, a whole blood sample, a plasma sample, a serum sample, or a combination thereof. In some aspects, the tissue sample is a tumor tissue sample. In some aspects, the tumor tissue sample comprises tumor cells, tumor-infiltrating immune cells, stromal cells, or a combination thereof. The tumor tissue sample may be assessed to confirm the presence of tumor cells and/or the proportion of tumor cells in the sample, e.g., by hematoxylin and eosin (H&E) staining of slides and subsequent observation. The sample may contain, e.g., at least 10% tumor cells. In some aspects, the tumor tissue sample is a formalin-fixed and paraffin-embedded (FFPE) sample, an archival sample, a fresh sample, or a frozen sample.

iii(a). IC Staining of PD-L1

In some aspects, the level of immune cell (IC) staining (e.g., by immunohistochemistry (IHC)) for PD-L1 of a sample from the tumor of the individual is quantified. IC staining may be reported as, e.g., IC0 (no evidence of immune cell staining of PD-L1) or as IC1, IC2, or IC3, designating increasing levels of immune cell PD-L1 staining as defined in Powles et al., *Lancet*, 391:748-757, 2018. Likewise, the level of tumor cell (TC) staining (e.g., by immunohistochemistry) for PD-L1 of a sample from the tumor of the individual may be quantified. TC staining may be reported as, e.g., TC0 (no evidence of immune cell staining of PD-L1) or as TC1, TC2, or TC3, designating increasing levels of tumor cell PD-L1 staining, as defined in Table 2. Low IC staining of PD-L1 may be defined as, e.g., IC0 or IC0 and IC1. Staining may be performed using a diagnostic anti-human PD-L1 monoclonal antibody, e.g., 22C3, SP142, SP263, or 28-8. In some aspects, the diagnostic antibody is SP142. SP142 is described in US Patent Application Publication No. 2018/0022809. In some aspects, the protocol for staining is the VENTANA PD-L1 SP142 immunohistochemistry (IHC) assay.

The amino acid sequence of the heavy chain variable region of SP142 is the following:

(SEQ ID NO: 32)
QSLEESGGRLVKPDETLTITCTVSGIDLSSNGLTWVRQAPGEGLEWIG
                          HVR-H1

TINKDASAYYASWAKGRLTISKPSSTKVDLKITSPTTEDTATYFCGR
    HVR-H2

IAFKTGTSIWGPGTLVTVSS.
   HVR-H3

The amino acid sequence of the light chain variable region of SP142 is the following:

(SEQ ID NO: 33)
AIVMTQTPSPVSAAVGGTVTINCQASESVYSNNYLSWFQQKPGQPPKL
                      HVR-L1

LIYLASTLASGVPSRFKGSGSGTQFTLTISGVQCDDAATYYC
   HVR-L2
IGGKSSSTDGNAFGGGTEVVVR.
   HVR-L3

In some aspects, detectable PD-L1 staining is present in tumor-infiltrating immune cells covering <1% of the tumor area.

In some aspects, detectable PD-L1 staining is present in tumor-infiltrating immune cells covering ≥5% of the tumor area. In some aspects, the presence of detectable PD-L1 staining in tumor-infiltrating immune cells covering ≥5% of the tumor area is positively associated with the predictive capacity of a PRS for psoriasis.

In some aspects, detectable PD-L1 staining is present in tumor-infiltrating immune cells covering ≥50% of the tumor area. In some aspects, the presence of detectable PD-L1 staining in tumor-infiltrating immune cells covering ≥50% of the tumor area is positively associated with the predictive capacity of a PRS for psoriasis.

TABLE 2

PD-L1 scoring criteria on TC and IC using the SP142 assay

| PD-L1 TC Scoring | | PD-L1 IC Scoring | |
| --- | --- | --- | --- |
| [a]TC Score | % of PD-L1-Expressing TC | [b]IC Score | % of PD-L1-Expressing IC |
| TC3 | Presence of discernible PD-L1 staining of any intensity in ≥50% of tumor cells | IC3 | Presence of discernible PD-L1 staining of any intensity in tumor-infiltrating immune cells covering 0% of tumor area occupied by tumor cells, associated intratumoral stroma, and contiguous peri-tumoral desmoplastic stroma |
| TC2 | Presence of discernible PD-L1 staining of any intensity in ≥5% to <50% of tumor cells | IC2 | Presence of discernible PD-L1 staining of any intensity in tumor-infiltrating immune cells covering ≥5% to <10% of tumor area occupied by tumor cells, associated intratumoral stroma, and contiguous peri-tumoral desmoplastic stroma |
| TC1 | Presence of discernible PD-L1 staining of any intensity in ≥1% to <5% of tumor cells | IC1 | Presence of discernible PD-L1 staining of any intensity in tumor-infiltrating immune cells covering ≥1% to <5% of tumor area occupied by tumor cells, associated intratumoral stroma, and contiguous peri-tumoral desmoplastic stroma |
| TC0 | Absence of any discernible PD-L1 staining OR Presence of discernible PD-L1 staining of any intensity in <1% of tumor cells | IC0 | Absence of any discernible PD-L1 staining OR Presence of discernible PD-L1 staining of any intensity in tumor-infiltrating immune cells covering <1% of tumor area occupied by tumor cells, associated intratumoral stroma, and contiguous peri-tumoral desmoplastic stroma |

[a]TC scored as percentage of tumor cells;
[b]IC scored as percentage of tumor area.

iii(b). CD8+ T-Effector Function

In some aspects, the CD8+ T-effector function of a sample from the tumor of the individual is quantified. CD8+ T-effector function may be assessed by quantification of, e.g., expression of CD84, expression of PRF1, and the T-effector tumor gene expression signature score (T-effector signature score). In some aspects, the T-effector signature score is computed based on the expression of one or more of CD8A, GZMA, GZMB, INFG, CXCL9, CXCL10, PRF1, and TBX21, e.g., as described in Example 6B.

Expression of one or more of CD8A, PRF1, CD8A, GZMA, GZMB, INFG, CXCL9, CXCL10, PRF1, or TBX21 in a tumor sample may be assessed by a number of methodologies, including, but not limited to, RNA-seq, PCR, RT-qPCR, qPCR, multiplex qPCR, multiplex RT-qPCR, NANOSTRING® nCOUNTER® Gene Expression Assay, microarray analysis, serial analysis of gene expression (SAGE), Northern blot analysis, MassARRAY, ISH, and whole genome sequencing, or combinations thereof.

In some instances, expression is assessed by tumor RNA-seq, e.g., using TruSeq RNA Access technology (Illumina). In some aspects, RNA is isolated from tumor tissue, e.g., from macro-dissected slides. In some aspects, high CD8+ T-effector function is positively associated with the predictive capacity of a PRS for psoriasis. High CD8+ effector function may be defined relative to a reference population, e.g., a population studied in a clinical trial, e.g., a reference population described in Section IIA(ic) herein. In some aspects, "high" CD8+ effector function for an individual is defined as one, two, or all three of (a) expression of CD8A that is greater than the median expression of CD8A in a reference population; (b) expression of PRF1 that is greater than the median expression of PRF1 in a reference population; and (c) a T-effector signature score that is higher than the median score in a reference population.

iii(c). IL-17-Induced Genes

In some aspects, the expression level of one or more IL-17-induced genes in a sample from the tumor of the individual is quantified, e.g., by RNA-seq. The IL-17-induced genes may be, e.g., one or both of CXCL2 and CCL20. In some aspects, the expression level of one or both of IL-17A and IL-17F is quantified in the tumor sample of the individual. In some aspects, high expression of one or both of CXCL2 and CCL20 is positively associated with the predictive capacity of a PRS for psoriasis. High expression of CXCL2, CCL20, IL-17A, or IL-17F may be defined relative to a reference population, e.g., a population studied in a clinical trial, e.g., a reference population described in Section IIA(ic) herein (e.g., the biomarker available population of the IMvigor211 clinical trial). In some aspects, "high" expression of CXCL2, CCL20, IL-17A, or IL-17F for an individual is defined as expression of CXCL2, CCL20, IL-17A, or IL-17F that is greater than the median expression of CXCL2, CCL20, IL-17A, or IL-17F in a reference population.

iii(d). IL-23A and IL-12A Expression

In some aspects, the expression level of one or both of IL-23A and IL-12A in a sample from the tumor of the individual is quantified, e.g., by RNA-seq. In some aspects, high expression of IL-23A is positively associated with the predictive capacity of a PRS for psoriasis. In some aspects, low expression of IL-12A is positively associated with the predictive capacity of a PRS for psoriasis. High expression of IL-23A may be defined relative to a reference population, e.g., a population studied in a clinical trial, e.g., a reference population described in Section IIA(ic) herein. In some aspects, "high" expression of IL-23A for an individual is defined as expression of IL-23A that is greater than the median expression of IL-23A in a reference population. Low expression of IL-12A may be defined relative to a reference population, e.g., a population studied in a clinical trial, e.g., a reference population described in Section IIA (ic) herein. In some aspects, "low" expression of IL-12A for an individual is defined as expression of IL-12A that is less than the median expression of IL-12A in a reference population.

iii(e). Tumor mutational Burden

In some aspects, the tumor mutational burden (TMB) of a sample from the tumor of the individual is quantified. The TMB may be a tissue TMB (tTMB) score or a blood TMB (bTMB) score. TMB may be determined using any suitable approach, for example, as described in Example 1 below or in International Patent Application Publication No. WO 2017/151524, in International Patent Application Publication No. WO 2018/068028 for tissue TMB (tTMB), and in International Patent Application Publication No. WO 2019/018757 for blood (bTMB), which are incorporated herein by reference in their entirety. In some aspects, the individual may have a TMB in a tumor or blood sample that is above a reference TMB. In other aspects, the individual may have a TMB that is below a reference TMB.

iii(f). Methods of Selecting a Therapy Using PRS and Tumor-Associated Factors

In some aspects, the PRS for vitiligo determined from a sample from an individual is above the vitiligo reference PRS and IC staining in a sample from the tumor of the individual is high (e.g., IC1, IC2, or IC3). In some aspects, the method further comprises administering to the individual an effective amount of an immune checkpoint inhibitor.

In some aspects, the PRS for psoriasis determined from a sample from an individual is above the psoriasis reference PRS and IC staining in a sample from the tumor of the individual is high (e.g., IC1, IC2, or IC3). In some aspects, the method further comprises administering to the individual an effective amount of an immune checkpoint inhibitor.

In some aspects, the PRS for vitiligo determined from a sample from an individual is above the vitiligo reference PRS; the PRS for psoriasis determined from a sample from an individual is above the psoriasis reference PRS; and IC staining in a sample from the tumor of the individual is high (e.g., IC1, IC2, or IC3). In some aspects, the method further comprises administering to the individual an effective amount of an immune checkpoint inhibitor.

In some aspects, the PRS for vitiligo determined from a sample from an individual is above the vitiligo reference PRS and the T-effector signature score in a sample from the tumor of the individual is high (e.g., greater that the median T-effector signature score of a reference population). In some aspects, the method further comprises administering to the individual an effective amount of an immune checkpoint inhibitor.

In some aspects, the PRS for psoriasis determined from a sample from an individual is above the psoriasis reference PRS and the T-effector signature score in a sample from the tumor of the individual is high (e.g., greater that the median T-effector signature score of a reference population). In some aspects, the method further comprises administering to the individual an effective amount of an immune checkpoint inhibitor.

In some aspects, the PRS for vitiligo determined from a sample from an individual is above the vitiligo reference PRS; the PRS for psoriasis determined from a sample from an individual is above the psoriasis reference PRS; and the T-effector signature score in a sample from the tumor of the individual is high (e.g., greater that the median T-effector signature score of a reference population). In some aspects, the method further comprises administering to the individual an effective amount of an immune checkpoint inhibitor.

In some aspects, the PRS for vitiligo determined from a sample from an individual is above the vitiligo reference PRS and the tumor sample of the individual is determined to have high Th17 function. In some aspects, high Th17 function is indicated by one, two, three, four, five, six, seven, eight, or all nine of high IC staining of PD-L1, high expression of CD8A, high expression of PRF1, high T-effector signature score, high expression of IL-23A, high expression of IL-12B, low expression of IL-12A, high expression of CXCL20, and high expression of CXCL2. In some aspects, the method further comprises administering to the individual an effective amount of an immune checkpoint inhibitor.

III. Methods of Treatment

A. Cancers

In some aspects, an immune checkpoint inhibitor is used to treat or delay progression of a cancer in a subject in need thereof. In some aspects, the subject is a human. The cancer may be a solid tumor cancer or a non-solid tumor cancer. Solid cancer tumors include, but are not limited to a bladder cancer, a melanoma, a breast cancer, a colorectal cancer, a lung cancer, a head and neck cancer, a kidney cancer, an ovarian cancer, a pancreatic cancer, or a prostate cancer, or metastatic forms thereof. In some aspects, the cancer is a bladder cancer. Further aspects of bladder cancer include urothelial carcinoma, muscle invasive bladder cancer (MIBC), or non-muscle invasive bladder cancer (NMIBC). In some aspects, the bladder cancer is a metastatic urothelial carcinoma (mUC). In some aspects, the cancer is a breast cancer. Further aspects of breast cancer include a hormone receptor-positive (HR+) breast cancer, e.g., an estrogen receptor-positive (ER+) breast cancer, a progesterone receptor-positive (PR+) breast cancer, or an ER+/PR+ breast cancer. Other aspects of breast cancer include a HER2-positive (HER2+) breast cancer. Yet other aspects of breast cancer include a triple-negative breast cancer (TNBC). In some aspects, the breast cancer is an early breast cancer. In some aspects, the cancer is a lung cancer. Further aspects of lung cancer include an epidermal growth factor receptor-positive (EGFR+) lung cancer. Other aspects of lung cancer include an epidermal growth factor receptor-negative (EGFR−) lung cancer. Yet other aspects of lung cancer include a non-small cell lung cancer, e.g., a squamous lung cancer or a non-squamous lung cancer. Other aspects of lung cancer include a small cell lung cancer. In some aspects, the cancer is a head and neck cancer. Further aspects of head and neck cancer include a squamous cell carcinoma of the head & neck (SCCHN). In some aspects, the cancer is a kidney cancer. Further aspects of kidney cancer include a renal cell carcinoma (RCC). In some aspects, the cancer is a liver cancer. Further aspects of liver cancer include a hepatocellular carcinoma. In some aspects, the cancer is a prostate cancer. Further aspects of prostate cancer include a castration-resistant prostate cancer (CRPC). In some aspects, the cancer is a metastatic form of a solid tumor. In some aspects, the metastatic form of a solid tumor is a metastatic form of a melanoma, a breast cancer, a colorectal cancer, a lung cancer, a head and neck cancer, a bladder cancer, a kidney cancer, an ovarian cancer, a pancreatic cancer, or a prostate cancer. In some aspects, the cancer is a metastatic urothelial carcinoma (mUC). In some aspects, the cancer is a non-solid tumor cancer. Non-solid tumor cancers include, but are not limited to, a B-cell lymphoma. Further aspects of B-cell lymphoma include, e.g., a chronic lymphocytic leukemia (CLL), a diffuse large B-cell lymphoma (DLBCL), a follicular lymphoma, myelodysplastic syndrome (MDS), a non-Hodgkin lymphoma (NHL), an acute lymphoblastic leukemia (ALL), a multiple myeloma, an acute myeloid leukemia (AML), or a mycosis fungoides (MF).

B. Immune Checkpoint Inhibitors

In some aspects, an immune checkpoint inhibitor, for example, a PD-L1 axis binding antagonist, includes a PD-1 binding antagonist, a PD-L1 binding antagonist, and a PD-L2 binding antagonist. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. PD-L1 (programmed death ligand 1) is also referred to in the art as "programmed cell death 1 ligand 1," "PDCD1LG1," "CD274," "B7-H," and "PDL1." An exemplary human PD-L1 is shown in UniProtKB/Swiss-Prot Accession No. Q9NZQ7.1. PD-L2 (programmed death ligand 2) is also referred to in the art as "programmed cell death 1 ligand 2," "PDCD1LG2," "CD273," "B7-DC," "Btdc," and "PDL2." An exemplary human PD-L2 is shown in UniProtKB/Swiss-Prot Accession No. Q9BQ51. In some instances, PD-1, PD-L1, and PD-L2 are human PD-1, PD-L1 and PD-L2.

In some aspects, the PD-1 binding antagonist is a molecule that inhibits the binding of PD-1 to its ligand binding partners. In a specific aspect the PD-1 ligand binding partners are PD-L1 and/or PD-L2. In another instance, a PD-L1 binding antagonist is a molecule that inhibits the binding of PD-L1 to its binding ligands. In a specific aspect, PD-L1 binding partners are PD-1 and/or B7-1. In another instance, the PD-L2 binding antagonist is a molecule that inhibits the binding of PD-L2 to its ligand binding partners. In a specific aspect, the PD-L2 binding ligand partner is PD-1. The antagonist may be an antibody, an antigen binding fragment thereof, an immunoadhesin, a fusion protein, or oligopeptide.

In some aspects, the PD-1 binding antagonist is an anti-PD-1 antibody (e.g., a human antibody, a humanized antibody, or a chimeric antibody), for example, as described below. In some aspects, the anti-PD-1 antibody is selected from the group consisting of MDX-1106 (nivolumab), MK-3475 (pembrolizumab), MEDI-0680 (AMP-514), PDR001, REGN2810, and BGB-108. MDX-1106, also known as MDX-1106-04, ONO-4538, BMS-936558, or nivolumab, is an anti-PD-1 antibody described in WO2006/121168. MK-3475, also known as pembrolizumab or lambrolizumab, is an anti-PD-1 antibody described in WO 2009/114335. In some instances, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some instances, the PD-1 binding antagonist is AMP-224. AMP-224, also known as B7-DCIg, is a PD-L2-Fc fusion soluble receptor described in WO 2010/027827 and WO 2011/066342.

In some aspects, the anti-PD-1 antibody is MDX-1106. Alternative names for "MDX-1106" include MDX-1106-04, ONO-4538, BMS-936558, and nivolumab. In some aspects, the anti-PD-1 antibody is nivolumab (CAS Registry Number: 946414-94-4). In a still further aspect, provided is an isolated anti-PD-1 antibody comprising a heavy chain variable region comprising the heavy chain variable region amino acid sequence from SEQ ID NO: 1 and/or a light chain variable region comprising the light chain variable region amino acid sequence from SEQ ID NO: 2. In a still further aspect, provided is an isolated anti-PD-1 antibody comprising a heavy chain and/or a light chain sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

(SEQ ID NO: 1)
QVQLVESGGGVVQPGRSLRLDCKASGITFSNSGMHWVRQAPGKGLEWV

AVIWYDGSKRYYADSVKGRFTISRDNSKNTLFLQMNSLRAEDTAVYYC

ATNDDYWGQGTLVTVSSASTKGPSVFPLAPCSRSTSESTAALGCLVKD

YFPEPVTVSWNSGALTSGVHTFPAVLQSSGLYSLSSVVTVPSSSLGTK

TYTCNVDHKPSNTKVDKRVESKYGPPCPPCPAPEFLGGPSVFLFPPKP

KDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQK

SLSLSLGK, and (b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 2)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some aspects, the PD-L1 axis binding antagonist is a PD-L2 binding antagonist. In some aspects, the PD-L2 binding antagonist is an anti-PD-L2 antibody (e.g., a human antibody, a humanized antibody, or a chimeric antibody). In some aspects, the PD-L2 binding antagonist is an immunoadhesin.

In some aspects, the PD-L1 binding antagonist is an anti-PD-L1 antibody, for example, as described below. In some aspects, the anti-PD-L1 antibody is capable of inhibiting binding between PD-L1 and PD-1 and/or between PD-L1 and B7-1. In some aspects, the anti-PD-L1 antibody is a monoclonal antibody. In some aspects, the anti-PD-L1 antibody is an antibody fragment selected from the group consisting of Fab, Fab'-SH, Fv, scFv, and (Fab')$_2$ fragments. In some aspects, the anti-PD-L1 antibody is a humanized antibody. In some aspects, the anti-PD-L1 antibody is a human antibody. In some aspects, the anti-PD-L1 antibody is selected from the group consisting of YW243.55.S70, MPDL3280A (atezolizumab), MDX-1105, and MEDI4736 (durvalumab), and MSB0010718C (avelumab). Antibody YW243.55.S70 is an anti-PD-L1 described in WO 2010/077634. MDX-1105, also known as BMS-936559, is an anti-PD-L1 antibody described in WO2007/005874. MEDI4736 (durvalumab) is an anti-PD-L1 monoclonal antibody described in WO2011/066389 and US2013/034559. Examples of anti-PD-L1 antibodies useful for the methods of this invention, and methods for making thereof are described in PCT patent application WO 2010/077634, WO 2007/005874, WO 2011/066389, U.S. Pat. No. 8,217,149, and US 2013/034559, which are incorporated herein by reference.

Anti-PD-L1 antibodies described in WO 2010/077634 A1 and U.S. Pat. No. 8,217,149 may be used in the methods described herein. In some aspects, the anti-PD-L1 antibody comprises a heavy chain variable region sequence of SEQ ID NO: 3 and/or a light chain variable region sequence of SEQ ID NO: 4. In a still further aspect, provided is an isolated anti-PD-L1 antibody comprising a heavy chain variable region and/or a light chain variable region sequence, wherein:

(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

(SEQ ID NO: 3)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS, and (b) the light chain sequence has at least 85%, at least 90%, at least 91%, at least 92%, at least 93%, at least 94%, at least 95%, at least 96%, at least 97%, at least 98%, at least 99% or 100% sequence identity to the light chain sequence:

(SEQ ID NO: 4)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

In one aspect, the anti-PD-L1 antibody comprises a heavy chain variable region comprising an HVR-H1, HVR-H2 and HVR-H3 sequence, wherein:

(a) the HVR-H1 sequence is GFTFSX$_1$SWIH (SEQ ID NO: 5);
(b) the HVR-H2 sequence is AWIX$_2$PYGGSX$_3$YYADSVKG (SEQ ID NO: 6);
(c) the HVR-H3 sequence is RHWPGGFDY (SEQ ID NO: 7);

further wherein: X$_1$ is D or G; X$_2$ is S or L; X$_3$ is T or S. In one specific aspect, X$_1$ is D; X$_2$ is S and X3 is T. In another aspect, the polypeptide further comprises variable region heavy chain framework sequences juxtaposed between the HVRs according to the formula: (FR-H1)-(HVR-H1)-(FR-H2)-(HVR-H2)-(FR-H3)-(HVR-H3)-(FR-H4). In yet another aspect, the framework sequences are derived from human consensus framework sequences. In a further aspect, the framework sequences are VH subgroup III consensus framework. In a still further aspect, at least one of the framework sequences is the following:

```
                                           (SEQ ID NO: 8)
FR-H1 is EVQLVESGGGLVQPGGSLRLSCAAS (SEQ ID NO: 9)
FR-H2 is WVRQAPGKGLEWV (SEQ ID NO: 10)
FR-H3 is RFTISADTSKNTAYLQMNSLRAEDTAVYYCAR (SEQ ID NO: 11)
FR-H4 is WGQGTLVTVSS.
```

In a still further aspect, the heavy chain polypeptide is further combined with a variable region light chain comprising an HVR-L1, HVR-L2 and HVR-L3, wherein:

```
                                           (SEQ ID NO: 12)
(a) the HVR-L1 sequence is RASQX₄X₅X₆TX₇X₈A;

(SEQ ID NO: 13)
(b) the HVR-L2 sequence is SASX₉LX₁₀S,;

(SEQ ID NO: 14)
(c) the HVR-L3 sequence is QQX₁₁X₁₂X₁₃X₁₄PX₁₅T;
``` wherein: $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a still further aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A.

In a still further aspect, the light chain further comprises variable region light chain framework sequences juxtaposed between the HVRs according to the formula: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the framework sequences are VL kappa I consensus framework. In a still further aspect, at least one of the framework sequence is the following:

```
                                           (SEQ ID NO: 15)
FR-L1 is DIQMTQSPSSLSASVGDRVTITC (SEQ ID NO: 16)
FR-L2 is WYQQKPGKAPKLLIY (SEQ ID NO: 17)
FR-L3 is GVPSRFSGSGSGTDFTLTISSLQPEDFATYYC (SEQ ID NO: 18)
FR-L4 is FGQGTKVEIKR.
```

In another aspect, provided is an isolated anti-PD-L1 antibody or antigen binding fragment comprising a heavy chain and a light chain variable region sequence, wherein:
(a) the heavy chain comprises an HVR-H1, HVR-H2 and HVR-H3, wherein further:

```
                                           (SEQ ID NO: 5)
(i) the HVR-H1 sequence is GFTFSX₁SWIH;

(SEQ ID NO: 6)
(ii) the HVR-H2 sequence is AWIX₂PYGGSX₃YYADSVKG (SEQ ID NO: 7)
(iii) the HVR-H3 sequence is RHWPGGFDY,
and
```

(b) the light chain comprises an HVR-L1, HVR-L2 and HVR-L3, wherein further:

```
                                           (SEQ ID NO: 12)
(i) the HVR-L1 sequence is RASQX₄X₅X₆TX₇X₈A (SEQ ID NO: 13)
(ii) the HVR-L2 sequence is SASX₉LX₁₀S;
and (SEQ ID NO: 14)
(iii) the HVR-L3 sequence is QQX₁₁X₁₂X₁₃X₁₄PX₁₅T;
``` wherein: $X_1$ is D or G; $X_2$ is S or L; $X_3$ is T or S; $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T. In a specific aspect, $X_1$ is D; $X_2$ is S and $X_3$ is T. In another aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs: 8, 9, 10, and 11. In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs: 15, 16, 17, and 18.

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further aspect, the effector-less Fc mutation is an N297A or D265A/N297A substitution in the constant region.

In yet another aspect, provided is an anti-PD-L1 antibody comprising a heavy chain and a light chain variable region sequence, wherein:
(a) the heavy chain further comprises an HVR-H1, HVR-H2 and an HVR-H3 sequence having at least 85% sequence identity to GFTFSDSWIH (SEQ ID NO: 19), AWISPYGGSTYYADSVKG (SEQ ID NO: 20) and RHWPGGFDY (SEQ ID NO: 21), respectively, or
(b) the light chain further comprises an HVR-L1, HVR-L2 and an HVR-L3 sequence having at least 85% sequence identity to RASQDVSTAVA (SEQ ID NO:

22), SASFLYS (SEQ ID NO: 23) and QQYLYHPAT (SEQ ID NO: 24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs: 8, 9, 10, and 11. In a still further aspect, the light chain framework sequences are derived from a Kabat kappa I, II, II, or IV subgroup sequence. In a still further aspect, the light chain framework sequences are VL kappa I consensus framework. In a still further aspect, one or more of the light chain framework sequences are set forth as SEQ ID NOs: 15, 16, 17, and 18.

In a further aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                              (SEQ ID NO: 27)
FR-H1  EVQLVESGGGLVQPGGSLRLSCAASGFTFS (SEQ ID NO: 28)
FR-H2  WVRQAPGKGLEWVA (SEQ ID NO: 10)
FR-H3  RFTISADTSKNTAYLQMNSLRAEDTAVYYCAR (SEQ ID NO: 11)
FR-H4  WGQGTLVTVSS.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                              (SEQ ID NO: 15)
FR-L1  DIQMTQSPSSLSASVGDRVTITC (SEQ ID NO: 16)
FR-L2  WYQQKPGKAPKLLIY
```

-continued
```
                                              (SEQ ID NO: 17)
FR-L3  GVPSRFSGSGSGTDFTLTISSLQPEDFATYYC (SEQ ID NO: 26)
FR-L4  FGQGTKVEIK.
```

In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further aspect, the effector-less Fc mutation is an N297A or D265A/N297A substitution in the constant region.

In yet another aspect, provided is an anti-PD-L1 antibody comprising a heavy chain and a light chain variable region sequence, wherein:
(c) the heavy chain further comprises an HVR-H1, HVR-H2 and an HVR-H3 sequence having at least 85% sequence identity to GFTFSDSWIH (SEQ ID NO: 19), AWISPYGGSTYYADSVKG (SEQ ID NO: 20) and RHWPGGFDY (SEQ ID NO: 21), respectively, and/or
(d) the light chain further comprises an HVR-L1, HVR-L2 and an HVR-L3 sequence having at least 85% sequence identity to RASQDVSTAVA (SEQ ID NO: 22), SASFLYS (SEQ ID NO: 23) and QQYLYHPAT (SEQ ID NO: 24), respectively.

In a specific aspect, the sequence identity is 86%, 87%, 88%, 89%, 90%, 91%, 92%, 93%, 94%, 95%, 96%, 97%, 98%, 99% or 100%.

In another aspect, the heavy chain variable region comprises one or more framework sequences juxtaposed between the HVRs as: (FR-H1)-(HVR-H1)-(FR-H2)-(HVR-H2)-(FR-H3)-(HVR-H3)-(FR-H4), and the light chain variable regions comprises one or more framework sequences juxtaposed between the HVRs as: (FR-L1)-(HVR-L1)-(FR-L2)-(HVR-L2)-(FR-L3)-(HVR-L3)-(FR-L4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences are set forth as SEQ ID NOs: 8, 9, 10, and WGQGTLVTVSSASTK (SEQ ID NO: 29).

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences are set forth as SEQ ID NOs: 15, 16, 17, and 18. In a still further specific aspect, the antibody further comprises a human or murine constant region. In a still further aspect, the human constant region is selected from the group consisting of IgG1, IgG2, IgG2, IgG3, and IgG4. In a still further specific aspect, the human constant region is IgG1. In a still further aspect, the murine constant region is selected from the group consisting of IgG1, IgG2A, IgG2B, and IgG3. In a still further aspect, the murine constant region in IgG2A. In a still further specific aspect, the antibody has reduced or minimal effector function. In a still further specific aspect the minimal effector function results from an "effector-less Fc mutation" or aglycosylation. In still a further aspect, the effector-less Fc mutation is an N297A or D265A/N297A substitution in the constant region.

In a still further aspect, provided is an isolated anti-PD-L1 antibody comprising a heavy chain and a light chain variable region sequence, wherein:

(a) the heavy chain sequence has at least 85% sequence identity to the heavy chain sequence:

(SEQ ID NO: 25)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTK, or
(b) the light chain sequences has at least 85% sequence identity to the light chain sequence:

(SEQ ID NO: 4)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.

In some aspects, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 4. In some aspects, provided is an isolated anti-PD-L1 antibody comprising a heavy chain and a light chain variable region sequence, wherein the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence of SEQ ID NO: 25. In some aspects, provided is an isolated anti-PD-L1 antibody comprising a heavy chain and a light chain variable region sequence, wherein the light chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 4 and the heavy chain variable region sequence has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 25. In some aspects, one, two, three, four, or five amino acid residues at the N-terminal of the heavy and/or light chain may be deleted, substituted or modified.

In a still further aspect, provided is an isolated anti-PD-L1 antibody comprising a heavy chain and a light chain sequence, wherein:

(a) the heavy chain sequence has at least 85% sequence identity to the heavy chain sequence:

(SEQ ID NO: 30)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG, and/or
(b) the light chain sequences has at least 85% sequence identity to the light chain sequence:

(SEQ ID NO: 31)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.

In some aspects, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 31. In some aspects, provided is an isolated anti-PD-L1 antibody comprising a heavy chain and a light chain sequence, wherein the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 30. In some aspects, provided is an isolated anti-PD-L1 antibody comprising a heavy chain and a light chain sequence, wherein the light chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 31 and the heavy chain sequence has at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence of SEQ ID NO: 30.

In some aspects, the isolated anti-PD-L1 antibody is aglycosylated. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Removal of glycosylation sites form an antibody is conveniently accomplished by altering the amino acid sequence such that one of the above-described tripeptide sequences (for N-linked glycosylation sites) is removed. The alteration may be made by substitution of an asparagine, serine or threonine residue within the glycosylation site another amino acid residue (e.g., glycine, alanine or a conservative substitution).

In any of the aspects herein, the isolated anti-PD-L1 antibody can bind to a human PD-L1, for example a human PD-L1 as shown in UniProtKB/Swiss-Prot Accession No. Q9NZQ7.1, or a variant thereof.

In a still further aspect, provided is an isolated nucleic acid encoding any of the antibodies described herein. In some aspects, the nucleic acid further comprises a vector suitable for expression of the nucleic acid encoding any of the previously described anti-PD-L1 antibodies. In a still further specific aspect, the vector is in a host cell suitable for expression of the nucleic acid. In a still further specific aspect, the host cell is a eukaryotic cell or a prokaryotic cell. In a still further specific aspect, the eukaryotic cell is a mammalian cell, such as Chinese hamster ovary (CHO) cell.

The antibody or antigen binding fragment thereof, may be made using methods known in the art, for example, by a process comprising culturing a host cell containing nucleic acid encoding any of the previously described anti-PD-L1 antibodies or antigen-binding fragments in a form suitable for expression, under conditions suitable to produce such antibody or fragment, and recovering the antibody or fragment.

It is expressly contemplated that such PD-L1 axis binding antagonist antibodies (e.g., anti-PD-L1 antibodies, anti-PD-1 antibodies, and anti-PD-L2 antibodies), or other antibodies described herein for use in any of the aspects enumerated above may have any of the features, singly or in combination.

In some aspects, the immune checkpoint inhibitor is an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof.

In some aspects, the immune checkpoint inhibitor is an antagonist directed against TIGIT (e.g., an anti-TIGIT antibody). Exemplary anti-TIGIT antibodies are described in US Patent Application Publication No. 2018/0186875 and in International Patent Application Publication No. WO 2017/053748, which are incorporated herein by reference in their entirety.

C. Methods of Delivery

The compositions utilized in the methods described herein (e.g., immune checkpoint inhibitors) can be administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularlly, mucosally, intrapericardially, intraumbilically, intraocularly, intraorbitally, orally, topically, transdermally, intravitreally (e.g., by intravitreal injection), by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some aspects, an immune checkpoint inhibitor (e.g., a PD-L1 axis binding antagonist, e.g., atezolizumab) is administered intravenously, intramuscularly, subcutaneously, topically, orally, transdermally, intraperitoneally, intraorbitally, by implantation, by inhalation, intrathecally, intraventricularly, or intranasally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Immune checkpoint inhibitors (e.g., an immune checkpoint inhibitor described in Section IIIB herein, e.g., an antibody, binding polypeptide, and/or small molecule) described herein (and any additional therapeutic agent) may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The immune checkpoint inhibitor need not be, but is optionally formulated with and/or administered concurrently with one or more agents currently used to prevent or treat the disorder in question, e.g., one or more of the agents provided in Section IIID herein. The effective amount of such other agents depends on the amount of the immune checkpoint inhibitor present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the treatment of a cancer, e.g., a cancer described in Section IIIA herein, the appropriate dosage of an immune checkpoint inhibitor, e.g., a PD-L1 axis binding antagonist, an antagonist directed against a co-inhibitory molecule (e.g., a CTLA-4 antagonist (e.g., an anti-CTLA-4 antibody), a TIM-3 antagonist (e.g., an anti-TIM-3 antibody), or a LAG-3 antagonist (e.g., an anti-LAG-3 antibody)), or any combination thereof, described herein (when used alone or in combination with one or more other additional therapeutic agents) will depend on the type of disease to be treated, the severity and course of the disease, whether the PD-L1 axis binding antagonist is administered for preventive or therapeutic purposes, previous therapy, the patient's clinical history and response to the PD-L1 axis binding antagonist, and the discretion of the attending physician. The immune checkpoint inhibitor is suitably administered to the patient at one time or over a series of treatments. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g., every week or every three weeks (e.g., such that the patient receives, for example, from about two to about twenty, or e.g., about six doses of the immune checkpoint inhibitor). An initial higher loading dose, followed by one or more lower doses, may be administered. However, other dosage regimens may be useful. The progress of this therapy is easily monitored by conventional techniques and assays.

For example, as a general proposition, the therapeutically effective amount of an immune checkpoint inhibitor, for example, a PD-L1 axis binding antagonist antibody, an anti-CTLA-4 antibody, an anti-TIM-3 antibody, or an anti-LAG-3 antibody, administered to human will be in the range of about 0.01 to about 50 mg/kg of patient body weight, whether by one or more administrations. In some aspects, the antibody used is about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg administered daily, weekly, every two weeks, every three weeks, or monthly, for example. In some aspects, the antibody is administered at 15 mg/kg. However, other dosage regimens may be useful. In one aspect, an anti-PD-L1 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, or about 1800 mg on day 1 of 21-day cycles (every three weeks, q3w). In some aspects, anti-PD-L1 antibody MPDL3280A is administered at 1200 mg intravenously every three weeks (q3w). The dose may be administered as a single dose or as multiple doses (e.g., 2 or 3 doses), such as infusions. The dose of the antibody administered in a combination treatment may be reduced as compared to a single treatment. The progress of this therapy is easily monitored by conventional techniques.

In some aspects, the individual has not been previously treated for the cancer. In some aspects, the individual has not been previously administered an immune checkpoint inhibitor.

D. Additional Therapeutic Agents

In some aspects, the immune checkpoint inhibitor used with one or more additional therapeutic agents, e.g., a combination therapy. In some aspects, the composition comprising the immune checkpoint inhibitor further comprises the additional therapeutic agent. In another aspect, the additional therapeutic agent is delivered in a separate composition. In some aspects, the one or more additional therapeutic agents comprise an immunomodulatory agent, an anti-neoplastic agent, a chemotherapeutic agent, a growth inhibitory agent, an anti-angiogenic agent, a radiation therapy, a cytotoxic agent, a cell-based therapy, or a combination thereof.

Combination therapies as described above encompass combined administration (wherein two or more therapeutic agents are included in the same or separate formulations) and separate administration (wherein administration of an immune checkpoint inhibitor (e.g., an immune checkpoint inhibitor described in Section IIIB herein, e.g., a PD-L1 axis binding antagonist) can occur prior to, simultaneously, and/or following, administration of the additional therapeutic agent or agents). In one aspect, administration of an immune checkpoint inhibitor and administration of an additional therapeutic agent occur within about one month, or within about one, two or three weeks, or within about one, two, three, four, five, or six days, of each other.

i. Immunomodulatory Agents

In some aspects, the additional therapeutic agent is an immunomodulatory agent. In some aspects, the immunomodulatory agent is a T cell-dependent bispecific antibody or an mRNA-based personalized cancer vaccine (PCV).

ia. T-Cell-Dependent Bispecific Antibodies (TDBs)

In some aspects, the immunomodulatory agent is a T-cell-dependent bispecific antibody (TDB). In some aspects, the TDB may bind to two different epitopes of the T cell marker CD3 (e.g., CD3ε or CD3γ). In other aspects, the TDB may bind to two different targets, one of which is CD3, and the other of which is a second biological molecule, e.g., a cell surface antigen, e.g., a tumor antigen. Exemplary tumor antigens are described in U.S. Pub. No. 2010/0111856.

ib. T-Cell Receptor Bispecific Targeting Domains

In some aspects, the immunomodulatory agent is a T-cell receptor bispecific. In some aspects, the T cell receptor bispecific comprises a first region comprising a T cell receptor ("TCR"). In some aspects, the TCR binds to a pMHC epitope. In some aspects, the T cell receptor bispecific further comprises a targeting domain that binds to a tumor antigen. In some aspects, the T-cell receptor bispecific is an Immune mobilizing monoclonal T-cell receptor Against Cancer (ImmTAC). (Oates and Jakobsen, *OncoImmunology*, 2 (2), 2013; WO2010133828).

ic. NK-Engaging Bispecific Targeting Domains

In some aspects, the immunomodulatory agent is a NK-engaging bispecific. In some aspects, the NK-engaging bispecific comprises a first targeting domain binding to an epitope on a NK cell and a second targeting domain binding to a different target, e.g., a tumor antigen. In some aspects, the NK-engaging bispecific comprises a first targeting domain binding CD16a, a protein expressed on the surface of NK cells, and a second targeting domain binding the tumor marker CD30. In some aspects, the NK-engaging bispecific is an NK cell TandB®. In some aspects, the NK cell TandB® is AFM13 (Reusch et al., *mAbs,* 6 (3): 727-738; 2014; U.S. Pat. No. 7,129,330B1; U.S. Pat. No. 9,035, 026B2; WO0111059A1). In some aspects, the NK-engaging bispecific comprises a first targeting domain binding CD16a and a second targeting domain binding epidermal growth factor receptor (EGFR) or EGFRvIII. In some aspects, the NK cell TandB® is AFM24. (Treder et al., *Journal of Clinical Oncology,* 34 (15 suppl), 2016; Ellwanger et al., *J Immunother Cancer,* 3 (Suppl 2): 219, 2015). In some aspects, the NK-engaging bispecific comprises a first targeting domain binding NKp46 and a second targeting domain binding a tumor antigen.

id. Personalized Cancer Vaccines (PCVs)

In some aspects, the immunomodulatory agent is a personalized cancer vaccine (PCV). PCV is a method of treatment comprising inducing in a patient an immune response against one or more (e.g., 1, 2, 3, 4, 5. 10, 15, 20, 30, 40, 50, 100, 200, 300, 400, 500, or more than 500) cancer-specific somatic mutations present in cancer cells of the patient, as described, for example, in PCT Pub. Nos. WO2014/082729 and WO2012/159754, which are incorporated by reference herein in their entirety.

In some aspects, the immune response is against one or more (e.g., 1, 2, 3, 4, 5. 10, 15, 20, 30, 40, 50, 100, 200, 300, 400, 500, or more than 500) individual tumor mutations. It is estimated that 30-400 protein-changing somatic mutations, which may result in tumor-specific T cell epitopes, are present in a human cancer cell. These mutations comprise a patient's individual cancer mutation "signature" (WO2014/082729). Mutations may be collected from tumor cells, e.g., circulating tumor cells (CTCs), which may be isolated from, e.g., a biopsy or a blood sample. In some aspects, mutations are determined by comparing DNA sequences in healthy versus cancerous cells using next-generation sequencing. The transcriptome (RNA) may also be sequenced to determine which proteins are expressed by the cancer cells (WO2012/159754). Mutation-based antigens (or epitopes thereof) thus identified may be encoded by a nucleic acid, e.g., an RNA, e.g., an in vitro transcribed RNA. Said antigens or epitopes may be spaced by linkers or lined up head-to-tail (WO2014/082729).

In some aspects, treatment with the PCV may comprise inducing in a patient a first immune response against one or more tumor antigens and a second immune response against one or more mutation-based antigens as described above (WO2014/082729). The first and second immune responses may be administered simultaneously or sequentially. In some aspects, the first immune response is against a tumor antigen (e.g., a TAA) prevalent in multiple cancers or in the cancer to be treated. Induction of the first immune response may comprise, e.g., administration of one or more vaccine products selected from a set comprising pre-manufactured vaccine products, e.g., an RNA encoding a polypeptide comprising a tumor antigen or a fragment thereof (WO2014/082729).

ie. Antibodies Targeting a Tumor Antigen, an Immune Checkpoint Protein, or a Lymphocyte Receptor In some aspects, the immunomodulatory agent is an antibody or antibody fragment targeting a lymphocyte receptor (e.g., a marker of T cells such as one described in section Ki herein, a T cell receptor protein such as one described in section Ki herein, or a marker of NK cells such as one described in section Ki herein), a dendritic cell receptor such as one described in section Kii herein, a tumor antigen such as one described in section Kiii herein, an immune checkpoint component such as one described in section Liv herein, or a T cell agonist or antagonist such as one described in section Kv herein.

ii. Chemotherapeutic Agents

In some aspects, the additional therapeutic agent is a chemotherapeutic agent. A chemotherapeutic agent is a chemical compound useful in the treatment of cancer. Exemplary chemotherapeutic agents include, but are not limited to erlotinib (TARCEVA®, Genentech/OSI Pharm.), anti-hormonal agents that act to regulate or inhibit hormone action on tumors such as anti-estrogens and selective estrogen receptor modulators (SERMs), antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), or trastuzumab (HERCEPTIN®, Genentech), EGFR inhibitors (EGFR antagonists), tyrosine kinase inhibitors, and chemotherapeutic agents also include non-steroidal anti-inflammatory drugs (NSAIDs) with analgesic, antipyretic and anti-inflammatory effects.

iii. Growth Inhibitory Agents

In some aspects, the additional therapeutic agent is a growth inhibitory agent. Exemplary growth inhibitory agents include agents that block cell cycle progression at a place other than S phase, e.g., agents that induce G1 arrest (e.g., DNA alkylating agents such as tamoxifen, prednisone, dacarbazine, mechlorethamine, cisplatin, methotrexate, 5-fluorouracil, or ara-C) or M-phase arrest (e.g., vincristine, vinblastine, taxanes (e.g., paclitaxel and docetaxel), doxorubicin, epirubicin, daunorubicin, etoposide, or bleomycin).

iv. Radiation Therapies

In some aspects, the additional therapeutic agent is a radiation therapy. Radiation therapies include the use of directed gamma rays or beta rays to induce sufficient damage to a cell so as to limit its ability to function normally or to destroy the cell altogether. Typical treatments are given as a one-time administration and typical dosages range from 10 to 200 units (Grays) per day.

v. Cytotoxic Agents

In some aspects, the additional therapeutic agent is a cytotoxic agent, e.g., a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$, and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and antitumor or anticancer agents.

vi. Cell-Based Therapies

The additional therapeutic agent may by a cell-based therapy, e.g., an adoptive cell transfer (ACT) therapy. Cell-based therapies include CAR-T, NAR-T, and NEO-T.

The immunomodulatory agent may be a T cell transduced with a chimeric antigen receptor (CAR-T). In some aspects, the immunomodulatory agent is a natural killer cell transduced with a chimeric antigen receptor (NAR-T; CAR-NK). In some aspects, the chimeric antigen receptor (CAR) comprises an antigen-binding domain (e.g., an antibody or a fragment thereof; a T-cell receptor (TCR) or a fragment thereof) binding to a tumor antigen, a transmembrane domain, and one or more intracellular signaling domains, e.g., a primary signaling domain (e.g., CD3ζ) and/or a costimulatory signaling domain (e.g., CD28, 4-1BB) (WO2017-114497; Hartmann et al., *EMBO Molecular Medicine*, 9 (9), 2017). The intracellular signaling domain may act to activate cytotoxicity.

In some aspects, the CAR is introduced into a population of immune effector cells, e.g., T cells or NK cells. The population of immune effector cells may be prepared for CAR, e.g., by use of a flow-through module, as described in WO2017117112. The immune effector cells may be autologous, e.g., deriving from the patient, or allogenic, e.g., derived from a donor. In some aspects, CAR-T and NAR-T cells are introduced to a patient intravenously or intratumorally.

In some aspects, the immunomodulatory agent is a neoantigen T cell (NEO-T) therapy. In some aspects, the immunomodulatory agent is a T cell transduced with a native TCR specific to a tumor neoantigen ("neoantigen-specific TCR"). In some aspects, the tumor neoantigen is prevalent in multiple cancers or in the cancer to be treated. In other aspects, the tumor neoantigen is specific to the cancer of an individual patient. In some aspects, the neoantigen-specific TCR is discovered by sequencing of an individual patient's TCRs.

In some aspects, the neoantigen-specific TCR is introduced into a population of T cells. In some aspects, the T cells are autologous. In some aspects, the native TCR is replaced by the neoantigen-specific TCR using gene editing technology.

In some instances, the methods include administering to the individual an anti-cancer therapy other than, or in addition to, an immune checkpoint inhibitor, for example, a PD-L1 axis binding antagonist (e.g., an anti-neoplastic agent, a chemotherapeutic agent, a growth inhibitory agent, an anti-angiogenic agent, a radiation therapy, or a cytotoxic agent).

In some instances, the methods further involve administering to the patient an effective amount of an additional therapeutic agent. In some instances, the additional therapeutic agent is selected from the group consisting of an anti-neoplastic agent, a chemotherapeutic agent, a growth inhibitory agent, an anti-angiogenic agent, a radiation therapy, a cytotoxic agent, and combinations thereof. In some instances, an immune checkpoint inhibitor, for example, a PD-L1 axis binding antagonist, may be administered in conjunction with a chemotherapy or chemotherapeutic agent. In some instances, an immune checkpoint inhibitor, for example, a PD-L1 axis binding antagonist, may be administered in conjunction with a radiation therapy agent. In some instances, an immune checkpoint inhibitor, for example, a PD-L1 axis binding antagonist, may be administered in conjunction with a targeted therapy or targeted therapeutic agent. In some instances, an immune checkpoint inhibitor, for example, a PD-L1 axis binding antagonist, may be administered in conjunction with an immunotherapy or immunotherapeutic agent, for example a monoclonal antibody. In some instances, the additional therapeutic agent is an agonist directed against a co-stimulatory molecule. In some instances, the additional therapeutic agent is an antagonist directed against a co-inhibitory molecule. In some instances, the PD-L1 axis binding antagonist is administered as a monotherapy.

Such combination therapies noted above encompass combined administration (where two or more therapeutic agents are included in the same or separate formulations), and separate administration, in which case, administration of an immune checkpoint inhibitor, for example, a PD-L1 axis binding antagonist, can occur prior to, simultaneously, and/or following, administration of the additional therapeutic agent or agents. In one instance, administration of PD-L1 axis binding antagonist and administration of an additional therapeutic agent occur within about one month, or within about one, two or three weeks, or within about one, two, three, four, five, or six days, of each other.

Without wishing to be bound to theory, it is thought that enhancing T-cell stimulation, by promoting a co-stimulatory molecule or by inhibiting a co-inhibitory molecule, may promote tumor cell death thereby treating or delaying progression of cancer. In some instances, an immune checkpoint inhibitor, e.g., an immune checkpoint inhibitor described in Section IIIB herein, may be administered in conjunction with an agonist directed against a co-stimulatory molecule. In some instances, a co-stimulatory molecule may include CD40, CD226, CD28, OX40, GITR, CD137, CD27, HVEM, or CD127. In some instances, the agonist directed against a co-stimulatory molecule is an agonist antibody that binds to CD40, CD226, CD28, OX40, GITR, CD137, CD27, HVEM, or CD127. In some instances, an immune checkpoint inhibitor, for example, a PD-L1 axis binding antagonist, may be administered in conjunction with an antagonist directed against a co-inhibitory molecule. In some instances, a co-inhibitory molecule may include CTLA-4 (also known as CD152), TIM-3, BTLA, VISTA, LAG-3, B7-H3, B7-H4, IDO, TIGIT, MICA/B, or arginase. In some instances, the antagonist directed against a co-inhibitory molecule is an antagonist antibody that binds to CTLA-4, TIM-3, BTLA, VISTA, LAG-3, B7-H3, B7-H4, IDO, TIGIT, MICA/B, or arginase.

In some instances, a PD-L1 axis binding antagonist may be administered in conjunction with an antagonist directed against CTLA-4 (also known as CD152), e.g., a blocking antibody. In some instances, a PD-L1 axis binding antagonist may be administered in conjunction with ipilimumab (also known as MDX-010, MDX-101, or YERVOY®). In some instances, a PD-L1 axis binding antagonist may be administered in conjunction with tremelimumab (also known as ticilimumab or CP-675,206). In some instances, a PD-L1 axis binding antagonist may be administered in conjunction with an antagonist directed against B7-H3 (also known as CD276), e.g., a blocking antibody. In some instances, a PD-L1 axis binding antagonist may be administered in conjunction with MGA271. In some instances, a PD-L1 axis binding antagonist may be administered in conjunction with an antagonist directed against a TGF-beta, e.g., metelimumab (also known as CAT-192), fresolimumab (also known as GC1008), or LY2157299.

In some instances, an immune checkpoint inhibitor, for example, a PD-L1 axis binding antagonist, may be administered in conjunction with a treatment comprising adoptive transfer of a T-cell (e.g., a cytotoxic T-cell or CTL) expressing a chimeric antigen receptor (CAR). In some instances, an immune checkpoint inhibitor, for example, a PD-L1 axis binding antagonist, may be administered in conjunction with a treatment comprising adoptive transfer of a T-cell comprising a dominant-negative TGF beta receptor, e.g., a dominant-negative TGF beta type II receptor. In some instances, an immune checkpoint inhibitor, for example, a PD-L1 axis binding antagonist, may be administered in conjunction with a treatment comprising a HERCREEM protocol (see, e.g., ClinicalTrials.gov Identifier NCT00889954).

In some instances, an immune checkpoint inhibitor, for example, a PD-L1 axis binding antagonist, may be administered in conjunction with an agonist directed against CD137 (also known as TNFRSF9, 4-1BB, or ILA), e.g., an activating antibody. In some instances, an immune checkpoint inhibitor, for example, a PD-L1 axis binding antagonist, may be administered in conjunction with urelumab (also known as BMS-663513). In some instances, an immune checkpoint inhibitor, for example, a PD-L1 axis binding antagonist, may be administered in conjunction with an agonist directed against CD40, e.g., an activating antibody. In some instances, an immune checkpoint inhibitor, for example, a PD-L1 axis binding antagonist, may be administered in conjunction with CP-870893. In some instances, an immune checkpoint inhibitor, for example, a PD-L1 axis binding antagonist, may be administered in conjunction with an agonist directed against OX40 (also known as CD134), e.g., an activating antibody. In some instances, an immune checkpoint inhibitor, for example, a PD-L1 axis binding antagonist, may be administered in conjunction with an anti-OX40 antibody (e.g., AgonOX). In some instances, an immune checkpoint inhibitor, for example, a PD-L1 axis binding antagonist, may be administered in conjunction with an agonist directed against CD27, e.g., an activating antibody. In some instances, an immune checkpoint inhibitor, for example, a PD-L1 axis binding antagonist, may be administered in conjunction with CDX-1127. In some instances, an immune checkpoint inhibitor, for example, a PD-L1 axis binding antagonist, may be administered in conjunction with an antagonist directed against indoleamine-2,3-dioxygenase (IDO). In some instances, with the IDO antagonist is 1-methyl-D-tryptophan (also known as 1-D-MT).

In some instances, an immune checkpoint inhibitor, for example, a PD-L1 axis binding antagonist, may be administered in conjunction with an antibody-drug conjugate. In some instances, the antibody-drug conjugate comprises mertansine or monomethyl auristatin E (MMAE). In some instances, an immune checkpoint inhibitor, for example, a PD-L1 axis binding antagonist, may be administered in conjunction with an anti-NaPi2b antibody-MMAE conjugate (also known as DNIB0600A or RG7599). In some instances, an immune checkpoint inhibitor, for example, a PD-L1 axis binding antagonist, may be administered in conjunction with trastuzumab emtansine (also known as T-DM1, ado-trastuzumab emtansine, or KADCYLA®, Genentech). In some instances, an immune checkpoint inhibitor, for example, a PD-L1 axis binding antagonist, may be administered in conjunction with DMUC5754A. In some instances, an immune checkpoint inhibitor, for example, a PD-L1 axis binding antagonist, may be administered in conjunction with an antibody-drug conjugate targeting the endothelin B receptor (EDNBR), e.g., an antibody directed against EDNBR conjugated with MMAE.

In some instances, an immune checkpoint inhibitor, for example, a PD-L1 axis binding antagonist, may be administered in conjunction with an anti-angiogenesis agent. In some instances, an immune checkpoint inhibitor, for example, a PD-L1 axis binding antagonist, may be administered in conjunction with an antibody directed against a VEGF, e.g., VEGF-A. In some instances, an immune checkpoint inhibitor, for example, a PD-L1 axis binding antagonist, may be administered in conjunction with bevacizumab (also known as AVASTIN®, Genentech). In some instances, an immune checkpoint inhibitor, for example, a PD-L1 axis binding antagonist, may be administered in conjunction with an antibody directed against angiopoietin 2 (also known as Ang2). In some instances, an immune checkpoint inhibitor, for example, a PD-L1 axis binding antagonist, may be administered in conjunction with MEDI3617.

In some instances, an immune checkpoint inhibitor, for example, a PD-L1 axis binding antagonist, may be administered in conjunction with an antineoplastic agent. In some instances, an immune checkpoint inhibitor, for example, a PD-L1 axis binding antagonist, may be administered in conjunction with an agent targeting CSF-1R (also known as M-CSFR or CD115). In some instances, an immune checkpoint inhibitor, for example, a PD-L1 axis binding antagonist, may be administered in conjunction with anti-CSF-1R (also known as IMC-CS4). In some instances, an immune checkpoint inhibitor, for example, a PD-L1 axis binding antagonist, may be administered in conjunction with an interferon, for example interferon alpha or interferon gamma. In some instances, an immune checkpoint inhibitor, for example, a PD-L1 axis binding antagonist, may be administered in conjunction with Roferon-A (also known as recombinant Interferon alpha-2a). In some instances, an immune checkpoint inhibitor, for example, a PD-L1 axis binding antagonist, may be administered in conjunction with GM-CSF (also known as recombinant human granulocyte macrophage colony stimulating factor, rhu GM-CSF, sargramostim, or LEUKINE®). In some instances, an immune checkpoint inhibitor, for example, a PD-L1 axis binding antagonist, may be administered in conjunction with IL-2 (also known as aldesleukin or PROLEUKIN®). In some instances, an immune checkpoint inhibitor, for example, a PD-L1 axis binding antagonist, may be administered in conjunction with IL-12. In some instances, an immune checkpoint inhibitor, for example, a PD-L1 axis binding antagonist, may be administered in conjunction with an antibody targeting CD20. In some instances, the antibody targeting CD20 is obinutuzumab (also known as GA101 or GAZYVA®) or rituximab. In some instances, an immune checkpoint inhibitor, for example, a PD-L1 axis binding antagonist, may be administered in conjunction with an antibody targeting GITR. In some instances, the antibody targeting GITR is TRX518.

In some instances, an immune checkpoint inhibitor, for example, a PD-L1 axis binding antagonist, may be administered in conjunction with a cancer vaccine. In some instances, the cancer vaccine is a peptide cancer vaccine, which in some instances is a personalized peptide vaccine. In some instances the peptide cancer vaccine is a multivalent long peptide, a multi-peptide, a peptide cocktail, a hybrid peptide, or a peptide-pulsed dendritic cell vaccine (see, e.g., Yamada et al., *Cancer Sci.* 104:14-21, 2013). In some instances, an immune checkpoint inhibitor, for example, a PD-L1 axis binding antagonist, may be administered in conjunction with an adjuvant. In some instances, an immune checkpoint inhibitor, for example, a PD-L1 axis binding antagonist, may be administered in conjunction with a treatment comprising a TLR agonist, e.g., Poly-ICLC (also known as HILTONOL®), LPS, MPL, or CpG ODN. In some instances, an immune checkpoint inhibitor, for example, a PD-L1 axis binding antagonist, may be administered in conjunction with tumor necrosis factor (TNF) alpha. In some instances, an immune checkpoint inhibitor, for example, a PD-L1 axis binding antagonist, may be administered in conjunction with IL-1. In some instances, an immune checkpoint inhibitor, for example, a PD-L1 axis binding antagonist, may be administered in conjunction with HMGB1. In some instances, an immune checkpoint inhibitor, for example, a PD-L1 axis binding antagonist, may be administered in conjunction with an IL-10 antagonist. In some instances, an immune checkpoint inhibitor, for example, a PD-L1 axis binding antagonist, may be administered in conjunction with an IL-4 antagonist. In some instances, an immune checkpoint inhibitor, for example, a PD-L1 axis binding antagonist, may be administered in conjunction with an IL-13 antagonist. In some instances, an immune checkpoint inhibitor, for example, a PD-L1 axis binding antagonist, may be administered in conjunction with an HVEM antagonist. In some instances, an immune checkpoint inhibitor, for example, a PD-L1 axis binding antagonist, may be administered in conjunction with an ICOS agonist, e.g., by administration of ICOS-L, or an agonistic antibody directed against ICOS. In some instances, an immune checkpoint inhibitor, for example, a PD-L1 axis binding antagonist, may be administered in conjunction with a treatment targeting CX3CL1. In some instances, an immune checkpoint inhibitor, for example, a PD-L1 axis binding antagonist, may be administered in conjunction with a treatment targeting CXCL9. In some instances, an immune checkpoint inhibitor, for example, a PD-L1 axis binding antagonist, may be administered in conjunction with a treatment targeting CXCL10. In some instances, an immune checkpoint inhibitor, for example, a PD-L1 axis binding antagonist, may be administered in conjunction with a treatment targeting CCL5. In some instances, an immune checkpoint inhibitor, for example, a PD-L1 axis binding antagonist, may be administered in conjunction with an LFA-1 or ICAM1 agonist. In some instances, an immune checkpoint inhibitor, for example, a PD-L1 axis binding antagonist, may be administered in conjunction with a Selectin agonist.

In some instances, an immune checkpoint inhibitor, for example, a PD-L1 axis binding antagonist, may be administered in conjunction with a targeted therapy. In some instances, an immune checkpoint inhibitor, for example, a PD-L1 axis binding antagonist, may be administered in conjunction with an inhibitor of B-Raf. In some instances, an immune checkpoint inhibitor, for example, a PD-L1 axis binding antagonist, may be administered in conjunction with vemurafenib (also known as ZELBORAF®). In some instances, an immune checkpoint inhibitor, for example, a PD-L1 axis binding antagonist, may be administered in conjunction with dabrafenib (also known as TAFINLAR®). In some instances, an immune checkpoint inhibitor, for example, a PD-L1 axis binding antagonist, may be administered in conjunction with erlotinib (also known as TARCEVA®). In some instances, an immune checkpoint inhibitor, for example, a PD-L1 axis binding antagonist, may be administered in conjunction with an inhibitor of a MEK, such as MEK1 (also known as MAP2K1) or MEK2 (also known as MAP2K2). In some instances, an immune checkpoint inhibitor, for example, a PD-L1 axis binding antagonist, may be administered in conjunction with cobimetinib (also known as GDC-0973 or XL-518). In some instances, an immune checkpoint inhibitor, for example, a PD-L1 axis binding antagonist, may be administered in conjunction with trametinib (also known as MEKINIST®). In some instances, an immune checkpoint inhibitor, for example, a PD-L1 axis binding antagonist, may be administered in conjunction with an inhibitor of K-Ras. In some instances, an immune checkpoint inhibitor, for example, a PD-L1 axis binding antagonist, may be administered in conjunction with an inhibitor of c-Met. In some instances, an immune checkpoint inhibitor, for example, a PD-L1 axis binding antagonist, may be administered in conjunction with onartuzumab (also known as MetMAb). In some instances, an immune checkpoint inhibitor, for example, a PD-L1 axis binding antagonist, may be administered in conjunction with an inhibitor of Alk. In some instances, an immune checkpoint inhibitor, for example, a PD-L1 axis binding antagonist, may be administered in conjunction with AF802 (also known as CH5424802 or alectinib). In some instances, an immune checkpoint inhibitor, for example, a PD-L1 axis binding antagonist, may be administered in conjunction with an inhibitor of a phosphatidylinositol 3-kinase (PI3K). In some instances, an immune checkpoint inhibitor, for example, a PD-L1 axis binding antagonist, may be administered in conjunction with BKM120. In some instances, an immune checkpoint inhibitor, for example, a PD-L1 axis binding antagonist, may be administered in conjunction with idelalisib (also known as GS-1101 or CAL-101). In some instances, an immune checkpoint inhibitor, for example, a PD-L1 axis binding antagonist, may be administered in conjunction with perifosine (also known as KRX-0401). In some instances, an immune checkpoint inhibitor, for example, a PD-L1 axis binding antagonist, may be administered in conjunction with an inhibitor of an Akt. In some instances, an immune checkpoint inhibitor, for example, a PD-L1 axis binding antagonist, may be administered in conjunction with MK2206. In some instances, an immune checkpoint inhibitor, for example, a PD-L1 axis binding antagonist, may be administered in conjunction with GSK690693. In some instances, an immune checkpoint inhibitor, for example, a PD-L1 axis binding antagonist, may be administered in conjunction with GDC-0941. In some instances, an immune checkpoint inhibitor, for example, a PD-L1 axis binding antagonist, may be administered in conjunction with an inhibitor of mTOR. In some instances, an immune checkpoint inhibitor, for example, a PD-L1 axis binding antagonist, may be administered in conjunction with sirolimus (also known as rapamycin). In some instances, an immune checkpoint inhibitor, for example, a PD-L1 axis binding antagonist, may be administered in conjunction with temsirolimus (also known as CCI-779 or TORISEL®). In some instances, an immune checkpoint inhibitor, for example, a PD-L1 axis binding antagonist, may be administered in conjunction with everolimus (also known as RAD001). In some instances, an immune checkpoint inhibitor, for example, a PD-L1 axis binding antagonist, may be administered in conjunction with ridaforolimus (also known as AP-23573, MK-8669, or deforolimus). In some instances, an immune checkpoint inhibitor, for example, a PD-L1 axis binding antagonist, may be administered in conjunction with OSI-027. In some instances, an immune checkpoint inhibitor, for example, a PD-L1 axis binding antagonist, may be administered in conjunction with AZD8055. In some instances, an immune checkpoint inhibitor, for example, a PD-L1 axis binding antagonist, may be administered in conjunction with INK128. In some instances, an immune checkpoint inhibitor, for example, a PD-L1 axis binding antagonist, may be administered in conjunction with a dual PI3K/mTOR inhibitor. In some instances, an immune checkpoint inhibitor, for example, a PD-L1 axis binding antagonist, may be administered in conjunction with XL765. In some instances, an immune checkpoint inhibitor, for example, a PD-L1 axis binding antagonist, may be administered in conjunction with GDC-0980. In some instances, an immune checkpoint inhibitor, for example, a PD-L1 axis binding antagonist, may be administered in conjunction with BEZ235 (also known as NVP-BEZ235). In some instances, an immune checkpoint inhibitor, for example, a PD-L1 axis binding antagonist, may be administered in conjunction with BGT226. In some instances, an immune checkpoint inhibitor, for example, a PD-L1 axis binding antagonist, may be administered in conjunction with GSK2126458. In some instances, an immune checkpoint inhibitor, for example, a PD-L1 axis binding antagonist, may be administered in conjunction with PF-04691502. In some instances, an immune checkpoint inhibitor, for example, a PD-L1 axis binding antagonist, may be administered in conjunction with PF-05212384 (also known as PKI-587).

IV. Articles of Manufacture and Kits

In another aspect of the invention, an article of manufacture or kit containing materials useful for the prognostic assessment and/or treatment of individuals is provided.

In some instances, such articles of manufacture or kits can be used to identify an individual having a cancer (e.g., lung cancer (e.g., NSCLC), bladder cancer (e.g., UC), kidney cancer (e.g., RCC), or breast cancer (e.g., TNBC)) who may benefit from treatment with an immune checkpoint inhibitor, e.g., an immune checkpoint inhibitor described in Section IIIB herein, e.g., a PD-L1 axis binding antagonist. Such articles of manufacture or kits may include (a) reagents for determining the polygenic risk score (PRS) of an individual for at least one, at least two, or all three of the group consisting of vitiligo, psoriasis, and atopic dermatitis or for determining the presence or absence of one or more tumor-associated factors in an individual, as described in Section IIA and (b) instructions for using the reagents to identify an individual having a cancer (e.g., lung cancer (e.g., NSCLC), bladder cancer (e.g., UC), kidney cancer (e.g., RCC), or breast cancer (e.g., TNBC)) who may benefit from a treatment comprising an immune checkpoint inhibitor, e.g., an immune checkpoint inhibitor described in Section IIIB herein, e.g., a PD-L1 axis binding antagonist.

For example, in some aspects, the article of manufacture or kit includes (a) reagents for determining the polygenic risk score (PRS) of an individual for at least one, at least two, or all three of the group consisting of vitiligo, psoriasis, and atopic dermatitis or for determining the presence or absence of one or more tumor-associated factors in an individual, as described in Section IIA herein and (b) instructions for using the reagents to identify an individual having a cancer (e.g., lung cancer (e.g., NSCLC), bladder cancer (e.g., UC), kidney cancer (e.g., RCC), or breast cancer (e.g., TNBC)) who may benefit from a treatment comprising an immune checkpoint inhibitor, e.g., an immune checkpoint inhibitor described in Section IIIB herein, e.g., a PD-L1 axis binding antagonist.

In some aspects, such articles of manufacture or kits include an immune checkpoint inhibitor, e.g., an immune checkpoint inhibitor described in Section IIIB herein, for treating an individual with a cancer (e.g., lung cancer (e.g., NSCLC), bladder cancer (e.g., UC), kidney cancer (e.g., RCC), or breast cancer (e.g., TNBC)). In some aspects, the article of manufacture or kit includes (a) an immune checkpoint inhibitor, e.g., an immune checkpoint inhibitor described in Section IIIB herein and (b) a package insert including instructions for administration of the immune checkpoint inhibitor to an individual having a cancer (e.g., lung cancer (e.g., NSCLC), bladder cancer (e.g., UC), kidney cancer (e.g., RCC), or breast cancer (e.g., TNBC)), wherein, prior to treatment, the polygenic risk score (PRS) of an individual for at least one, at least two, or all three of the group consisting of vitiligo, psoriasis, and atopic dermatitis in a sample from the individual has been determined and one or both of the PRS for vitiligo and the PRS for psoriasis are the same as above a reference PRS and/or the PRS for atopic dermatitis is below a reference PRS, or the expression level of at least one, at least two, at least three, at least four, at least five, at least six, at least seven, at least eight, at least nine, at least ten, at least eleven, or all twelve genes selected from the group consisting of IL23A, IL12A, CCL20, CD8A, CXCL2, CXCL9, CXCL10, GZMA, GZMB, INFG, PRF1, or TBX21 or combinations thereof in a sample from the individual has been determined and the expression level of at least one, at least two, at least three, at least four, at least five, at least six, at least seven, at least eight, at least nine, at least ten, or all eleven of IL23A, CCL20, CD8A, CXCL2, CXCL9, CXCL10, GZMA, GZMB, INFG, PRF1, or TBX21 in the sample is above a threshold expression level and/or the expression level of IL12A is below a threshold expression level.

Any of the articles of manufacture or kits described may include a carrier means being compartmentalized to receive in close confinement one or more container means such as vials, tubes, and the like, each of the container means comprising one of the separate elements to be used in the method. Where the article of manufacture or kit utilizes nucleic acid hybridization to detect the target nucleic acid, the kit may also have containers containing nucleotide(s) for amplification of the target nucleic acid sequence and/or a container comprising a reporter-means, such as an enzymatic, fluorescent, or radioisotope label.

In some aspects, the article of manufacture or kit includes the container described above and one or more other containers including materials desirable from a commercial and user standpoint, including buffers, diluents, filters, needles, syringes, and package inserts with instructions for use. A label may be present on the container to indicate that the composition is used for a specific application, and may also indicate directions for either in vivo or in vitro use, such as those described above. For example, the article of manufacture or kit may further include a container including a pharmaceutically-acceptable buffer, such as bacteriostatic water for injection (BWFI), phosphate-buffered saline, Ringer's solution, and dextrose solution.

The articles of manufacture or kits described herein may have a number of aspects. In one aspect, the article of manufacture or kit includes a container, a label on said container, and a composition contained within said container, wherein the composition includes one or more polynucleotides that hybridize to a complement of a locus described herein under stringent conditions, and the label on said container indicates that the composition can be used to evaluate the presence of a gene listed herein (e.g., IL23A, IL12A, CCL20, CD8A, CXCL2, CXCL9, CXCL10, GZMA, GZMB, INFG, PRF1, or TBX21) in a sample, or of a single-nucleotide polymorphism (SNP) described herein in a sample, and wherein the kit includes instructions for using the polynucleotide(s) for evaluating the presence of the gene RNA or DNA or the presence of the SNP in a particular sample type.

For oligonucleotide-based articles of manufacture or kits, the article of manufacture or kit can include, for example: (1) an oligonucleotide, e.g., a detectably labeled oligonucleotide, which hybridizes to a nucleic acid sequence encoding a protein or (2) a pair of primers useful for amplifying a nucleic acid molecule. The article of manufacture or kit can also include, e.g., a buffering agent, a preservative, or a protein stabilizing agent. The article of manufacture or kit can further include components necessary for detecting the detectable label (e.g., an enzyme or a substrate). The article of manufacture or kit can further include components necessary for analyzing the sequence of a sample (e.g., a restriction enzyme or a buffer). The article of manufacture or kit can also contain a control sample or a series of control samples that can be assayed and compared to the test sample. Each component of the article of manufacture or kit can be enclosed within an individual container and all of the various containers can be within a single package, along with instructions for interpreting the results of the assays performed using the kit.

V. EXAMPLES

The following are examples of methods and compositions of the invention. It is understood that various other aspects may be practiced, given the general description provided above, and the examples are not intended to limit the scope of the claims.

Example 1. Low Grade Dermatological irAEs are Associated with Longer Overall Survival in mUC To examine the relationship between safety and efficacy of checkpoint blockade, we conducted an analysis of irAEs using data from safety evaluable patients receiving atezolizumab (anti-PD-L1) from IMvigor211 (N=459) and IMvigor210 (N=429) in metastatic urothelial carcinoma (mUC) patients (Balar et al., Lancet, 389:67-76, 2017; Rosenberg et al., Lancet, 387:1909-1920, 2016; Powles et al., Lancet, 391:748-757, 2018). In both trials, irAEs were monitored and graded using a consistent Adverse Events of Special Interest (AESI) strategy (Brahmer et al., *J. Clin. Oncol.*, 36:1714-1768, 2018). The committees that approved study protocols and confirmation of informed consent from all study participants are included in the previous publications.

A. Definition of irAE Categories

Immune related adverse event (irAE) data conformed to an internal Adverse of Events of Special Interest (AESI) strategy. The strategy identified a collection of adverse event terms that had a putative immune-related etiology. AESIs were grouped into the organ and system categories dermatological (skin), gastrointestinal (GI), and endocrine to allow meaningful statistical associations with survival. The dermatological category consisted of the AESIs "Immune-Related Rash" and "Immune-Related Severe Cutaneous Reaction." The GI category consisted of the AESIs "Immune-Related Hepatitis," "Immune-Related Colitis," and "Immune-Related Pancreatitis." The endocrine category consisted of the AESIs "Immune-Related Hypothyroidism," "Immune-Related Hyperthyroidism," "Immune-Related Adrenal Insufficiency,", "Immune-Related Diabetes Mellitus," and "Immune-Related Hypophysitis." All other system and organ-based categories (e.g., renal, neuro-muscular, pulmonary, and systemic) occurred at rates <5% and were not considered for association due to limited statistical power. Grading for AESIs was defined according to the National Cancer Institute Common Terminology Criteria for Adverse Events (NIH CTCAE) as delineated in the original study protocols.

As previously reported, high grade events were less common than low grade events (FIG. 1A). Grade 1 and 2 skin irAEs were the most common (up to 17.5% of patients), followed by GI and endocrine irAEs.

B. Time-Dependent irAE Associations

A time-dependent covariate in a Cox proportional hazards model that incorporated the time to irAE was used in the assessment of association of between survival and irAEs. Analyses controlled for the following covariates, which were measured at baseline prior to treatment: presence or absence of liver metastases; high or low C-reactive protein (CRP) (where >10 mg/mL is high); neutrophil to lymphocyte ratio normalized to the quantiles of the standard normal distribution; high or low alkaline phosphatase in serum at baseline (>147 IU/L was designated as high); high or low albumin in serum at baseline (<35 g/L is low); high or low lactate dehydrogenase (LDH) in serum at baseline (>400 g/L is high); gender; baseline Eastern Cooperative Oncology Group (ECOG) status (0 or 1); and immune cell (IC) staining of PD-L1 by immunohistochemistry (IHC). IHC data was obtained as using methods previously described in the original study publication and protocols (Balar et al., *Lancet*, 389:67-76, 2017; Rosenberg et al., *Lancet*, 387:1909-1920, 2016; Powles et al., *Lancet*, 391:748-757, 2018). Time dependent covariate was constructed using the tMerge function in the R survival package.

Overall survival was associated with low-grade skin irAEs in IMvigor211 (p=0.024; hazard ratio (HR) 0.66; 95% CI 0.45-0.95) and IMvigor210 (p=0.0023; HR 0.53; 95% CI 0.35-0.80; FIG. 1B). To verify the robustness of our results, we conducted a landmark analysis. We selected landmarks at the point at which 90% of patients in the low grade skin irAE group had experienced their event (FIG. 1C) and confirmed an association with improved OS in both IMvigor211 and IMvigor210 (FIG. 1D).

Example 2. Collection of Genotype Data

A. Sample Collection

Figure 5:
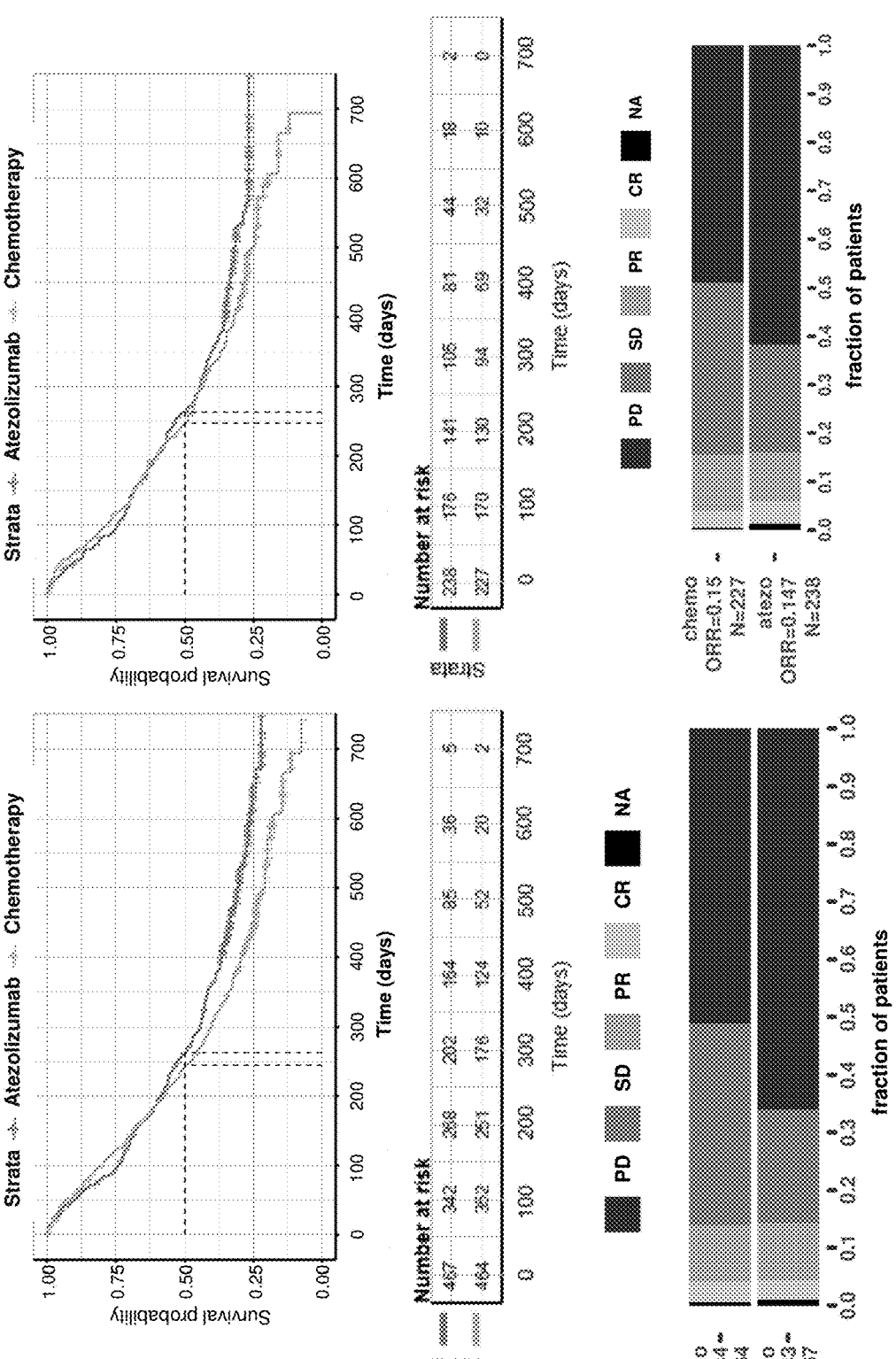
FIG. 5 is a set of graphs showing a comparison of outcomes in the intent-to-treat (ITT) population and the biomarker available population. The left column shows Kaplan-Meier plots for OS and the distribution of Best Confirmed Objective Response (BCOR) in the ITT population of N=931 individuals. CR, PR, SD, and PD designate complete response, partial response, stable disease, and progressive disease, respectively. Corresponding arm-specific objective response rates (ORRs) are shown to the left of the stacked proportional bar plots. The right column shows Kaplan-Meier plots for OS and BCOR rates for the biomarker available (germline whole genome sequencing data) population of N=465 individuals.
Figure 6:
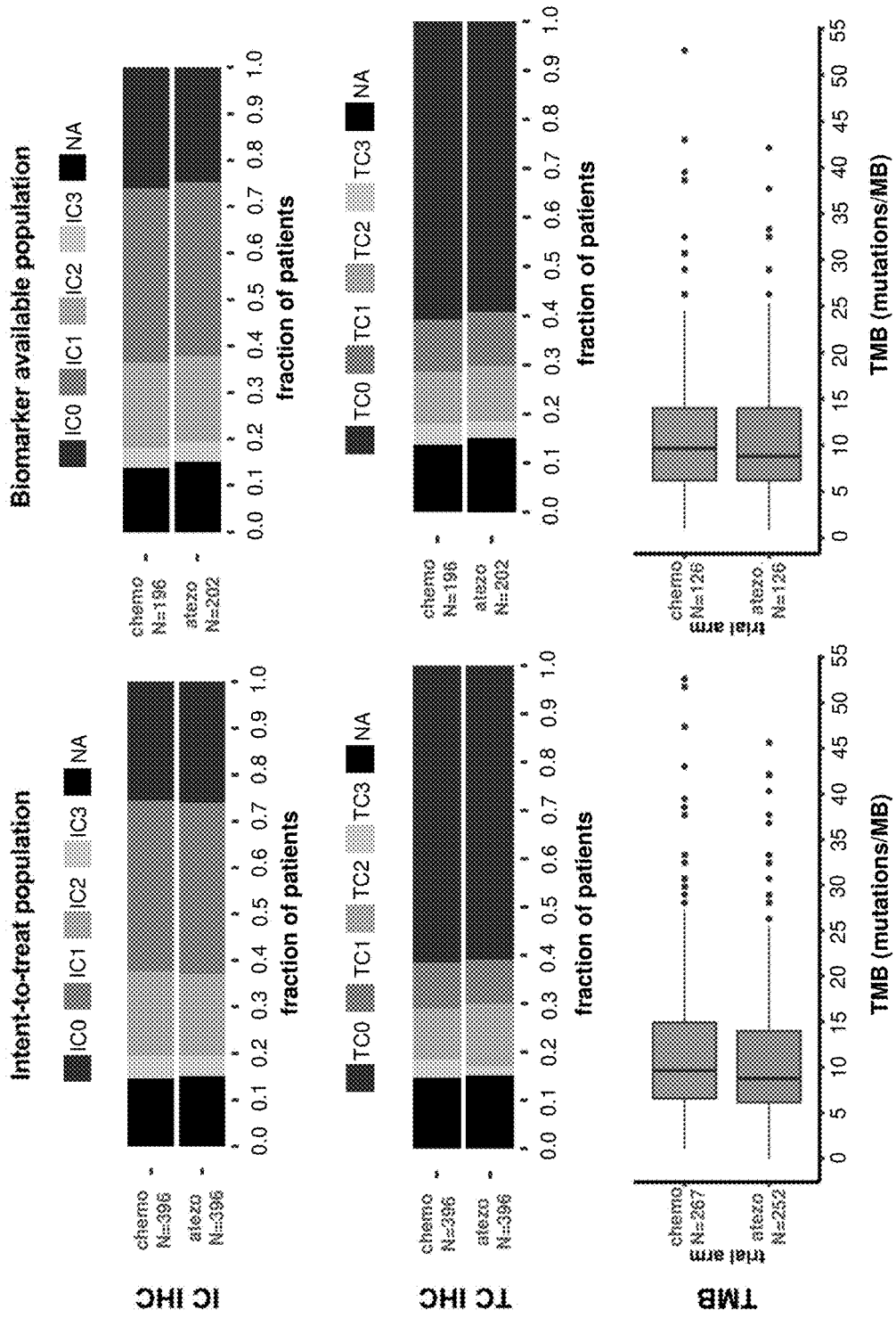
FIG. 6 is a set of graphs showing a comparison of tumor-associated factors in the ITT population and the biomarker available population. N designates the number of individuals for which the tumor-associated factor was measured in the ITT and the biomarker available populations. NA designates the proportion of individuals for which the tumor-associated factor was not measured. TC0 and IC0 designate tumor samples with no evidence of immune and tumor cell staining of PD-L1 by IHC, respectively. TC1-TC3 and IC1-IC3 designate increasing levels of tumor and immune cell PD-L1 staining. TMB=tumor mutational burden.

Blood samples from N=479 individuals ("biomarker available population") from IMvigor211 (Powles et al., *Lancet*, 391:748-757, 2018) were collected on the basis of availability and signed consent for research on germline DNA. 465 individuals (238 receiving atezolizumab and 228 chemotherapy treated) met strict filters for population and genotype data quality control. We confirmed that OS and best confirmed objective response (BCOR) were no different in the biomarker available population than in the intent-to-treat population of 931 individuals (FIG. 5). We also confirmed that immune (IC) and tumor cell (TC) staining of PD-L1 by IHC and tumor mutation burden (TMB) were similarly balanced across trial arms in the biomarker available population (FIG. 6).

B. Whole Genome Sequencing

Genomic DNA was extracted from blood samples using the DNA Blood400 kit (Chemagic) and eluted in 50 μL Elution Buffer (EB, Qiagen). DNA was sheared (Covaris LE220) and sequencing libraries were prepared using the TruSeq Nano DNA HT kit (Illumina, Inc.). Libraries were sequenced at Human Longevity (San Diego, CA, USA). Whole-genome sequencing (WGS) data was generated to an average read depth of 30× using the HiSeq platform (Illumina X10, San Diego, CA, USA) and processed using the Burrows Wheeler Aligner (BWA)/Genome Analysis Toolkit (GATK) best practices pipeline (Van der Auwera et al., *Curr Protoc Bioinformatics*, 11:11.10.1-11.10.33, 2013; McKenna et al., *Genome Res.*, 20, 1297-1303, 2010; DePristo et al., *Nat. Genet.*, 43:491-498, 2011). Short reads were mapped to hg38/GRCh38 (GCA_000001405.15), including alternate assemblies, using an alt-aware version of BWA to generate BAM files (Li and Durbin, *Bioinformatics*, 25:1754-1760, 2009). All sequencing data were checked for concordance with SNP fingerprint data collected before sequencing.

C. Genotype Data and Population Quality Control

Only variants that passed the Genome Analysis Toolkit (GATK) threshold for overall quality were used. Genotypes with the GATK-assigned quality (GQ)≤20 were set to missing followed by removal of variants with an across-sample missing genotype rate of 0.1 or more. Samples were also checked for a high rate of missing variant calls and extreme values of homozygosity as measured by inbreeding coefficient (F) estimates. No samples were removed by these filters. Pairwise identity-by-descent (IBD) analysis (patient relatedness) was also conducted; no pair of samples were detected that had proportion IBD (PI_HAT>0.1) that also had P(IBD=0)/Z0 of greater than 0.4 or more. Another assay tested whether any one of the samples had a proportion IBD (PI_HAT>0.1) with a large number (>200) of other samples indicating possible cross-contamination. No samples were filtered at this step. Ancestry of the samples was estimated using ADMIXTURE in supervised mode using the five major ancestry groups from the 1000 Genomes project as reference populations (Auton et al., *Nature*, 526:68-74, 2015; Alexander et al., *Genome Res.*, 19:1655-1664, 2009). Individuals with European ancestry coefficient of 0.7 or less were removed. Using the remaining samples, principal component analysis (PCA) using EIGENSTRAT (Price et al., *Nat. Genet.*, 38:904-909, 2006) was performed. Five rounds of PCA outlier removal iterations were performed at the default settings of EIGENSTRAT. Then, the final PCA was then performed to compute eigenvectors, the top 5 of which were used in association analysis to correct for sample ancestry. These last two population filters removed a total of 14 samples.

D. Inference of HLA Alleles from Whole-Genome Sequencing Data

HLA*PRG: LA (retrieved Mar. 8, 2017, git commit SHA-1 hash prefixed by 7b9ba45) was used to infer human leukocyte antigen (HLA) alleles at G group resolution from WGS data, starting from BAM files generated as described above (Dilthey et al., *PLoS Comput. Biol.,* 12: e1005151).

Example 3. Construction of Polygenic Risk Scores

To test the hypothesis that genetic risk for skin autoimmunity was associated with dermatological irAEs experienced with atezolizumab treatment, we used publicly available genome wide association study (GWAS) summary statistics to construct polygenic risk scores (PRSs) for the dermatological autoimmune diseases psoriasis (PSO), atopic dermatitis (AD), and vitiligo (VIT) (FIG. 2A, Table 1, FIG. 7) (Dudbridge, *PLoS Genet.,* 9: e1003348, 2013; Torkamani et al., *Nat Rev. Genet.,* 19, 581-590, 2018; Chatterjee et al., *Nat. Rev. Genet.,* 17, 392-406, 2016). We additionally constructed PRSs for Alzheimer's disease (ALZ) to serve as negative controls.

The genotype data collected was in Genome Reference Consortium Human Build 38 (GRCh38) coordinates with corresponding reference SNP IDs (rsids) from dbSNP v150. For each of the summary statistics, any rsids that changed from old versions of dbSNP to dbSNP v150 were remapped. Variants that were called within our IMvigor211 WGS data were used. Only variants that had estimated odds ratios in the summary statistics were used. A few of the variants appeared as duplicates in the summary statistics, and in such instances, only the entry with the smallest p-value was kept. Variants with strand ambiguity (A/T or C/G genotypes) were removed. Variants that were not present in the EUR population in 1000 genomes were also filtered out. All non-autosomal SNPs were removed as well. The risk allele in the summary statistics was confirmed to match the alleles called at variants in our WGS data. Due to the strong linkage disequilibrium (LD) in the major histocompatibility complex (MHC) locus, risk scores did not include SNPs in this region; other difficult-to-genotype regions that have alternate assemblies in the reference genome were also excluded. LD clumping was performed using the EUR population in 1000 genomes as a LD reference panel to extract independent signals from the genome-wide association study (GWAS) summary statistics (Auton et al., *Nature,* 526:68-74, 2015). Specifically, a 250 kb window around the index SNP was employed, adding variants with $r^2>0.25$ to the current clump (corresponding to PLINK parameters --clump-p1 1 --clump-p2 1 --clump-r2 0.25 --clump-kb 250). The polygenic risk score (PRS) was computed as follows:

$$\hat{S} = \sum_{i=1}^{M} \beta_i \cdot G_i$$

where M is the number of SNPs at a given GWAS p-value cutoff and $\beta_i$ corresponds to the log odds ratio of the ith SNP and $G_i=\{0,1,2\}$ corresponding to the number of copies of the risk allele.

Figure 7:
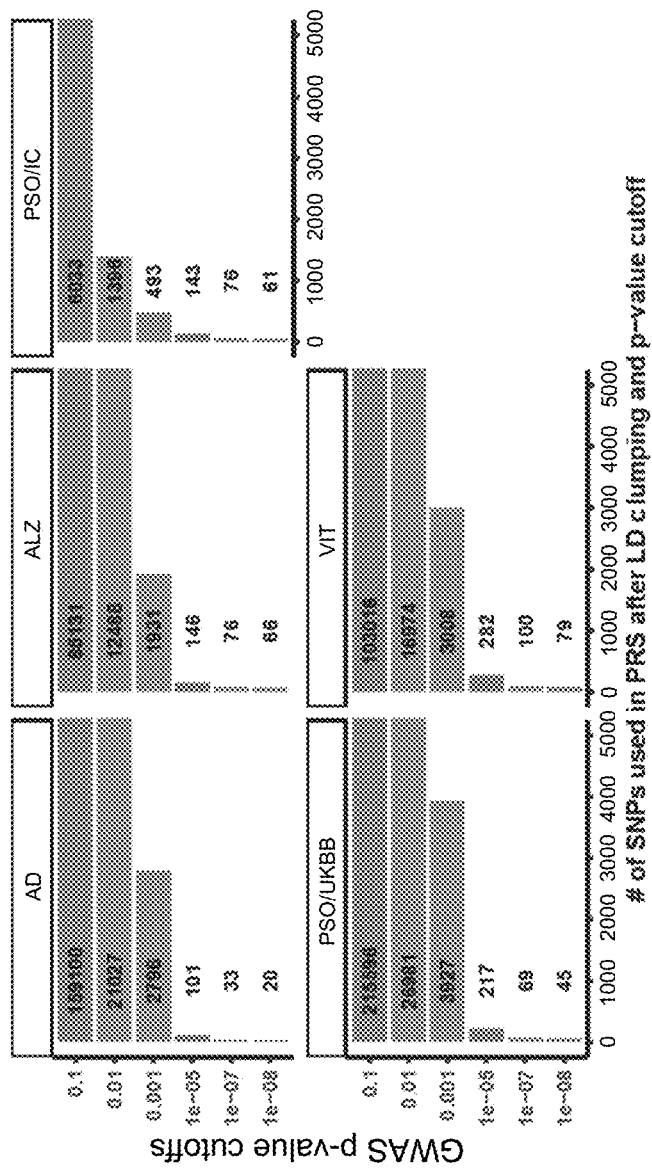
FIG. 7 is a set of graphs showing the number of SNPs considered to be risk alleles for a given disease at a given GWAS p-value cutoff. Bar plots were clipped at 5000 SNPs. GWAS p-value cutoff was applied after filtering and linkage disequilibrium (LD) clumping. The total number of SNPs used per PRS and GWAS p-value cutoff is overlaid on the bars.

PRSs can use SNPs that do not achieve genome-wide significant p-value values in the original GWAS. This is of relevance as the GWAS p-value cutoff at which the PRS is most predictive is often unknown (Dudbridge, *PLoS Genet.,* 9: e1003348, 2013; Euesden et al., *Bioinformatics,* 31:1466-1468, 2015). Following standard practice, PRSs were created using a pre-defined set of fixed GWAS p-value cutoffs ($1\times10^{-8}$, $1\times10^{-7}$, $1\times10^{-6}$, $1\times10^{-5}$, $1\times10^{-4}$, $1\times10^{-3}$, $1\times10^{-2}$, $1\times10^{-1}$), with each score distinguished by the number of SNPs used (FIG. 7). We then asked which of these PRSs were associated with occurrence of dermatological irAEs, accounting for multiple testing at a preselected false discovery rate. Because WGS data was used, a small number of SNPs were multi-allelic in the WGS dataset. All other alleles were ignored, and only the presence of the risk allele contributed to the PRS for the individual. PRSs were quantile normalized to the quantiles of a standard normal distribution to allow comparison across GWAS.

Example 4. PRSs for Skin Autoimmunity as Predictive Biomarkers for Checkpoint Blockade A. PRS Associations with Skin irAE Occurrence Associations between PRSs were tested for at a range of GWAS p-value cutoffs and occurrence of skin irAEs using logistic regression. False discovery rate (FDR) was estimated using the Benjamini-Hochberg (BH) procedure (Benjamini and Hochberg, Journal of the Royal Statistical Society. Series B (Methodological), 57:289, 1995). Our analysis controlled for 5 genotype eigenvectors/PCs and gender. Logistic regression was performed using glm( ) in R (v3.5.0).

Figure 2B:
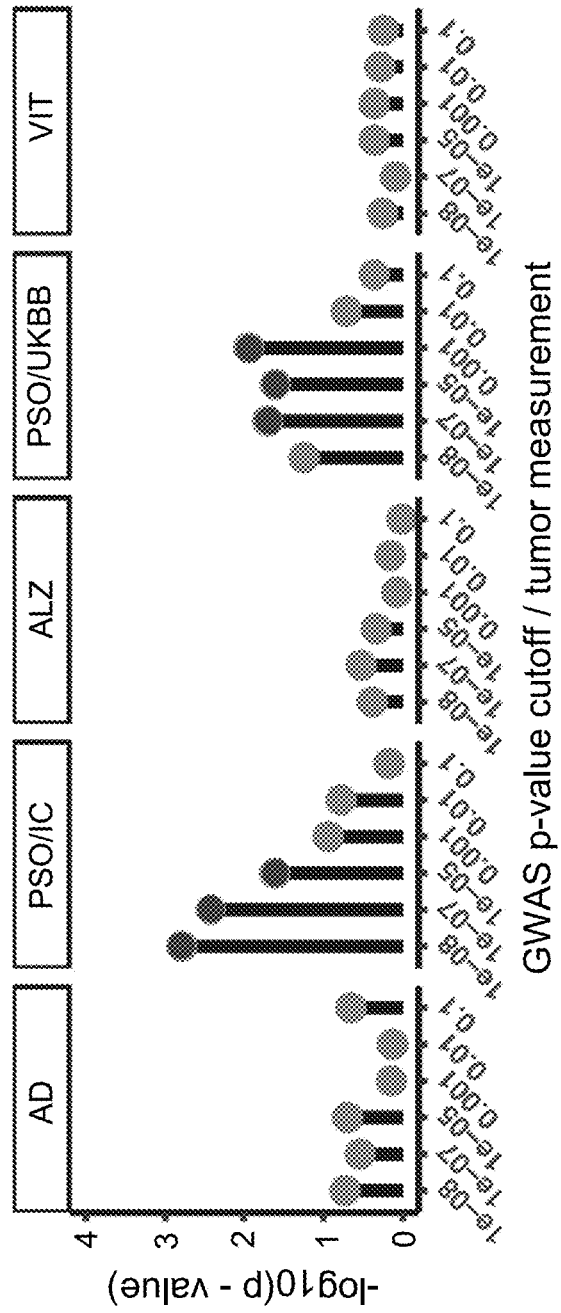
FIG. 2B is a graph showing negative $\log_{10}$ p-values for a given PRS testing for association with occurrence of skin irAEs. Tests controlled for five genotype principal components and gender by logistic regression. Light-colored circles show associations that were significant at false discovery rate (FDR) of 10%. Dark-colored circles did not meet statistical significance. AD=atopic dermatitis, PSO/IC=psoriasis (Immunochip data), ALZ=Alzheimer's (negative control), PSO/UKBB=psoriasis (UK Biobank data), VIT=vitiligo.
Figure 2C:
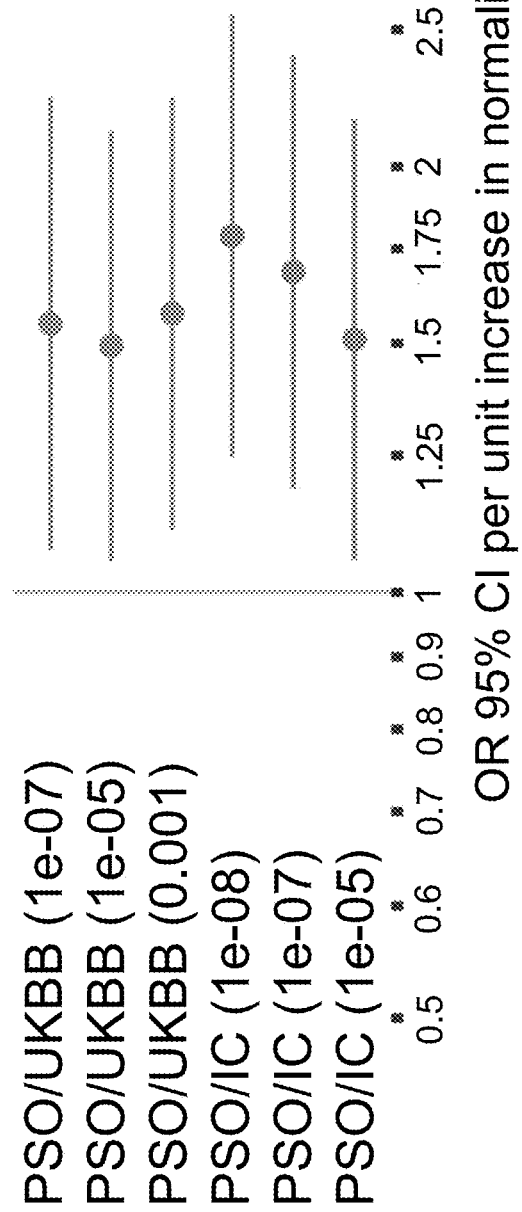
FIG. 2C is a graph showing odds ratios (ORs) and 95% confidence intervals (CIs) for PRSs and skin irAE occurrence for PRSs that met a significance cutoff of FDR 10%. ORs are expressed in per unit change of a normalized PRS.

We identified associations at a false discovery rate (FDR) of 10% between the occurrence of skin irAEs and genetic risk for psoriasis within the atezolizumab arm of IMvigor211 (FIG. 2B). The associations were consistent across GWASs used to construct the PRSs, derived using the Immunochip (PSO/IC) and the UK Biobank (PSO/UKBB) studies, where psoriasis cases were determined clinically or were self-reported, respectively (FIG. 2C).

B. PRS Associations with Survival and PRS by Trial Arm Interactions

Associations between PRSs and survival were tested for at a range of GWAS p-value cutoffs using a Cox proportional hazards model. p-values were computed using the Wald test on the coefficient associated with PRS. To identify trial arm by PRS interactions, p-values were computed using the Wald test on the coefficient associated with PRS by trial arm interaction term. The model for assessing trial arm interactions also contained the lower-order terms for PRS and arm. False discovery rate (FDR) was estimated using the Benjamini-Hochberg (BH) procedure (Benjamini and Hochberg, Journal of the Royal Statistical Society. Series B (Methodological), 57:289, 1995). Our analysis controlled for the following covariates, which were measured at baseline prior to treatment: presence or absence of liver metastases; high or low CRP where (>10 mg/ml is high); neutrophil to lymphocyte ratio normalized to the quantiles of the standard normal distribution; high or low alkaline phosphatase in serum at baseline (>147 IU/L was designated as high); high or low albumin in serum at baseline (<35 g/L is low); high or low LDH in serum at baseline (>400 g/L is high); gender; baseline ECOG status (0 or 1); 5 genotype PCs/eigenvectors.

The same approach was used for tumor-associated factors (tumor mutation burden (TMB), T-effector signature, immune cell (IC) IHC, and tumor cell (TC) IHC). For immune cell (IC) and tumor cell (TC) IHC of PD-L1 the integers 0, 1, 2, and 3 were used to capture the ordinal relationship between PD-L1 staining values. All survival analyses were conducted using the survival package in R.

Figure 2D:
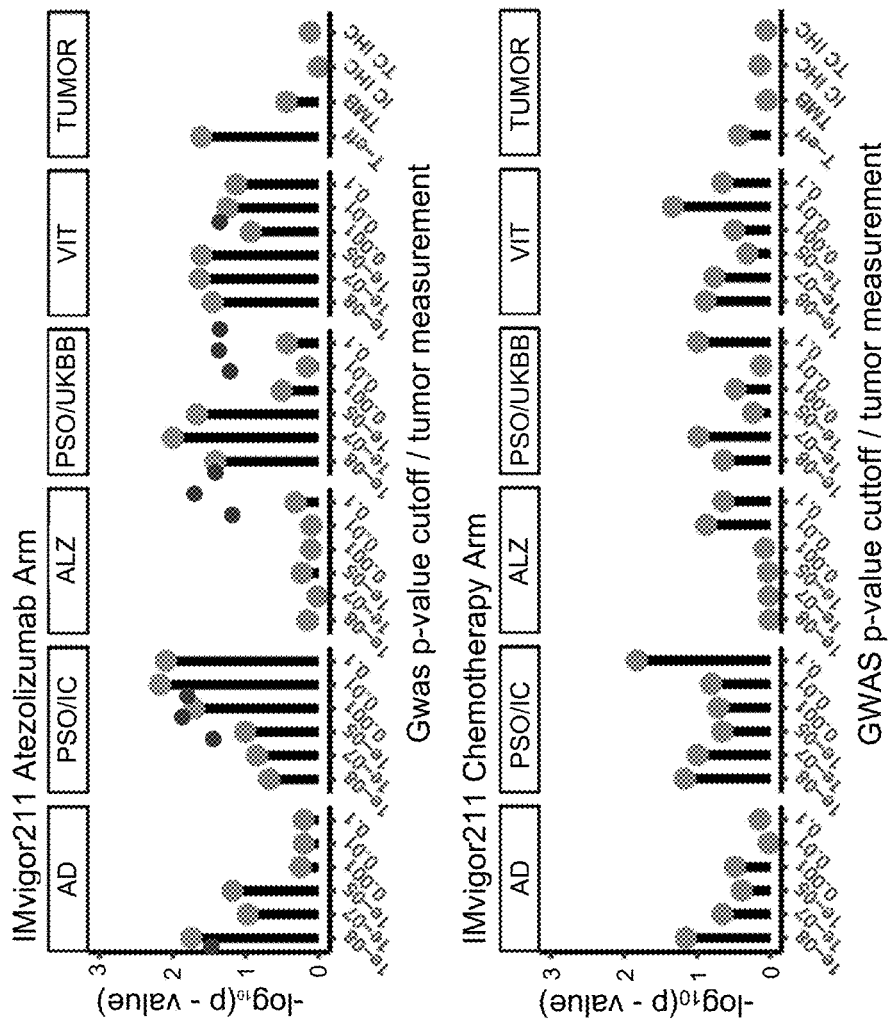
FIG. 2D is a set of graphs showing negative $\log_{10}$ p-values for a given GWAS and p-value cutoff PRS testing for association with OS using a Cox proportional hazards model. Tests controlled for five genotype principal components and baseline prognostic factors. Tumor=T-effector gene signature score of tumor.

We found that PRSs for atopic dermatitis, psoriasis, and vitiligo were associated with OS in the atezolizumab arm of IMvigor211 at an FDR of 10% (FIG. 2D). PRSs for Alzheimer's disease, as expected, did not show any association signal. The T-effector gene signature, a measure of $CD8^+$ T-cell effector function within a tumor, was the only tumor-associated factor significantly associated with OS within the atezolizumab arm.

Figure 2E:
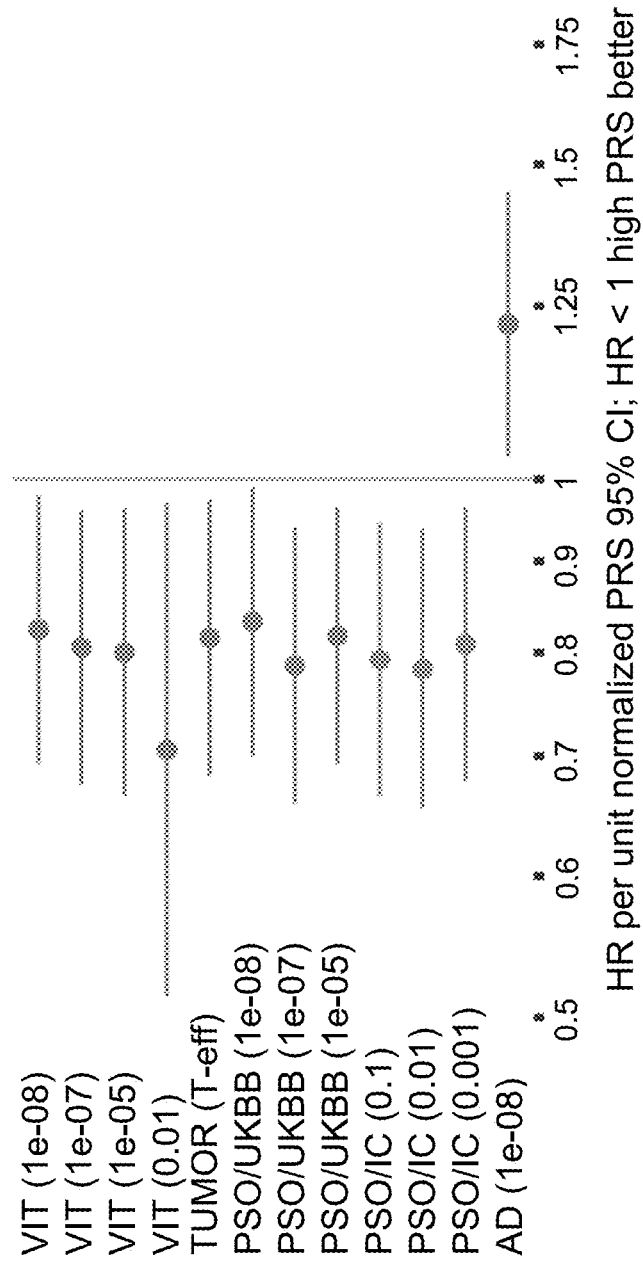
FIG. 2E is a graph showing HRs and 95% CIs for PRS and OS associations, using a significance cutoff of 10% FDR. HRs are expressed in unit change in of a normalized PRS. TMB=tumor mutation burden; IC IHC=PD-L1 expression on immune cells; TC IHC=PD-L1 expression on tumor cells.
Figure 8:
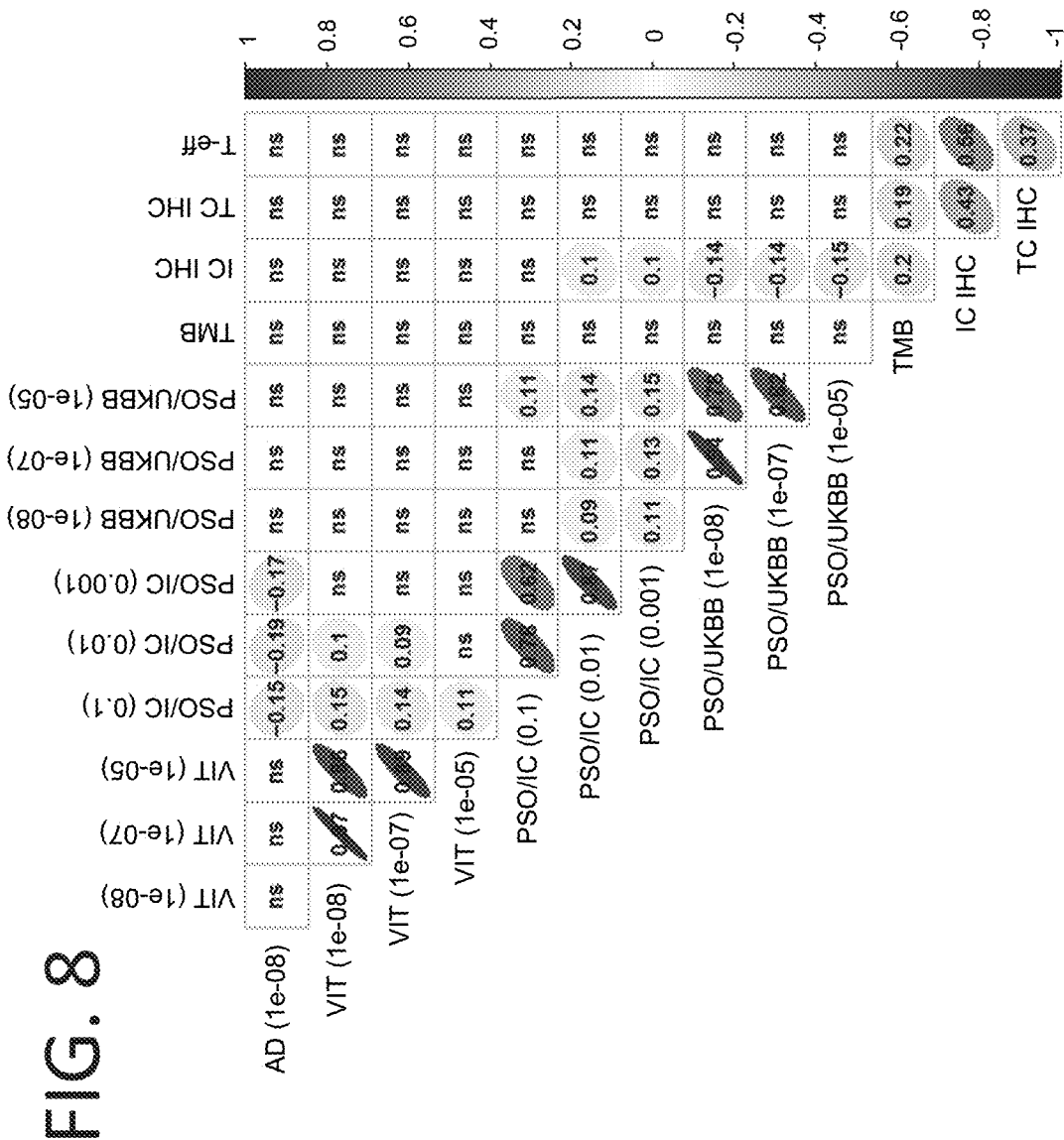
FIG. 8 is a chart showing Spearman's rank correlation between PRSs and tumor-associated factors across individuals in IMvigor211. Only PRSs significantly associated with OS in the atezolizumab arm at an FDR of 10% are shown. PRS GWAS p-value cutoffs are provided in parentheses. Rank correlations with $p \geq 0.05$ are labeled ns. TMB=tumor mutational burden, IC IHC=immune cell immunohistochemistry, TC IHC=tumor cell immunohistochemistry, T-eff=T-effector gene signature score of tumor.

Overall, the 95% confidence intervals for hazard ratios, expressed as per unit PRS, were consistent across PRSs computed at a range of GWAS cutoffs for psoriasis and vitiligo (FIG. 2E). Both increased polygenic risk for vitiligo and psoriasis were associated with longer OS under treatment with atezolizumab, whereas decreased polygenic risk for atopic dermatitis was associated with longer OS under atezolizumab treatment. The directionality these associations with OS is consistent with the hypothesis that psoriasis and vitiligo, in contrast to atopic dermatitis, are autoimmune genetic diseases having high $CD4^+$ T-helper-17 polarization (Guttmann-Yasky and Krueger, *Curr. Opin. Immunol.*, 48:68-73, 2017; Guttmann-Yasky et al., *J. Allergy Clin. Immunol.*, 127:1420-1432, 2011; Singh et al., *Autoimmun. Rev.*, 15:397-404, 2016). We confirmed that the OS associations we observed were not simply due to correlation between the T-effector signature and our PRSs (FIG. 8). We quantile normalized the T-effector signature score to allow direct comparison to quantile normalized PRSs. The hazard ratio benefit of a higher T-effector signature score per normalized unit was 0.81, similar to that of the polygenic risk scores per normalized unit for psoriasis, vitiligo, and the inverse of atopic dermatitis (0.78-0.83).

Figure 3A:
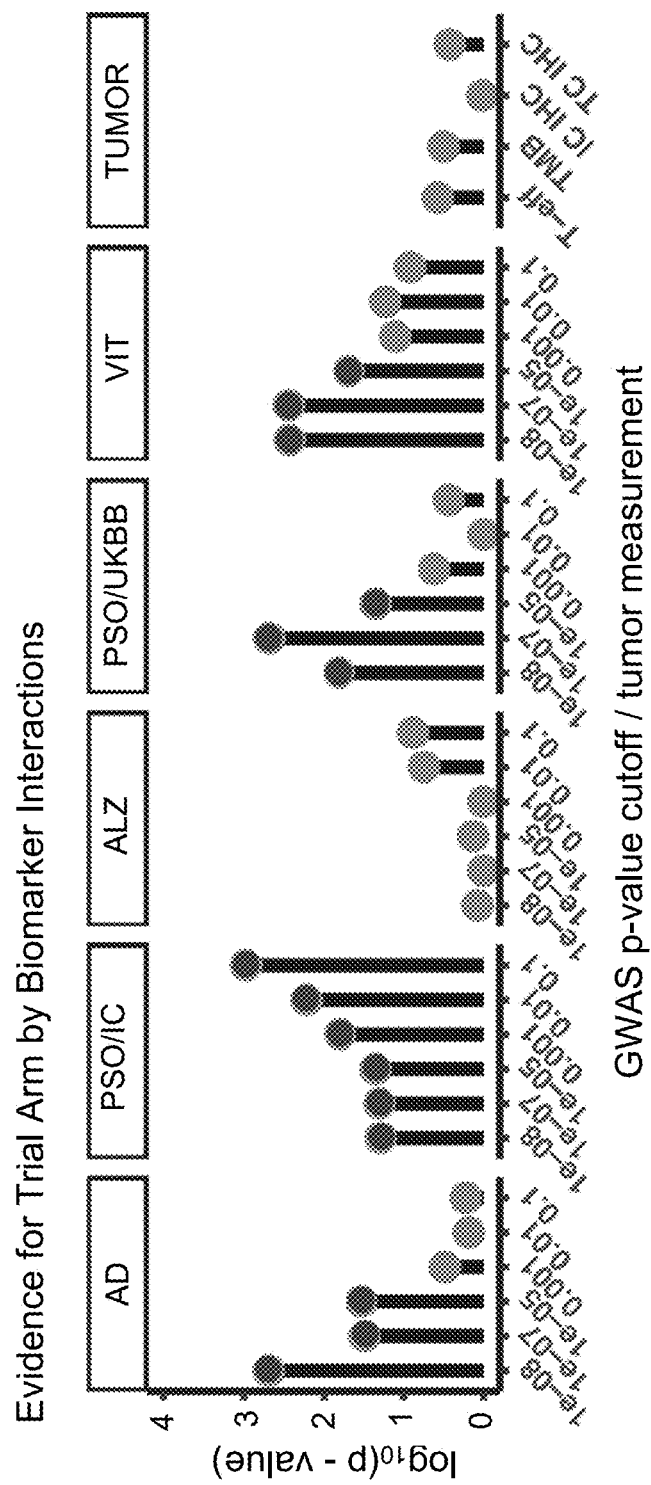
FIG. 3A is graph showing negative $\log_{10}$ p-values for a given PRS testing for a statistically significant trial arm by PRS/biomarker interaction using a Cox proportional hazards model for overall survival. Tests controlled for 5 genotype PCs, gender, and prognostic covariates. Light-colored circles designate PRS and trial arm interaction terms that are significant at an FDR of 10%. Dark-colored circles indicate values that did not reach statistical significance.
Figure 9:
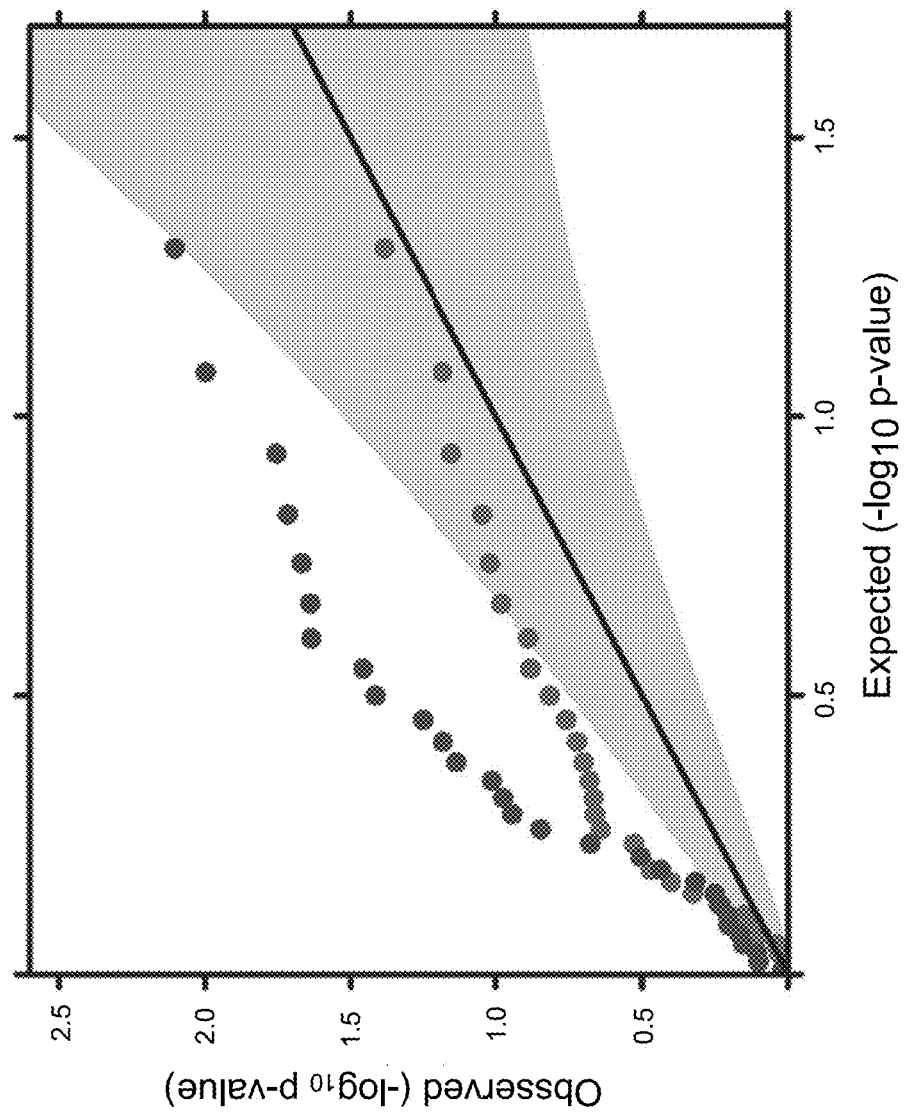
FIG. 9 is a quantile-quantile (Q-Q) plot of p-values associating PRSs at differing GWAS p-value cutoffs and across dermatological autoimmune diseases with OS. Negative $\log_{10}$ p-values from the atezolizumab arm and the chemotherapy arm are plotted against quantiles of a uniform p-value distribution. Shaded region provides the 95% confidence interval where negative $\log_{10}$ p-values are expected to be uniformly distributed. p-values from the atezolizumab arm deviate significantly from the null distribution. A much weaker deviation from a uniform p-value distribution indicates that some of the PRSs might be associated with OS in the chemotherapy arm.

The absence of statistical association signal between PRSs and OS in the chemotherapy arm of IMvigor211 does not necessarily establish PRSs as predictive biomarkers for response to atezolizumab. Evidence of genetic association within the chemotherapy arm of IMvigor211 might indicate that PRSs are prognostic and not predictive (FIG. 9). To test whether a PRS is predictive, we incorporated both trial arms into a Cox proportional hazards model and assessed interaction between the PRS and trial arm (Amur et al., *Clin. Pharmacol. Ther.*, 98:34-46, 2015). After controlling for baseline covariates, a significant trial arm by PRS interaction term identifies PRSs where, for a given increase or decrease in PRS, the hazard ratio between arms changes significantly. At an FDR of 10%, we found that PRSs for atopic dermatitis, psoriasis and vitiligo were predictive biomarkers of OS in IMvigor211 (FIG. 3A). Consistent with prior reporting of the IMvigor211 study, tumor measurements were not strongly predictive of OS within the biomarker available population (Powles et al., *Lancet*, 391:748-757, 2018). Consistent with expectation, our negative control PRSs for Alzheimer's disease were not found to be predictive.

Figure 3B:
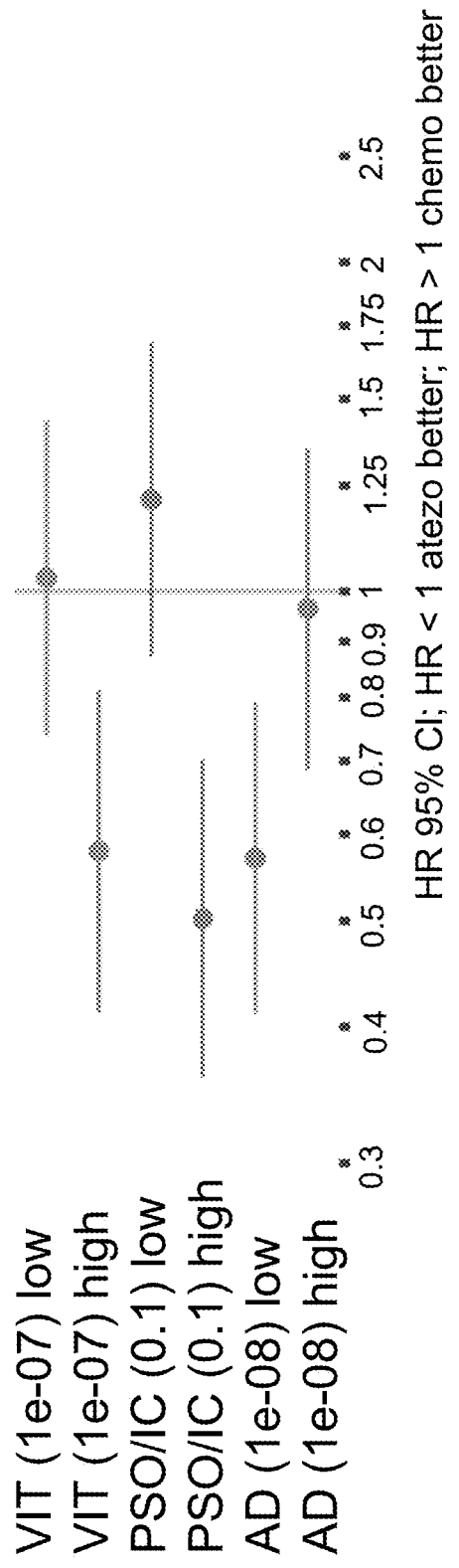
FIG. 3B is a graph showing HRs and 95% CIs for Cox proportional hazard models comparing trial arms in subgroups of high and low risk for PRSs that showed the strongest trial arm by PRS interaction. HRs were adjusted for baseline prognostic covariates, genotype PCs, and gender. High and low risk groups were defined by splitting the entire biomarker available population on the median. Respective GWAS p-value cutoffs of the corresponding PRSs are indicated in parentheses.
Figure 3C:
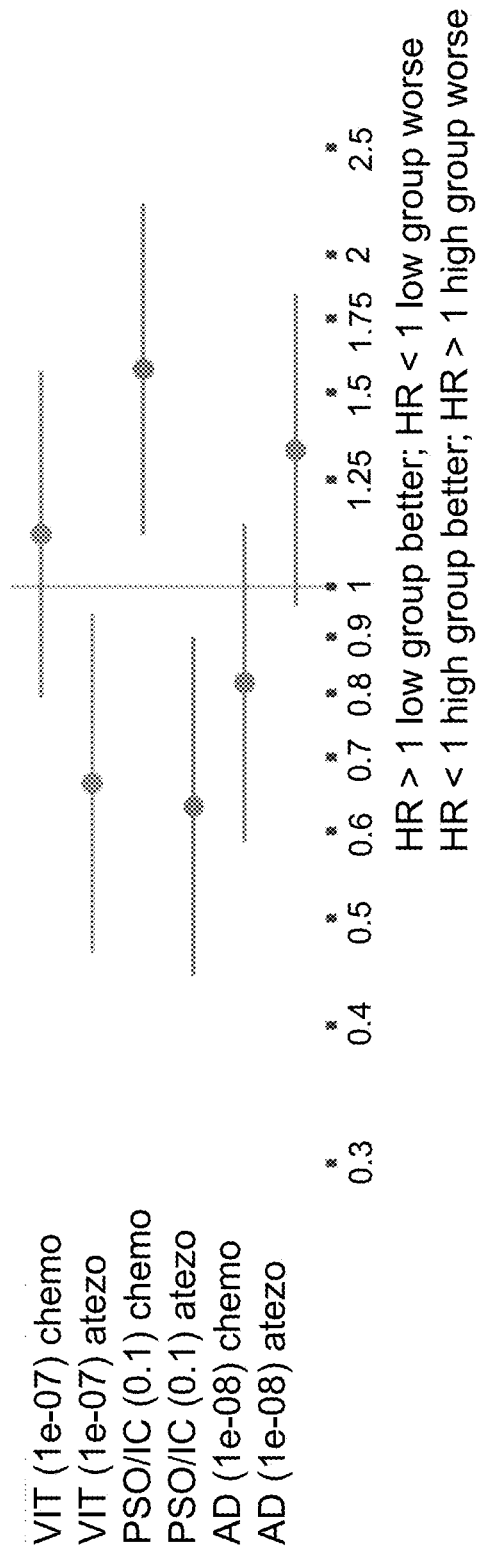
FIG. 3C is a graph showing HRs and 95% CIs from Cox proportional hazard models comparing OS of subgroups of high and low PRSs within each trial arm.
Figure 10:
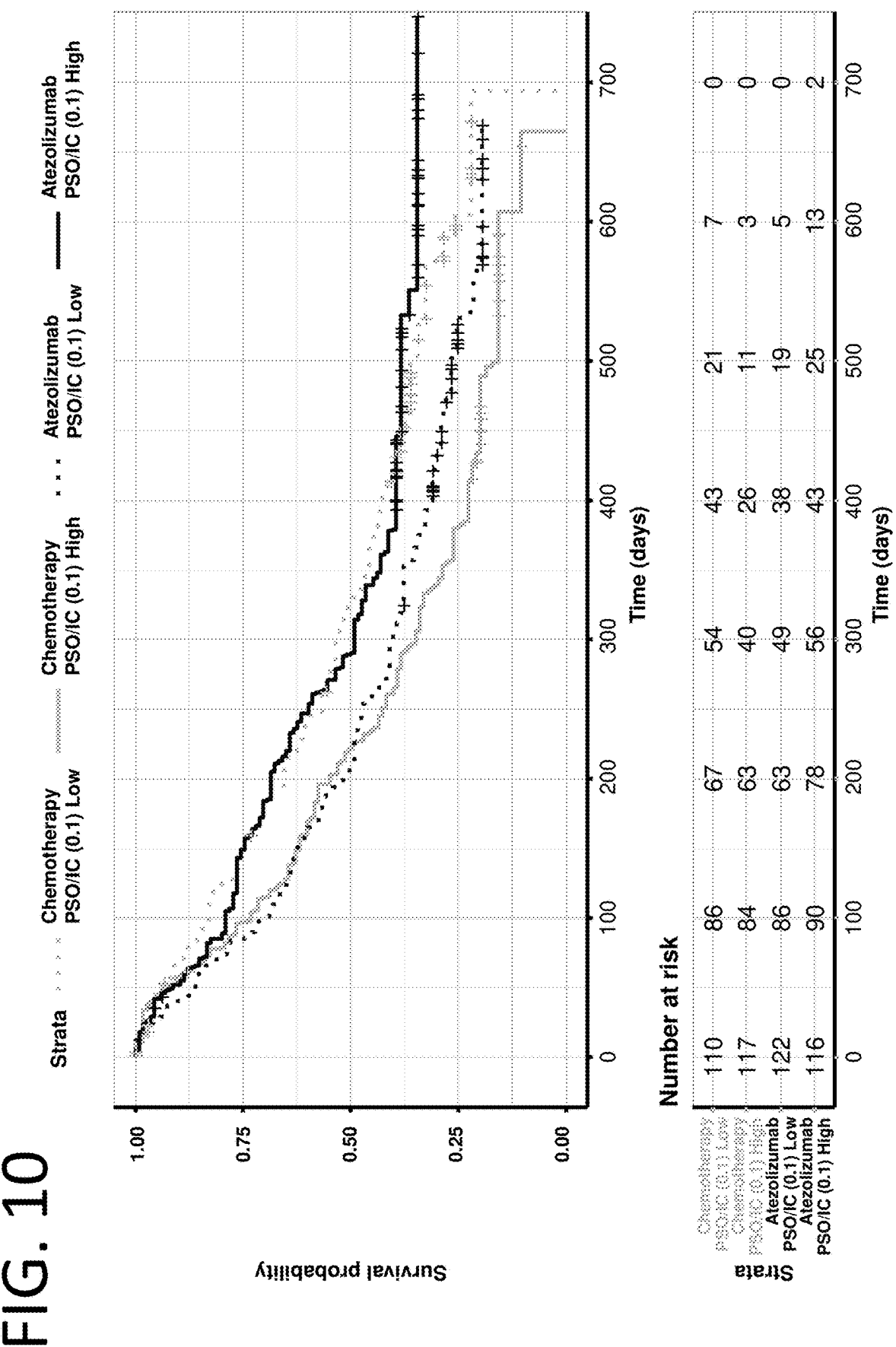
FIG. 10 is a Kaplan-Meir plot of OS comparing atezolizumab to chemotherapy for individuals that had high or low genetic risk for psoriasis. Plot used the PRS derived from the PSO/IC psoriasis study at a GWAS p-value cutoff of 0.1. Dashed lines show the low risk group. Tick marks designate censoring.
Figure 11:
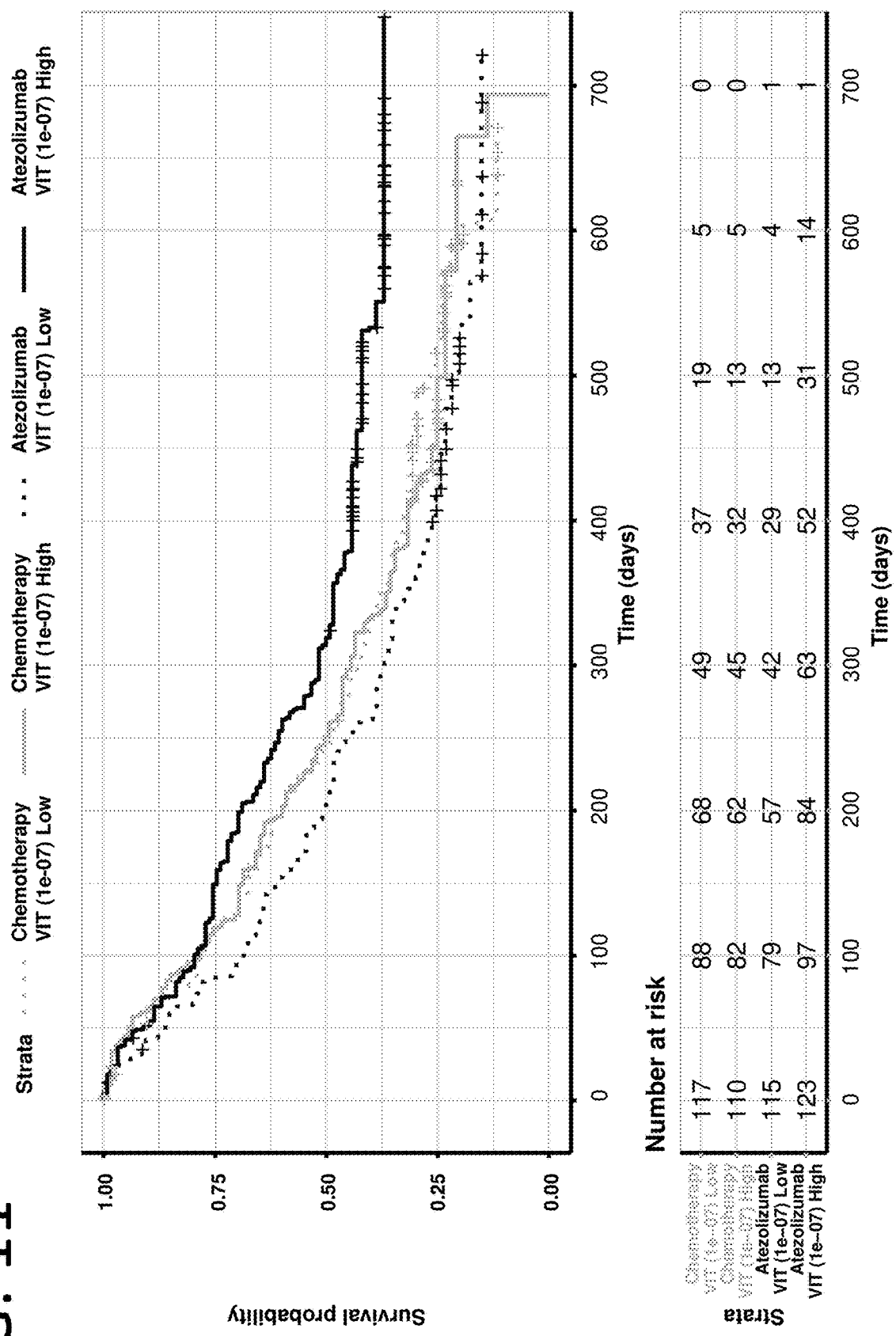
FIG. 11 is a Kaplan-Meir plot of OS comparing atezolizumab to chemotherapy for individuals that had high or low genetic risk for vitiligo. Plot used the PRS derived from SNPs that met a GWAS p-value cutoff of $1 \times 10^{-7}$. Dashed lines show the low risk group. Tick marks designate censoring.
Figure 12:
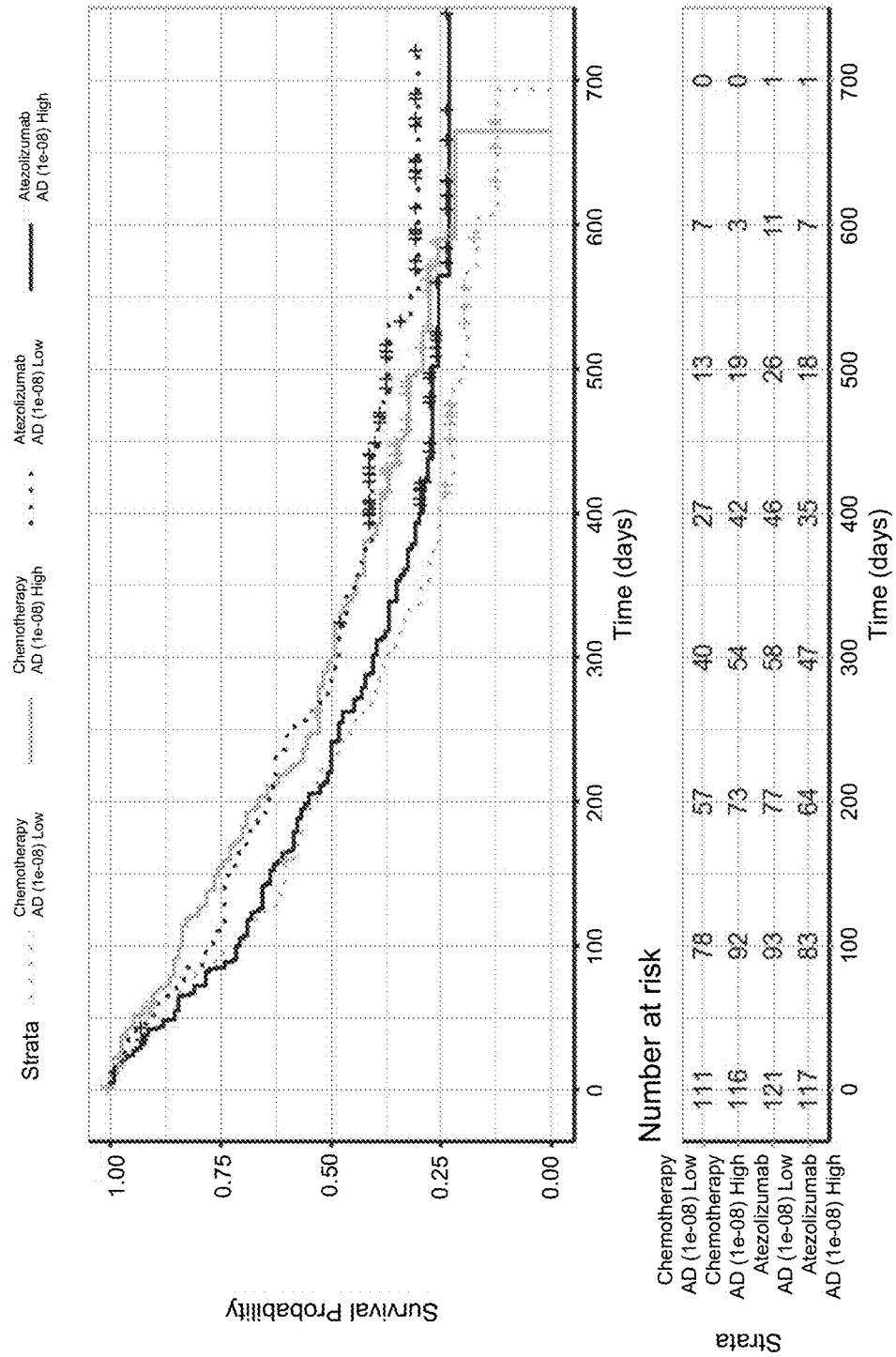
FIG. 12 is a Kaplan-Meir plot of OS comparing atezolizumab to chemotherapy for individuals that had high or low genetic risk for AD. Plot used the PRS derived from SNPs that met a GWAS p-value cutoff of $1 \times 10^{-8}$. Dashed lines show the low risk group. Tick marks designate censoring.
Figure 13:
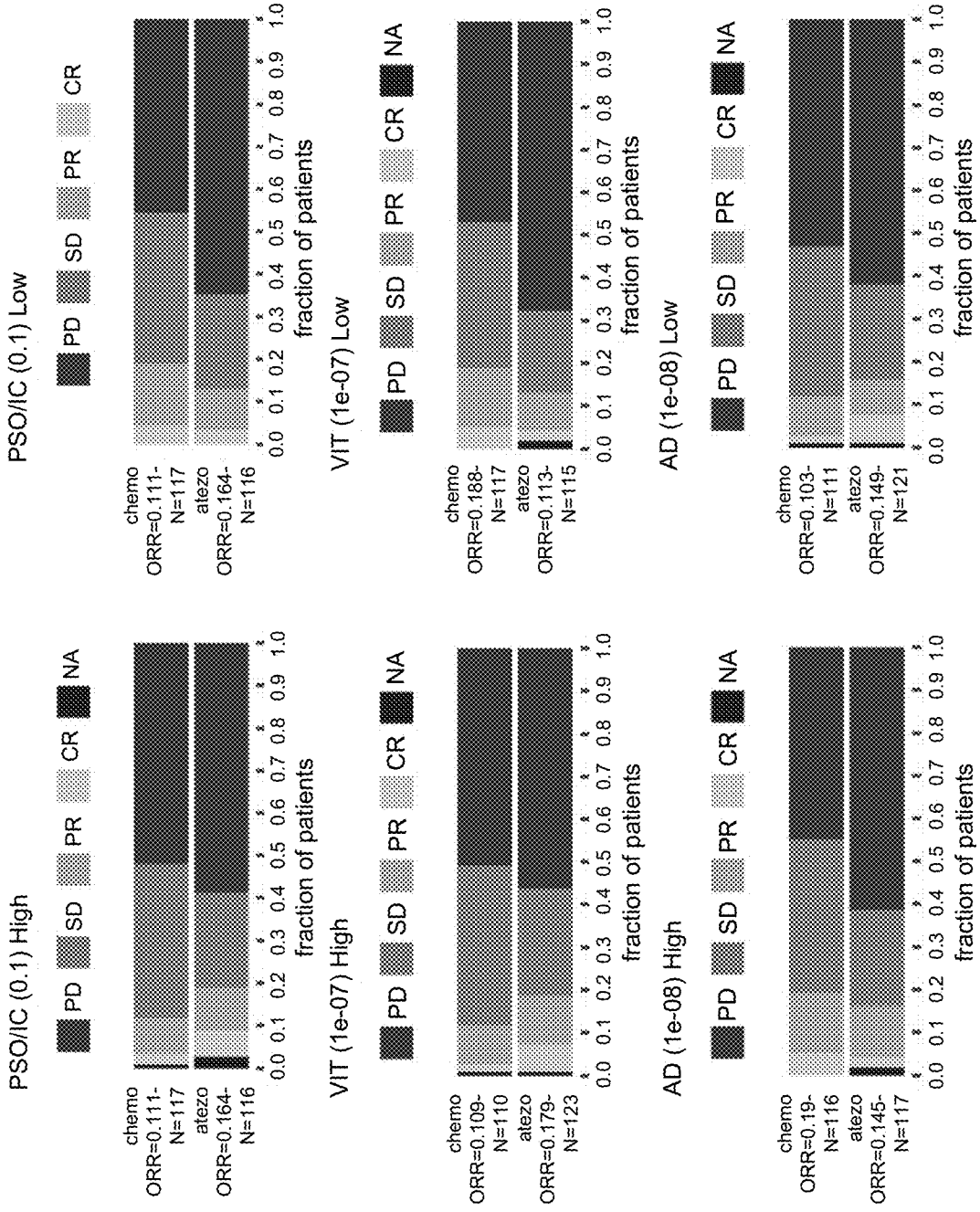
FIG. 13 is a set of graphs showing ORRs to chemotherapy or atezolizumab treatment. High and low genetic risk groups were defined using PRSs that were the most strongly predictive as measured by a PRS by trial arm interaction. The corresponding GWAS p-value cutoff used for the PRS is shown in parentheses. PD, SD, PR, and CR indicate progressive disease, stable disease, partial response, and complete response respectively. NA designates individuals for which BCOR data were unavailable.

To better understand the behavior of the PRSs, we split the entire IMvigor211 biomarker available population on median PRS for a given disease, creating two subgroups of individuals having "high" (above median) or "low" (below median) polygenic risk for said disease. We focused on the respective PRSs that had the strongest trial arm by risk score interaction for each dermatological autoimmune disease. High vitiligo (p=0.0016; HR 0.58; 95% CI 0.41-0.81) and high psoriasis risk (p=5.5×10$^{-5}$; HR 0.50; 95% CI 0.36-0.70) individuals had better OS under checkpoint blockade than chemotherapy, whereas low atopic dermatitis risk (p=0.0008; HR 0.57; 95% CI 0.41-0.79) individuals had improved OS under atezolizumab treatment as compared to chemotherapy (FIG. 3B; FIG. 10-FIG. 12). These results, as in the atezolizumab arm alone, were consistent with high and low Th17 polarization of these diseases respectively (Guttmann-Yasky and Krueger, *Curr. Opin. Immunol.*, 48:68-73, 2017; Singh et al., *Autoimmun. Rev.*, 15:397-404, 2016). To gain further insight into the predictive nature of the PRSs, we compared high and low PRS subgroups within each treatment arm (FIG. 3C). The predictive capacity of high vitiligo risk was explained by improved OS in the atezolizumab arm, whereas psoriasis risk high and AD risk low groups were explained by both improved OS in the atezolizumab arm and reduced OS within the chemotherapy arm. As best confirmed objective response (BCOR) is a proxy for longer and shorter OS, we found that the response rates within the subgroups PD (progressive disease), SD (stable disease), PR (partial response), and CR (complete response) followed a similar numeric pattern (FIG. 13).

Example 5. HLA Associations with Overall Survival and Addition of HLA Effects to Disease-Specific PRS Variants in the MHC locus and specific HLA alleles have been associated with genetic risk for psoriasis, vitiligo, and atopic dermatitis (Weidinger et al., *Hum. Mol. Genet.*, 22:4841-4856, 2013; Okada et al., *Am. J. Hum. Genet.*, 95:162-172, 2014; Li et al., *Biomed Res. Int.*, 2016:5412806, 2016). For example, alleles such as HLA-C*06:02 have been shown to be associated with psoriasis risk at odds ratios >3 (Table 3). Associations between single human leukocyte antigen (HLA) variants and overall survival (OS) were tested for using a Cox proportional hazards model, using the same set of covariates described above for PRS association testing. HLA associations are usually not considered in the selection of SNPs for polygenic risk scores, both due to their disproportionate contribution in terms of variance explained in many diseases, and the complexity of the MHC locus in terms of variability and linkage equilibrium. To assess whether inclusion of HLA variants can improve the PRS associations, we added the effect of HLA alleles previously reported to be associated with Psoriasis, Atopic Dermatitis, and Vitiligo to the respective PRS, making the following simplifying assumptions. (1) Since HLA alleles were imputed at G group resolution, it was assumed that all carriers of a given G group allele were carriers of the 4-digit allele of interest in the given G group. (2) For reported associations of HLA amino acid residues, carriers of those residues were identified by the amino acid sequences of their inferred HLA alleles and categorized accordingly (see Table 4). For reported associations on the level of HLA serotypes, patients were also categorized according to their carrier status for an allele belonging to the respective serotype (see Table 4). (3) Given the strong associations of the HLA variants in the original studies (Table 1), it was assumed they would reach the most stringent PRS p-value cutoff in the respective GWAS, and their effects were therefore added to all PRS cutoffs.

HLA log odds ratios for risk were added to the PRS before quantile normalization, treating each allele as a further single variant adding to the polygenic model. Hence, we added the log odds ratio of the reported HLA allele associations times the number of copies of the allele to the PRS, followed by quantile normalization. Association testing was then performed with overall survival and PRS+HLA by Trial Arm Interactions, using the same methodology as described above for the PRS analyses.

Figure 14:
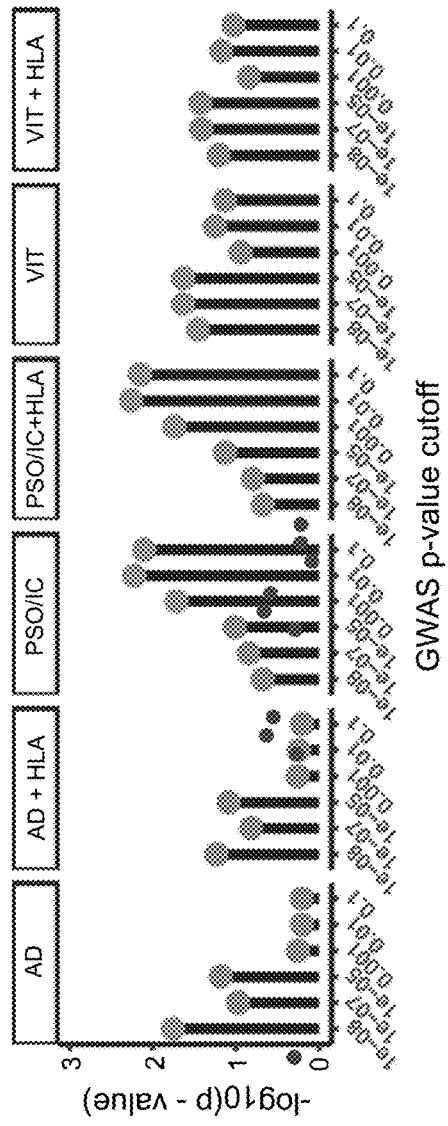
FIG. 14 is a set of graphs showing negative $\log_{10}$ p-values for a given GWAS and p-value cutoff PRS with and without contribution of relevant HLA variants, testing for association with OS in the atezolizumab arm (upper panel) and for a statistically significant trial arm by PRS interaction (lower panel) using a Cox proportional hazards model for OS. Tests controlled for five genotype principal components and several baseline prognostic factors. Light-colored circles show associations significant at an FDR of 10% by the Benjamini-Hochberg (BH) procedure. HLA contributions were tested only in diseases showing significant PRS associations.
Figure 14:
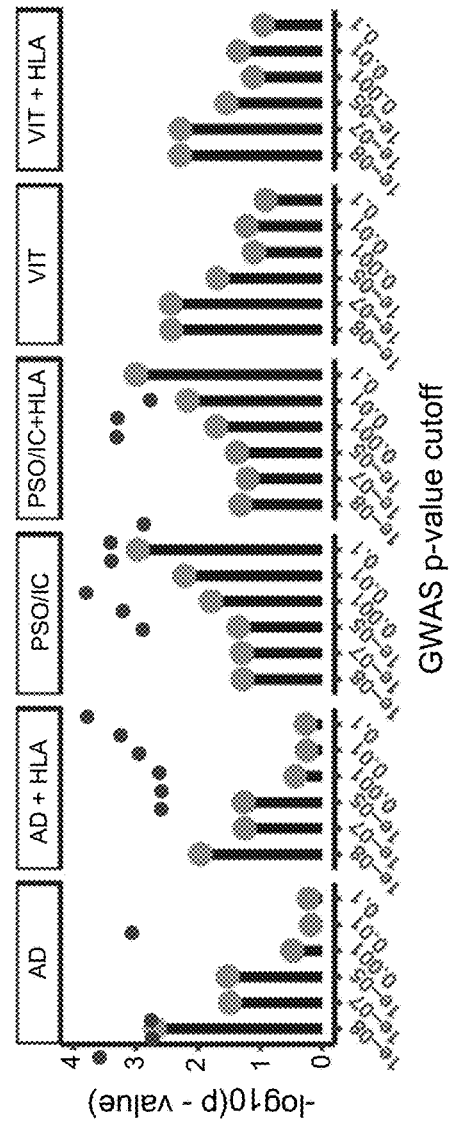

We found that HLA alleles previously found to be associated with risk of psoriasis, atopic dermatitis, or vitiligo were not associated with OS in the atezolizumab or the chemotherapy arm of IMvigor211 (Table 4). As these alleles may contribute additively to risk of dermatological autoimmunity, we incorporated the risk conferred by these alleles to our PRSs (see Methods). Inclusion of this additional information had negligible impact on the associations we observed between OS and PRSs in the atezolizumab arm or the predictive capacity of the PRSs across trial arms (FIG. 14). These analyses indicate that the non-HLA risk for dermatological autoimmunity drives the associations we observe between OS and PRSs.

TABLE 3

Selection of HLA alleles for statistical testing.

| Allele, Amino Acid residue or Serotype | Disease | P | OR | 4-digit alleles covered by AA position or serotype |
|---|---|---|---|---|
| HLA-C*06:02 | Psoriasis | $2.1 \times 10^{-201}$ | 3.26 | |
| HLA-C*12:03 | Psoriasis | $6.5 \times 10^{-12}$ | 1.38 | |
| HLA-B p.67 Cys | Psoriasis | $6.0 \times 10^{-35}$ | 1.56 | B*14:02, B*15:10, B*15:18, B*27:02, B*27:05, B*39:01 |
| HLA-B p.67 Met | Psoriasis | $2.61 \times 10^{-13}$ | 1.44 | B*57:01, B*57:03, B*58:02 |
| HLA-B p.9 Asp | Psoriasis | $1.61 \times 10^{-9}$ | 1.33 | B*08:01 |
| HLA-A p.95 Val | Psoriasis | $4.7 \times 10^{-28}$ | 1.31 | A*02:01, A*02:06, A*69:01 |
| HLA-DRB1*07:01 | Atopic Dermatitis | $1.4 \times 10^{-7}$ | 0.65 | |
| B*44:02 | Atopic Dermatitis | $9.6 \times 10^{-5}$ | 1.39 | |
| HLA-A02 | Vitiligo | <0.0001 | 1.52 | A*02:01, A*02:02, A*02:03, A*02:05, A*02:06, A*02:07, A*02:11 |
| HLA-A33 | Vitiligo | <0.0001 | 2.23 | A*33:01, A*33:03 |

HLA alleles, amino acid residues, and serotypes were selected based on published associations with psoriasis (Dudbridge, PLoS Genet., 9: e1003348, 2013), atopic dermatitis (Torkamani et al., Nat Rev. Genet., 19, 581-590, 2018), and vitiligo (Chatterjee et al., Nat. Rev. Genet., 17, 392-406, 2016).

TABLE 4

HLA associations with OS in IMvigor211 atezolizumab and chemotherapy arms.

| Allele, Amino Acid residue or Serotype | Atezolizumab Arm | | | Chemotherapy Arm | | |
|---|---|---|---|---|---|---|
| | HR | Std Error | P | HR | Std Error | P |
| HLA-B*44:02:01G | 0.98 | 0.28 | 0.93 | 1.08 | 0.26 | 0.76 |
| HLA-C*06:02:01G | 0.77 | 0.25 | 0.30 | 0.78 | 0.25 | 0.32 |
| HLA-C*12:03 | 0.86 | 0.26 | 0.57 | 1.04 | 0.25 | 0.89 |
| HLA-DRB1*07:01:01G | 0.98 | 0.19 | 0.90 | 0.86 | 0.20 | 0.43 |
| HLA-B p.67 Cys | 0.78 | 0.25 | 0.31 | 1.13 | 0.23 | 0.60 |
| HLA-B p.67 Met | 1.09 | 0.35 | 0.80 | 1.05 | 0.38 | 0.90 |
| HLA-B p.9 Asp | 2.20 | 0.43 | 0.07 | 0.87 | 0.36 | 0.69 |
| HLA-A p.95 Val | 1.11 | 0.17 | 0.54 | 1.15 | 0.17 | 0.42 |
| HLA-A02 | 1.14 | 0.17 | 0.45 | 1.17 | 0.17 | 0.35 |
| HLA-A33 | 0.77 | 0.47 | 0.58 | 1.49 | 0.50 | 0.42 |

Selected HLA alleles, amino acid residues, and serotypes were tested for association with overall survival in IMvigor211 atezolizumab and chemotherapy arms. Hazard ratio (HR) <1 indicates that OS under atezolizumab is higher.

Example 6. Association of Pre-Existing Tumor Immunity with the Predictive Capacity of PRSs Using pre-treatment bulk tumor gene expression for N=398 individuals with both RNA-seq and germline genetic data, we asked whether the predictive capacity of our PRSs was associated with several tumor-associated factors of the individual, including high or low pre-existing CD8+ T-effector function and tumor expression of T-helper chemokines and cytokines involved in differentiation, recruitment, and response.

A. Pre-Treatment Tumor RNA-Seq

The pathologic diagnosis of each case was confirmed by assessing the presence of tumor cells on hematoxylin and eosin (H&E)-stained slides of putative tumor tissue. All samples that advanced to nucleic acid extraction contained a minimum of 20% tumor cells. H&E images were marked for macro-dissection by a pathologist and were macro-dissected. RNA was then extracted from the macro-dissected sections (High Pure FFPET RNA Isolation Kit, Roche). Tumor RNA-seq data was generated using TruSeq RNA Access technology (Illumina). Reads were first aligned to ribosomal RNA sequences to remove ribosomal reads. The remaining reads were aligned to the human reference genome (NCBI Build 38) using GSNAP version 2013 Oct. 10 (Wu and Nacu, Bioinformatics, 26:873-881, 2010), allowing maximum of two mismatches per 75 base sequence. (parameters: -M 2 -n 10 -B 2 -i 1 -N 1 -w 200000 -E 1 --pairmax-rna=200000 --clip-overlap).

To quantify gene expression levels, the number of reads mapped to the exons of each RefSeq gene was calculated using the functionality provided by the R package GenomicAlignments (Bioconductor) (Lawrence et al., PLoS Comput. Biol., 9: e1003118, 2014). RNA-seq library size L was estimated using the TMM method to estimate norm factors in edgeR (e.g. L=normFactor*total number of reads in sample). For each gene/sample count, we computed counts per million using a pseudo count $(C+0.5)/(L+1)*1\times10^6$ following limma/voom where C was the read count of the gene in a given sample Law et al., Genome Biol., 15: R29, 2014). The resulting counts per million values were scaled by gene length to obtain normalized Reads Per Kilobase Million (RPKM) values. We estimated 10 probabilistic estimation of expression residuals (PEER) factors directly on the normalized $\log_2$ counts per million values to account for batch effects in tumor RNA-seq (Stegle et al., *PLoS Comput. Biol.*, 6: e1000770, 2010).

B. CD8+ T-Effector Signature Score Computation

To construct the T-effector signature, the following gene set of G=8 genes was used: CD8A, GZMA, GZMB, INFG, CXCL9, CXCL10, PRF1 and TBX21, as defined in Rosenberg et al., *Lancet*, 387:1909-1920, 2016. The signature was constructed by first z transforming the log 2 counts per million values for each gene in the gene set across the N tumor RNA seq samples in a given data set and then performing a singular value decomposition (principal component analysis) of the resulting G×N data matrix. The first principal component (PC1) is by definition the T-effector signature for the given data set. It is by construction a weighted sum of the genes in the gene set, focusing the score on the largest block of well-correlated genes in the set, while down-weighing contributions from genes that do not track with other members of the gene set.

C. Additional Tumor-Associated Factors

Data on immune cell (IC) and tumor cell (TC) staining of PD-L1 by immunohistochemistry (IHC), as well as tumor mutation burden, was obtained using methods described in the previous publication and protocols for IMvigor211 (Powles et al., *Lancet*, 391:748-757, 2018).

D. Tumor Gene Expression and PRS Predictive Capacity Associations

We tested whether high or low tumor gene expression was associated with the capacity of PRSs to predict overall survival. We focused on tumor gene expression of T-cell differentiation, and recruitment and response cytokines and chemokines, filtering for those genes with median RPKM>0.1 and median read count of >10 across individuals (Table 5). We limited our analysis to the PRSs that were most strongly predictive of overall survival (identified by their GWAS p-value cutoff, FIG. 3B). PRSs and tumor gene expression values were transformed into categorical variables (high and low) on the basis of median splits across the entire IMvigor211 population. This approach made minimal assumptions about the relative scale of PRSs and tumor gene expression values. To determine whether the predictive capacity of a PRS was associated with a tumor-associated factor, we tested for a non-zero 3-way interaction term between PRS (high/low) by trial arm (atezolizumab/chemotherapy) by tumor-associated factor/RNA-seq (high/low) in a Cox proportional hazards model for overall survival. The Cox proportional hazards model also contained all lower order interaction terms. p-values were computed using the Wald test on the coefficient of this 3-way interaction term using the survival package in R. False discovery rate (FDR) was estimated using the Benjamini-Hochberg (BH) procedure (Benjamini and Hochberg, Journal of the Royal Statistical Society. Series B (Methodological), 57:289, 1995). We controlled for the same baseline factors described above in our tests for association between PRSs and survival. We additionally included 10 PEER factors to account for batch effects in tumor RNA-seq data.

TABLE 5

Tumor genes tested for association with the predictive capacity of PRSs.

| Gene Set Description | Genes |
| --- | --- |
| Treg Differentiation | IL2, TGFB1 |
| Treg Recruitment | CCL20 |
| Treg Response | TGFB1, IL10, IL35 (EBI3, IL12A) |
| Th1 Differentiation | IL12 (IL12A, IL12B) |
| Th1 Recruitment | CXCL9, CXCL10, CXCL11 |
| Th1 Response | IFNG, TNF |
| Th2 Differentiation | IL4 |
| Th2 Response | IL4, IL13 |
| Th9 Differentiation | IL4, TGFB1 |
| Th9 Response | IL9, IL10 |
| Th17 Differentiation | IL6, IL23 (IL12A, IL23A), IL1B, TGFB1 |
| Th17 Recruitment | CCL20 |
| Th17 Response | IL17A, IL17F, CXCL1, CXCL2, CXCL5 |
| Th22 Differentiation | IL6, TNF |
| Th22 Response | IL22 |
| Tfh Differentiation | IL6, IL21 |
| Tfh Response | IL6, IL21 |
| CD8+ T-effector | CD8A, GZMA, GZMB, IFNG, CXCL9, CXCL10, PRF1, TBX21 |

Cytokines that are heterodimers are italicized with genes in parentheses. Genes with median RPKM>0.1 and median count >10 across individuals in bulk tumor RNA-seq are underlined. Gene sets were adapted from Keir et al., *J. Exp. Med.*, 179:5064-5070, 2006; Guttmann-Yasky and Krueger, *Curr. Opin. Immunol.*, 48:68-73, 2017; and Guttmann-Yasky et al., *J. Allergy Clin. Immunol.*, 127:1420-1432, 2011.

Figure 4:
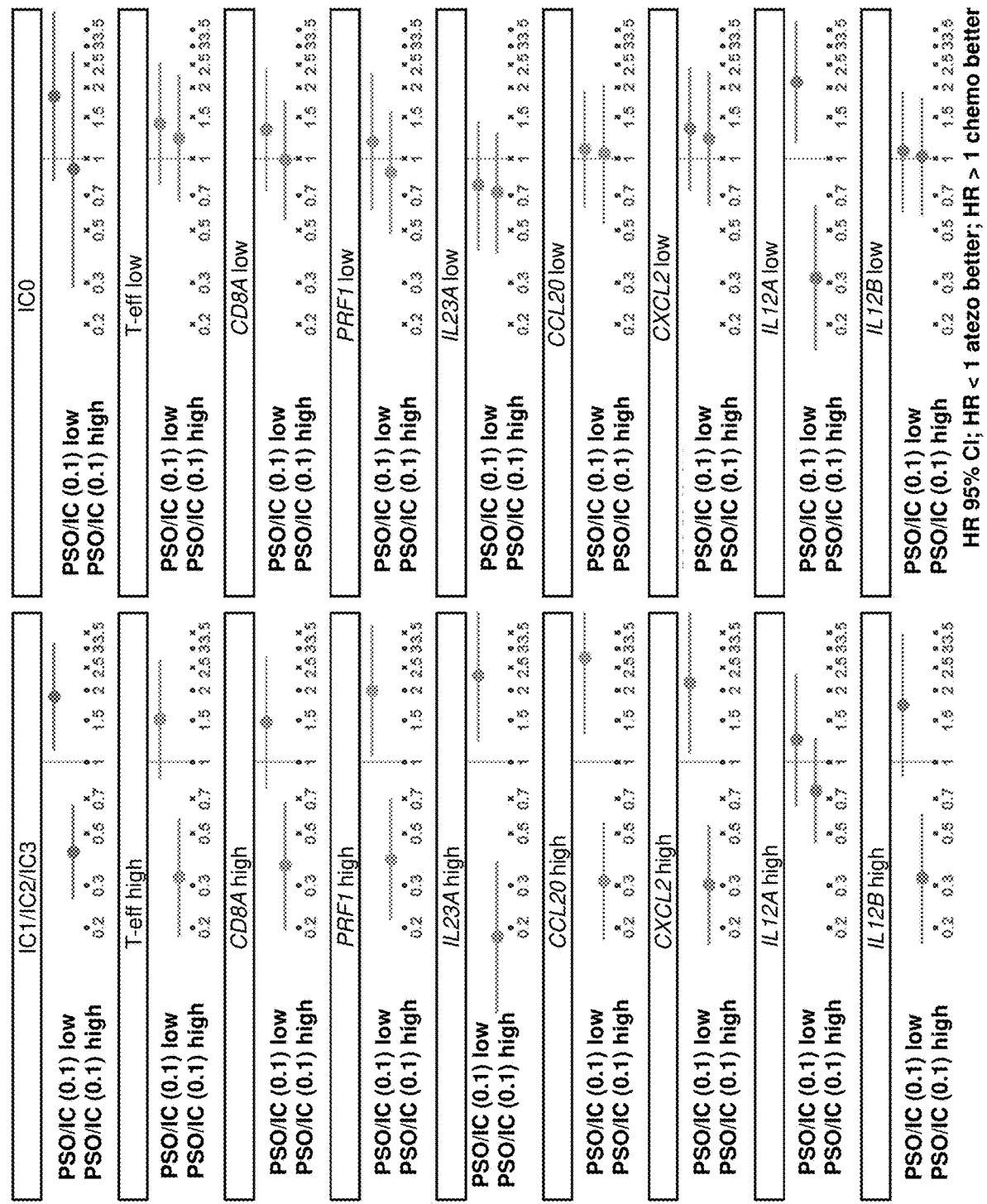
FIG. 4 is a set of graphs showing HRs and 95% CI comparing trial arms in subgroups of high and low risk for psoriasis using the PSO/IC PRS at a GWAS p-value cutoff of 0.1. HRs were adjusted for baseline prognostic covariates, genotype PCs, and gender. High and low PRS groups and gene expression groups were defined by splitting the entire biomarker available population on their respective median values. IC0, 1, 2, and 3 designate differing levels of immune cell (IC) staining of PD-L1 by immunohistochemistry. Only tumor-associated factors and genes associated with the predictive capacity of PRS for psoriasis at an FDR of 10% are shown.
Figure 15:
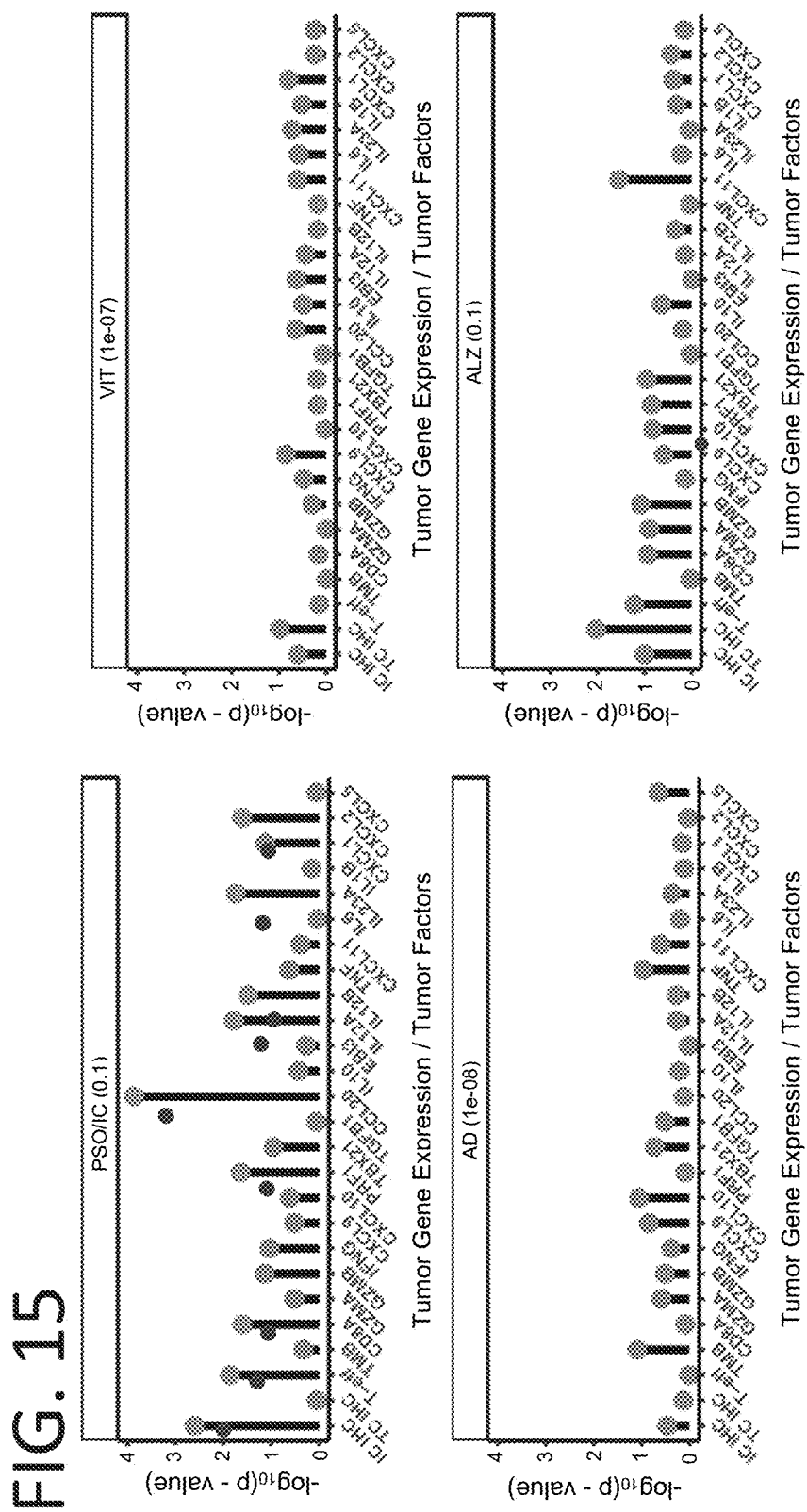
FIG. 15 is a set of graphs showing negative $\log_{10}$ p-values for a given PRS testing whether its predictive capacity was associated with high or low tumor expression of a given T-helper chemokine or cytokine. Associations controlled for several baseline prognostic factors. "High" or "low" was defined by median split of the PRS and median split of tumor gene expression as measured by RNA-seq. High immune cell and tumor cell immunohistochemistry (IHC) for PD-L1 was defined as the IC1/IC2/IC3 and TC1/TC2/TC3 groups, respectively. Light-colored circles designate significant associations at an FDR of 10% estimated using the BH procedure.
Figure 16:
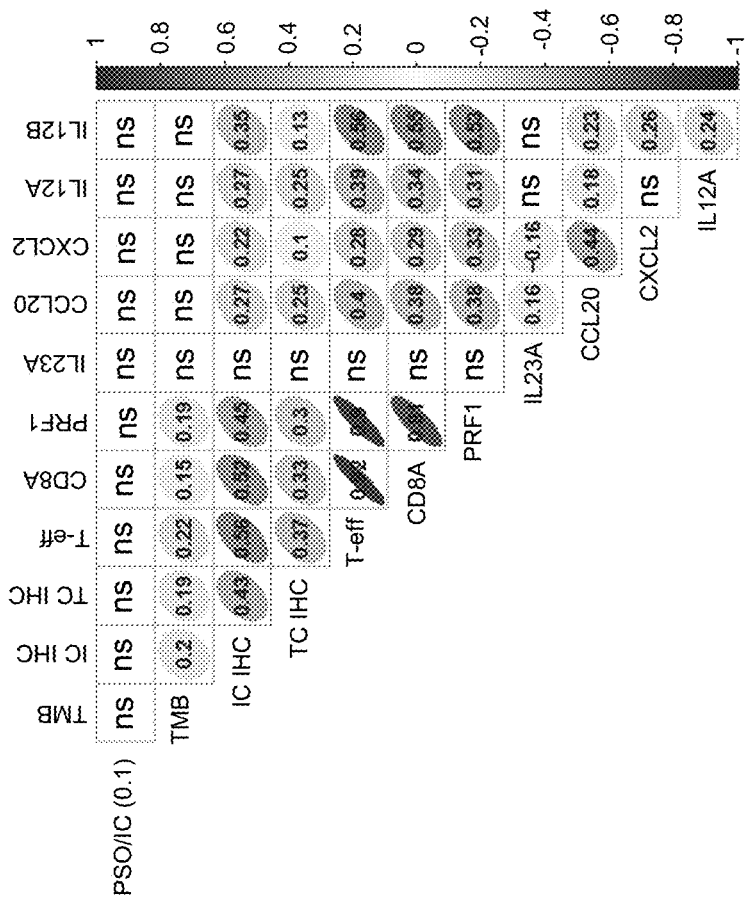
FIG. 16 is a chart showing Spearman's rank correlation across individuals between the PRS for psoriasis for tumor-associated factor and tumor gene expression interactions found to be significant at an FDR of 10%. GWAS p-value cutoff is provided in parentheses. Rank correlations with p≥0.05 are labeled ns. TMB=tumor mutational burden, IC IHC=immune cell immunohistochemistry, TC IHC=tumor cell immunohistochemistry, T-eff=T-effector gene signature score of tumor.

At an FDR of 10%, we found that the predictive capacity of a PRS for psoriasis was associated with several tumor-associated factors and genes (FIG. 15). We confirmed the associations were not due to simple correlation across individuals (FIG. 16). To further understand these associations, we examined the 95% confidence intervals around the hazard ratios, comparing atezolizumab to chemotherapy in each of the subgroups, defined on high or low psoriasis risk and high or low expression of significantly associated tumor-associated factors and genes (FIG. 4). Our analyses delineated pre-treatment tumor conditions under which genetic risk for psoriasis was predictive of OS. Pre-existing immunity as measured by high immune cell (IC) staining of PD-L1 by IHC was associated with benefit from anti-PDL1 in psoriasis high polygenic risk individuals. Consistent with this IC IHC association, high CD8+ T-effector function as measured by CD8A, PRF1, and the T-effector signature score were also associated with the predictive capacity of the PRS for psoriasis.

Although IL-17A and IL-17F expression was not detected at appreciable levels in tumor RNA-seq data, IL-17 induced genes were considered, including CXCL2, a neutrophil chemoattractant, and CCL20, a ligand for CCR6 and a chemoattractant for Th17 and Treg cells. Notably, both were associated with the predictive capacity of a PRS for psoriasis. High gene expression of IL23A also stratified across the trial arms in individuals with high risk of psoriasis. Each of these associations support a role for Th17 immunity, acting selectively in patients with high PRS for psoriasis. By contrast, Th1-associated genes were not as strongly associated with the predictive capacity of PRS for psoriasis (FIG. 16). Interestingly, higher expression of CXCL2, CCL20, or IL23A in patients with low PRS for psoriasis was associated with better OS under chemotherapy. These results suggest that higher expression of IL-17-induced cytokines and chemokines might be beneficial only for patients with defined genetic backgrounds (FIG. 4).

Figure 17:
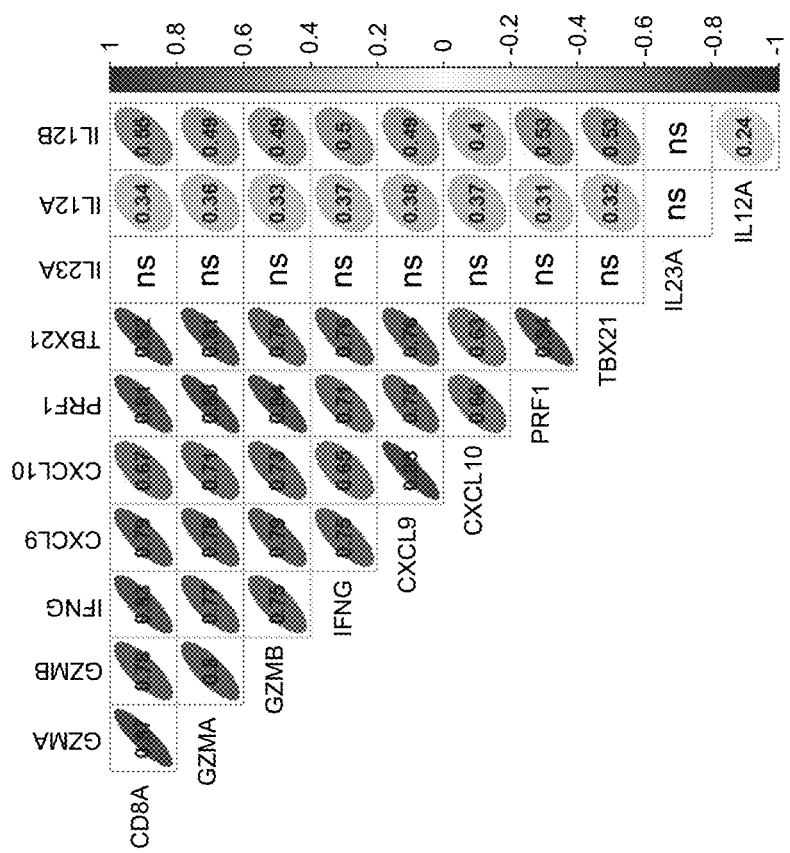
FIG. 17 is a chart showing Spearman's rank correlation between IL23A, IL12A, and IL12B and $CD8^+$ T-effector signature genes across individuals in IMvigor211. Rank correlations with p≥0.05 are labeled ns.
Figure 18:
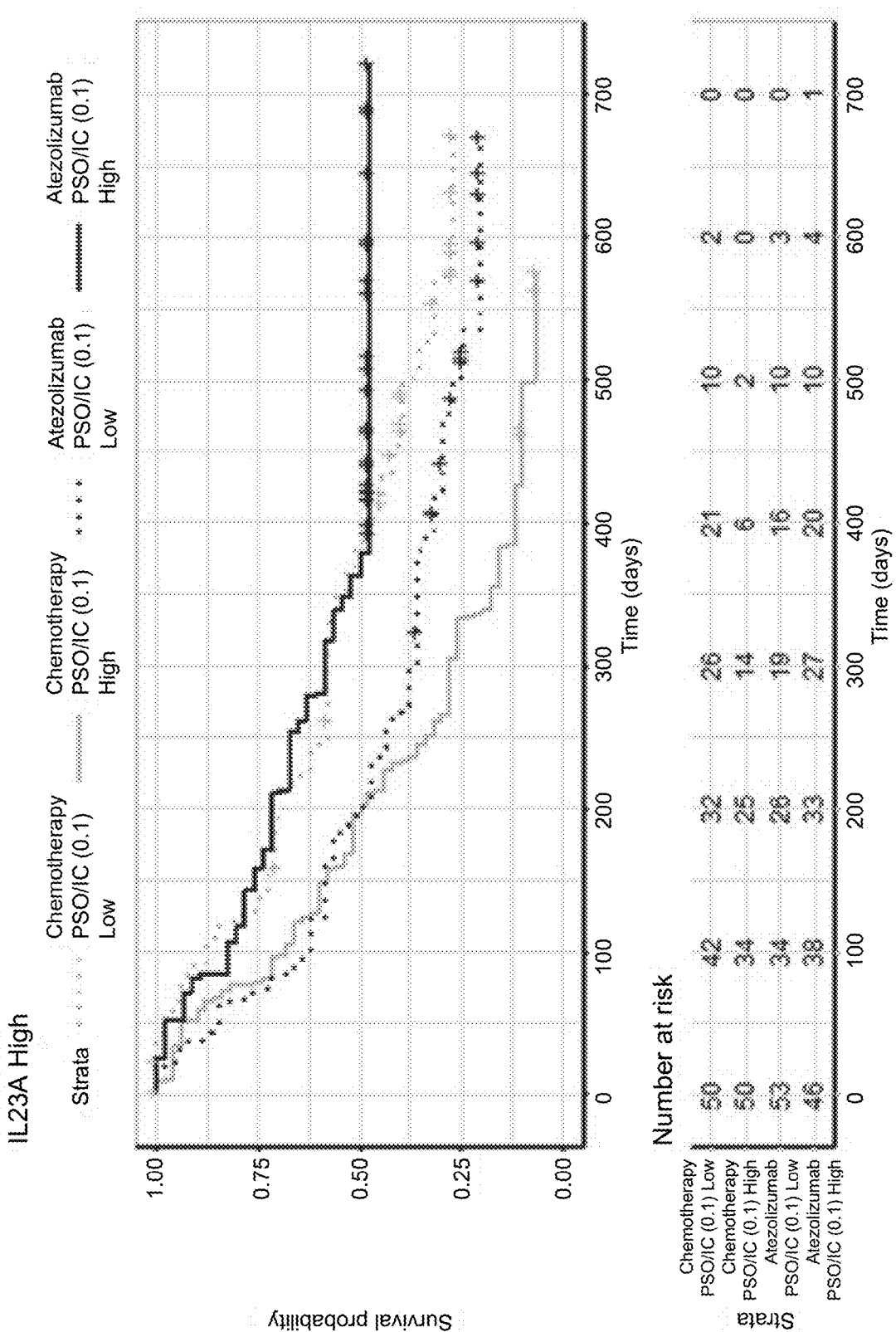
FIG. 18 is a set of Kaplan-Meir plots of OS comparing atezolizumab to chemotherapy for individuals that had high or low genetic risk for psoriasis split on median tumor gene expression (above median="high", left column; below median="low", right column) of IL23A (p19), IL12A (p35), and IL12B (p40). PRS was derived from the PSO/IC study at a GWAS p-value cutoff of 0.1. Dashed lines show the low psoriasis risk group. Tick marks designate censoring.

One final observation concerned the association between low tumor expression of IL12A and the predictive capacity of PRS for psoriasis. IL-12p70 promotes the development of Th1 immunity, whereas IL-23 stabilizes Th17 cells. IL-12 is a heterodimer composed of IL-12p35 (IL12A gene product) and IL12p40 (IL12B gene product). The p40 subunit can also associate with IL23p19 (IL23A gene product) to form IL-23 (Teng et al., *Nat. Med.*, 21:719-729, 2015). Although Th1 immunity is associated with CD8+ T-cell effector function through CD4+ T-cell production of IFN-γ, we found IL12A to be less correlated with CD8+ T-effector signature genes, including IFN-γ, than IL12B (FIG. 17). The role of IL12p70 as capable of limiting late-stage autoimmune inflammation (Kulig et al., *Nat. Commun.*, 7:13466, 2016; Murphy et al., *J. Exp. Med.*, 198:1951-1957, 2003; Becher et al., *J. Clin. Invest.*, 110:493-497, 2002) would be consistent with the observed association of low tumor expression of IL12A and the predictive capacity of psoriasis genetic risk (FIG. 4; FIG. 18). The direction of this association thus adds further support for the importance of Th17-driven autoimmune inflammation in anti-tumor immunity that is induced by PD-L1 blockade.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating an individual having a metastatic urothelial carcinoma (mUC), the method comprising:
(a) determining a determining a polygenic risk score (PRS) for one or more of vitiligo, psoriasis, and atopic dermatitis from a sample from the individual, wherein:
(i) the PRS for vitiligo from the sample is above a vitiligo reference PRS, wherein the vitiligo reference PRS is the median PRS for vitiligo in a reference population;
(ii) the PRS for psoriasis from the sample is above a psoriasis reference PRS, wherein the psoriasis reference PRS is the median PRS for psoriasis in a reference population; or
(iii) the PRS for atopic dermatitis from the sample is below an atopic dermatitis reference PRS, wherein the atopic dermatitis reference PRS is the median PRS for atopic dermatitis in a reference population, thereby identifying the individual as one who may benefit from a treatment comprising atezolizumab; and
(b) administering an effective amount of atezolizumab to the individual.

2. The method of claim 1, wherein the vitiligo, psoriasis, or atopic dermatitis reference PRS is a PRS in a reference population of individuals having the mUC, the population of individuals consisting of a first subset of individuals who have been treated with atezolizumab and a second subset of individuals who have been treated with a non-immune checkpoint inhibitor therapy, wherein the non-immune checkpoint inhibitor therapy does not comprise an immune checkpoint inhibitor and wherein the vitiligo, psoriasis, or atopic dermatitis reference PRS significantly separates each of the first and second subsets of individuals based on a significant difference in responsiveness to treatment with the atezolizumab relative to responsiveness to treatment with the non-immune checkpoint inhibitor therapy.

3. The method of claim 2, wherein responsiveness to treatment is an increase in overall survival (OS).

4. The method of claim 1, wherein the vitiligo, psoriasis, or atopic dermatitis reference PRS is a pre-assigned PRS.

5. The method of claim 4, wherein the vitiligo reference PRS is the median PRS for vitiligo in the reference population; the psoriasis reference PRS is the median PRS for psoriasis in the reference population; or the atopic dermatitis reference PRS is the median PRS for atopic dermatitis in the reference population.

6. The method of claim 1, wherein (a) the PRS for vitiligo, psoriasis, or atopic dermatitis of the sample from the individual or (b) the PRS for vitiligo, psoriasis, or atopic dermatitis of a sample from an individual in the reference population, is calculated using the equation:

$$\hat{S} = \sum_{i=1}^{M} \beta_i \cdot G_i$$

wherein:
(i) $\hat{S}$ is the PRS for vitiligo, psoriasis, or atopic dermatitis;
(ii) M is the number of risk alleles detected in the sample, wherein a risk allele is identified as a SNP having a p-value at or below a given p-value cutoff in a genome-wide association study (GWAS) for vitiligo, psoriasis, or atopic dermatitis;
(iii) i represents the index of a given SNP;
(iv) $\beta_i$ is the log odds ratio of the ith SNP; and
(v) $G_i = \{0,1,2\}$ is the number of copies of the SNP in the sample from the individual.

7. The method of claim 6, wherein the GWAS is a GWAS for vitiligo.

8. The method of claim 6, wherein the GWAS is a GWAS for psoriasis.

9. The method of claim 6, wherein the GWAS is a GWAS for atopic dermatitis.

10. The method of claim 1, further comprising assessing one or more properties that are positively associated with the predictive capacity of a PRS for psoriasis from a sample from a tumor of the individual before administration of a treatment comprising atezolizumab.

11. The method of claim 10, wherein the property is the presence of detectable PD-L1 staining in tumor-infiltrating immune cells covering ≥1% of the tumor area, as assessed by an immunohistochemistry (IHC) assay.

12. The method of claim 10, wherein the property is CD8$^+$ T-effector function that is increased relative to a reference level.

13. The method of claim 10, wherein the property is high expression of CXCL2, CCL20, IL23A, or IL12B.

14. The method of claim 10, wherein the property is low expression of IL12A.

15. The method of claim 1, wherein the sample is a whole blood sample.

16. The method of claim 1, wherein the sample is an archival sample, a fresh sample, or a frozen sample.

17. The method of claim 1, wherein the treatment comprising atezolizumab is a monotherapy.

18. The method of claim 1, wherein the individual has not been previously treated for the mUC.

19. The method of claim 1, wherein the method comprises:
(a) determining a PRS for psoriasis from a sample from the individual, wherein the PRS for psoriasis from the sample is above a psoriasis reference PRS, thereby identifying the individual as one who may benefit from a treatment comprising atezolizumab,
wherein the psoriasis reference PRS is the median PRS for psoriasis in a reference population, and wherein the PRS for psoriasis of the sample from the individual or the PRS for psoriasis of a sample from an individual in the reference population, is calculated using the equation:

$$\hat{S} = \sum_{i=1}^{M} \beta_i \cdot G_i$$

wherein:
(i) $\hat{S}$ is the PRS for psoriasis;
(ii) M is the number of risk alleles detected in the sample, wherein a risk allele is identified as a SNP having a p-value at or below a given p-value cutoff in a GWAS for psoriasis;
(iii) i represents the index of a given SNP;
(iv) $\beta_i$ is the log odds ratio of the ith SNP; and
(v) $G_i = \{0,1,2\}$ is the number of copies of the SNP in the sample from the individual; and
(b) assessing one or more properties that are positively associated with the predictive capacity of a PRS for psoriasis from a sample from a tumor of the individual, wherein the property is:

(i) the presence of detectable PD-L1 staining in tumor-infiltrating immune cells covering ≥1% of the tumor area, as assessed by an immunohistochemistry (IHC) assay;
(ii) CD8+ T-effector function that is increased relative to a reference level;
(iii) high expression of CXCL2, CCL20, IL23A, or IL12B; or
(iv) low expression of IL12A.

20. The method of claim 1, wherein the method comprises:
determining a PRS for vitiligo from a sample from the individual, wherein the PRS for vitiligo from the sample is above a vitiligo reference PRS, thereby identifying the individual as one who may benefit from a treatment comprising atezolizumab,
wherein the vitiligo reference PRS is the median PRS for vitiligo in a reference population, and wherein the PRS for vitiligo of the sample from the individual or the PRS for vitiligo of a sample from an individual in the reference population, is calculated using the equation:

$$\hat{S} = \sum_{i=1}^{M} \beta_i \cdot G_i$$

wherein:
(i) $\hat{S}$ is the PRS for vitiligo;
(ii) M is the number of risk alleles detected in the sample, wherein a risk allele is identified as a SNP having a p-value at or below a given p-value cutoff in a GWAS for vitiligo;
(iii) i represents the index of a given SNP;
(iv) $\beta_i$ is the log odds ratio of the ith SNP; and
(v) $G_i = \{0,1,2\}$ is the number of copies of the SNP in the sample from the individual.

21. The method of claim 1, wherein the method comprises:
determining a PRS for atopic dermatitis from a sample from the individual, wherein the PRS for atopic dermatitis from the sample is below an atopic dermatitis reference PRS, thereby identifying the individual as one who may benefit from a treatment comprising atezolizumab,
wherein the atopic dermatitis reference PRS is the median PRS for atopic dermatitis in a reference population, and wherein the PRS for atopic dermatitis of the sample from the individual or the PRS for atopic dermatitis of a sample from an individual in the reference population, is calculated using the equation:

$$\hat{S} = \sum_{i=1}^{M} \beta_i \cdot G_i$$

wherein:
(i) $\hat{S}$ is the PRS for atopic dermatitis;
(ii) M is the number of risk alleles detected in the sample, wherein a risk allele is identified as a SNP having a p-value at or below a given p-value cutoff in a GWAS for atopic dermatitis;
(iii) i represents the index of a given SNP;
(iv) $\beta_i$ is the log odds ratio of the ith SNP; and
(v) $G_i = \{0,1,2\}$ is the number of copies of the SNP in the sample from the individual.

* * * * *

SEQUENCE LISTING

```
<160> NUMBER OF SEQ ID NOS: 33

<210> SEQ ID NO 1
<211> LENGTH: 440
<212> TYPE: PRT
<213> ORGANISM: Artificial Sequence
<220> FEATURE:
<223> OTHER INFORMATION: Synthetic construct

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255
```

```
Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
            435                 440

<210> SEQ ID NO 2
<211> LENGTH: 214
<212> TYPE: PRT
<213> ORGANISM: Artificial Sequence
<220> FEATURE:
<223> OTHER INFORMATION: Synthetic construct

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 118
<212> TYPE: PRT
<213> ORGANISM: Artificial Sequence
<220> FEATURE:
<223> OTHER INFORMATION: Synthetic construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 4
<211> LENGTH: 108
<212> TYPE: PRT
<213> ORGANISM: Artificial Sequence
<220> FEATURE:
<223> OTHER INFORMATION: Synthetic construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 5
<211> LENGTH: 10
<212> TYPE: PRT
<213> ORGANISM: Artificial Sequence
```

```
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: Xaa is Asp or Gly

<400> SEQUENCE: 5

Gly Phe Thr Phe Ser Xaa Ser Trp Ile His
1               5                   10

<210> SEQ ID NO 6
<211> LENGTH: 18
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Ser or Leu
<220> FEATURE:
<221> NAME/KEY: MISC_FEATURE
<222> LOCATION: (10)..(10)
<223> OTHER INFORMATION: Xaa is Thr or Ser

<400> SEQUENCE: 6

Ala Trp Ile Xaa Pro Tyr Gly Gly Ser Xaa Tyr Tyr Ala Asp Ser Val
1               5                   10                  15

Lys Gly

<210> SEQ ID NO 7
<211> LENGTH: 9
<212> TYPE: PRT
<213> ORGANISM: Artificial Sequence
<220> FEATURE:
<223> OTHER INFORMATION: Synthetic construct

<400> SEQUENCE: 7

Arg His Trp Pro Gly Gly Phe Asp Tyr
1               5

<210> SEQ ID NO 8
<211> LENGTH: 25
<212> TYPE: PRT
<213> ORGANISM: Artificial Sequence
<220> FEATURE:
<223> OTHER INFORMATION: Synthetic construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 9
<211> LENGTH: 13
<212> TYPE: PRT
<213> ORGANISM: Artificial Sequence
<220> FEATURE:
<223> OTHER INFORMATION: Synthetic construct

<400> SEQUENCE: 9

Trp Val Arg Gln Ala Pro Gly Lys Gly Leu Glu Trp Val
1               5                   10

<210> SEQ ID NO 10
```

```
<211> LENGTH: 32
<212> TYPE: PRT
<213> ORGANISM: Artificial Sequence
<220> FEATURE:
<223> OTHER INFORMATION: Synthetic construct

<400> SEQUENCE: 10

Arg Phe Thr Ile Ser Ala Asp Thr Ser Lys Asn Thr Ala Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 11
<211> LENGTH: 11
<212> TYPE: PRT
<213> ORGANISM: Artificial Sequence
<220> FEATURE:
<223> OTHER INFORMATION: Synthetic construct

<400> SEQUENCE: 11

Trp Gly Gln Gly Thr Leu Val Thr Val Ser Ser
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: Xaa is Asp or Val
<220> FEATURE:
<221> NAME/KEY: MISC_FEATURE
<222> LOCATION: (6)..(6)
<223> OTHER INFORMATION: Xaa is Val or Ile
<220> FEATURE:
<221> NAME/KEY: MISC_FEATURE
<222> LOCATION: (7)..(7)
<223> OTHER INFORMATION: Xaa is Ser or Asn
<220> FEATURE:
<221> NAME/KEY: MISC_FEATURE
<222> LOCATION: (9)..(9)
<223> OTHER INFORMATION: Xaa is Ala or Phe
<220> FEATURE:
<221> NAME/KEY: MISC_FEATURE
<222> LOCATION: (10)..(10)
<223> OTHER INFORMATION: Xaa is Val or Leu

<400> SEQUENCE: 12

Arg Ala Ser Gln Xaa Xaa Xaa Thr Xaa Xaa Ala
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Xaa is Phe or Thr
<220> FEATURE:
<221> NAME/KEY: MISC_FEATURE
<222> LOCATION: (6)..(6)
<223> OTHER INFORMATION: Xaa is Tyr or Ala

<400> SEQUENCE: 13

Ser Ala Ser Xaa Leu Xaa Ser
```

```
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: Xaa is Tyr, Gly, Phe, or Ser
<220> FEATURE:
<221> NAME/KEY: MISC_FEATURE
<222> LOCATION: (4)..(4)
<223> OTHER INFORMATION: Xaa is Leu, Tyr, Phe, or Trp
<220> FEATURE:
<221> NAME/KEY: MISC_FEATURE
<222> LOCATION: (5)..(5)
<223> OTHER INFORMATION: Xaa is Tyr, Asn, Ala, Thr, Gly, Phe, or Ile
<220> FEATURE:
<221> NAME/KEY: MISC_FEATURE
<222> LOCATION: (6)..(6)
<223> OTHER INFORMATION: Xaa is His, Val, Pro, Thr, or Ile
<220> FEATURE:
<221> NAME/KEY: MISC_FEATURE
<222> LOCATION: (8)..(8)
<223> OTHER INFORMATION: Xa is Ala, Trp, Arg, Pro, or Thr

<400> SEQUENCE: 14

Gln Gln Xaa Xaa Xaa Xaa Pro Xaa Thr
1               5

<210> SEQ ID NO 15
<211> LENGTH: 23
<212> TYPE: PRT
<213> ORGANISM: Artificial Sequence
<220> FEATURE:
<223> OTHER INFORMATION: Synthetic construct

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic construct

<400> SEQUENCE: 16

Trp Tyr Gln Gln Lys Pro Gly Lys Ala Pro Lys Leu Leu Ile Tyr
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: Synthetic construct

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30
```

```
<210> SEQ ID NO 18
<211> LENGTH: 11
<212> TYPE: PRT
<213> ORGANISM: Artificial Sequence
<220> FEATURE:
<223> OTHER INFORMATION: Synthetic construct

<400> SEQUENCE: 18

Phe Gly Gln Gly Thr Lys Val Glu Ile Lys Arg
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic construct

<400> SEQUENCE: 19

Gly Phe Thr Phe Ser Asp Ser Trp Ile His
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Synthetic construct

<400> SEQUENCE: 20

Ala Trp Ile Ser Pro Tyr Gly Gly Ser Thr Tyr Tyr Ala Asp Ser Val
1               5                   10                  15

Lys Gly

<210> SEQ ID NO 21
<211> LENGTH: 9
<212> TYPE: PRT
<213> ORGANISM: Artificial Sequence
<220> FEATURE:
<223> OTHER INFORMATION: Synthetic construct

<400> SEQUENCE: 21

Arg His Trp Pro Gly Gly Phe Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic construct

<400> SEQUENCE: 22

Arg Ala Ser Gln Asp Val Ser Thr Ala Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic construct

<400> SEQUENCE: 23

Ser Ala Ser Phe Leu Tyr Ser
```

```
<210> SEQ ID NO 24
<211> LENGTH: 9
<212> TYPE: PRT
<213> ORGANISM: Artificial Sequence
<220> FEATURE:
<223> OTHER INFORMATION: Synthetic construct

<400> SEQUENCE: 24

Gln Gln Tyr Leu Tyr His Pro Ala Thr
1               5

<210> SEQ ID NO 25
<211> LENGTH: 122
<212> TYPE: PRT
<213> ORGANISM: Artificial Sequence
<220> FEATURE:
<223> OTHER INFORMATION: Synthetic construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120

<210> SEQ ID NO 26
<211> LENGTH: 10
<212> TYPE: PRT
<213> ORGANISM: Artificial Sequence
<220> FEATURE:
<223> OTHER INFORMATION: Synthetic construct

<400> SEQUENCE: 26

Phe Gly Gln Gly Thr Lys Val Glu Ile Lys
1               5                   10

<210> SEQ ID NO 27
<211> LENGTH: 30
<212> TYPE: PRT
<213> ORGANISM: Artificial Sequence
<220> FEATURE:
<223> OTHER INFORMATION: Synthetic construct

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30
```

```
<210> SEQ ID NO 28
<211> LENGTH: 14
<212> TYPE: PRT
<213> ORGANISM: Artificial Sequence
<220> FEATURE:
<223> OTHER INFORMATION: Synthetic construct

<400> SEQUENCE: 28

Trp Val Arg Gln Ala Pro Gly Lys Gly Leu Glu Trp Val Ala
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Synthetic construct

<400> SEQUENCE: 29

Trp Gly Gln Gly Thr Leu Val Thr Val Ser Ser Ala Ser Thr Lys
1               5                   10                  15

<210> SEQ ID NO 30
<211> LENGTH: 447
<212> TYPE: PRT
<213> ORGANISM: Artificial Sequence
<220> FEATURE:
<223> OTHER INFORMATION: Synthetic construct

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 31
<211> LENGTH: 214
<212> TYPE: PRT
<213> ORGANISM: Artificial Sequence
<220> FEATURE:
<223> OTHER INFORMATION: Synthetic construct

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 32
<211> LENGTH: 115
<212> TYPE: PRT
<213> ORGANISM: Artificial Sequence
<220> FEATURE:
<223> OTHER INFORMATION: Synthetic Construct

<400> SEQUENCE: 32

Gln Ser Leu Glu Glu Ser Gly Gly Arg Leu Val Lys Pro Asp Glu Thr
1               5                   10                  15

Leu Thr Ile Thr Cys Thr Val Ser Gly Ile Asp Leu Ser Ser Asn Gly
            20                  25                  30

Leu Thr Trp Val Arg Gln Ala Pro Gly Glu Gly Leu Glu Trp Ile Gly
            35                  40                  45

Thr Ile Asn Lys Asp Ala Ser Ala Tyr Tyr Ala Ser Trp Ala Lys Gly
        50                  55                  60

Arg Leu Thr Ile Ser Lys Pro Ser Ser Thr Lys Val Asp Leu Lys Ile
65                  70                  75                  80

Thr Ser Pro Thr Thr Glu Asp Thr Ala Thr Tyr Phe Cys Gly Arg Ile
                85                  90                  95

Ala Phe Lys Thr Gly Thr Ser Ile Trp Gly Pro Gly Thr Leu Val Thr
            100                 105                 110

Val Ser Ser
        115

<210> SEQ ID NO 33
<211> LENGTH: 112
<212> TYPE: PRT
<213> ORGANISM: Artificial Sequence
<220> FEATURE:
<223> OTHER INFORMATION: Synthetic Construct

<400> SEQUENCE: 33

Ala Ile Val Met Thr Gln Thr Pro Ser Pro Val Ser Ala Ala Val Gly
1               5                   10                  15

Gly Thr Val Thr Ile Asn Cys Gln Ala Ser Glu Ser Val Tyr Ser Asn
            20                  25                  30

Asn Tyr Leu Ser Trp Phe Gln Gln Lys Pro Gly Gln Pro Pro Lys Leu
            35                  40                  45

Leu Ile Tyr Leu Ala Ser Thr Leu Ala Ser Gly Val Pro Ser Arg Phe
        50                  55                  60

Lys Gly Ser Gly Ser Gly Thr Gln Phe Thr Leu Thr Ile Ser Gly Val
65                  70                  75                  80

Gln Cys Asp Asp Ala Ala Thr Tyr Tyr Cys Ile Gly Gly Lys Ser Ser
                85                  90                  95

Ser Thr Asp Gly Asn Ala Phe Gly Gly Gly Thr Glu Val Val Val Arg
            100                 105                 110